United States Patent
Biedermann et al.

(10) Patent No.: US 7,320,993 B1
(45) Date of Patent: *Jan. 22, 2008

(54) ARYL-SUBSTITUTED PYRIDYLALKANE, ALKENE, AND ALKINE CARBOXAMIDES USEFUL AS CYTOSTATIC USEFUL AS CYTOSTATIC AND IMMUOSUPPRESSIVE AGENTS

(75) Inventors: Elfi Biedermann, Vaterstetten (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Klaus Seibel, Gräfelfing (DE); Klaus Vogt, Munich (DE); Katja Wosikowski, Poing (DE); Isabel Schemainda, Munich (DE)

(73) Assignee: Astellas Deutschland GmbH, Munich (DE)

( * ) Notice: Subject to any disclaimer, the term of this patent is extended or adjusted under 35 U.S.C. 154(b) by 161 days.

This patent is subject to a terminal disclaimer.

(21) Appl. No.: 09/596,086

(22) Filed: Jun. 16, 2000

Related U.S. Application Data

(63) Continuation of application No. PCT/EP98/08272, filed on Dec. 16, 1998.

(30) Foreign Application Priority Data

Dec. 17, 1997 (DE) ................................. 197 56 261

(51) Int. Cl.
*A61K 31/44* (2006.01)
*A61P 31/00* (2006.01)
*A61P 35/00* (2006.01)
*C07D 211/00* (2006.01)
*C07D 213/00* (2006.01)

(52) U.S. Cl. ........................ 514/357; 514/89; 514/344; 514/348; 514/349; 514/350; 514/351; 514/352; 514/354; 514/355; 514/356; 546/22; 546/24; 546/285; 546/286; 546/287; 546/288; 546/289; 546/290; 546/296; 546/297; 546/300; 546/309; 546/310; 546/312; 546/315; 546/316; 546/318; 546/321; 546/322; 546/323; 546/326; 546/328; 546/330; 546/332; 546/335; 546/337

(58) Field of Classification Search ................. 514/89, 514/344, 348, 349, 350, 351, 352, 354, 355, 514/356, 357; 546/22, 24, 285, 286, 287, 546/288, 289, 290, 296, 297, 300, 309, 310, 546/312, 315, 316, 318, 321, 322, 323, 326, 546/328, 330, 332, 335, 337

See application file for complete search history.

(56) References Cited

U.S. PATENT DOCUMENTS

| 4,283,541 A | 8/1981 | Shroff et al. | 546/336 |
|---|---|---|---|
| 5,169,856 A | 12/1992 | Goto et al. | 514/331 |
| 5,260,323 A | 11/1993 | Baader et al. | 514/356 |
| 5,326,772 A | 7/1994 | Klemm et al. | 514/318 |
| 5,925,527 A * | 7/1999 | Hayes et al. | 435/7.1 |
| 6,313,153 B1 * | 11/2001 | Hasegawa et al. | 514/357 |
| 6,506,572 B2 * | 1/2003 | Biedermann et al. | 435/15 |

FOREIGN PATENT DOCUMENTS

| CA | 2085954 | 6/1993 |
|---|---|---|
| DE | 4020570 | 1/1992 |
| EP | 048045 | 3/1982 |
| EP | 210782 | 2/1987 |
| EP | 271023 | 6/1988 |
| EP | 330026 | 8/1989 |
| EP | 343307 | 11/1989 |
| EP | 416581 | 3/1991 |
| EP | 471236 | 2/1992 |
| EP | 479601 | 4/1992 |
| EP | 522606 | 1/1993 |
| EP | 530444 | 3/1993 |

(Continued)

OTHER PUBLICATIONS

CAPLUS printout of the references cited in the attached office action, 2002.*

(Continued)

*Primary Examiner*—Brenda Coleman
(74) *Attorney, Agent, or Firm*—Scully, Scott, Murphy & Presser, P.C.

(57) ABSTRACT

The invention relates to new pyridylalkane, alkene, and alkine acid amides substituted with an aryl and/or heteroaryl residue according to the general formula (I), with a saturated or one or several-fold unsaturated hydrocarbon residue in the carboxylic acid group, methods for the synthesis of these compounds, medicaments containing these and their production as well as their therapeutic use, especially as cytostatic agents and immunosuppressive agents, for example in the treatment or prevention of various types of tumors and control of immune reactions such as autoimmune diseases.

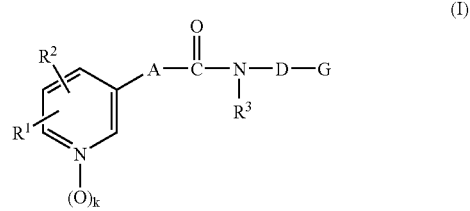

18 Claims, No Drawings

FOREIGN PATENT DOCUMENTS

| | | |
|---|---|---|
| EP | 548883 | 6/1993 |
| EP | 512902 | 4/1994 |
| EP | 428434 | 5/1994 |
| GB | 2304714 | 11/1998 |
| JP | 57136518 | 8/1982 |
| JP | 63179869 | 7/1988 |
| WO | WO89/07443 | 8/1989 |
| WO | WO91/15484 | 10/1991 |
| WO | WO91/15485 | 10/1991 |
| WO | WO93/14113 | 7/1993 |
| WO | WO95/10514 | 4/1995 |
| WO | WO95/10515 | 4/1995 |
| WO | WO96/31478 | 10/1996 |
| WO | WO97/48695 | 1/1997 |
| WO | WO97/48397 | 12/1997 |
| WO | WO 98/34111 * | 8/1998 |

OTHER PUBLICATIONS

Nishikawa et al., "Acrylamide Derivatives as Antiallergic Agents. 2. Synthesis and Structure-Activity Relationships of N-[4-[4-(Diphenylmethyl)-1-piperazinyl]butyl]-3-(3-pyridyl) acrylamides" Chem. Pharm. Bull. 37(1) 100-105 (1989).

Nishikawa et al., "Acrylamide Derivatives as Antiallergic Agents. 2. Synthesis and Structure-Activity Relationships of N-[4-[4-(Diphenylmethyl)-1-piperazinyl]butyl]-3-(3-pyridyl) acrylamides" J. Med. Chem. 1989, 32, 583-593.

Ishihara et al., "Central Cholinergic Agents. II. Synthesis and Acetylcholinesterase Inhibitory Activities of N-[w-[N-Alkyl-N-(phenylmethyl) amino]alkyl]-3-arylpropenamides" Chem. Pharm. Bull. 39 (12) 3236-3234 (1991).

Ross, "The Preparation of Some 4-Substituted Nicotinic Acids and Nicotinamides" J. Chem. Soc. (C), 1966, 1816-1820.

M. Eder, P. Gedigk, (Ed.) "Allgemeine Pathologie und Pathologische Anatomie", Springer Verlag, Berlin, 33rd Ed., 1990, pp. 208-213 and translation of relevant passages thereof.

Chemical Abstracts, vol. 124, No. 13, 1996, p. 1004, 1730 15r.

Chemical Abstracts, vol. 115, 1991, p. 48, 150041w.

Chemical Abstracts, vol. 114, 1991, p. 714, 101646t.

* cited by examiner

ARYL-SUBSTITUTED PYRIDYLALKANE, ALKENE, AND ALKINE CARBOXAMIDES USEFUL AS CYTOSTATIC USEFUL AS CYTOSTATIC AND IMMUOSUPPRESSIVE AGENTS

This is a continuation of prior application number PCT/EP98/08272, filed 16 Dec. 1998 and designating the U.S., which is hereby incorporated herein by reference in its entirety.

The invention relates to new pyridylalkane, alkene and alkine carboxamides substituted with a saturated, one or several-fold unsaturated hydrocarbon residue in the carboxylic acid grouping, methods for the synthesis of these compounds, medicaments containing these and their production as well as their therapeutic use especially as cytostatic agents and immunosuppressive agents, for example, in the treatment or prevention of various types of tumors and control of immune reactions, for example of autoimmune diseases.

A pressing need exists for new pharmaceuticals and/or medicaments for cytostatic therapy which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

Additionally, from another point of view, there exists a strong need in the field of tumor therapy for new compounds, for example for overcoming or avoiding resistances, which enrich the pallet of cancerostatics based on new modes of action in the ideal case.

This object was successfully solved by the creation of the pyridylalkane, alkene and alkine carboxamide derivatives as defined in detail in the claims and medicaments containing these as well as the use of these compounds, optionally in combination with other suitable active ingredients and adjuvants, especially for cytostatic and immunosuppressive therapy or prevention.

It is known from the art that various pyridine compounds substituted in a specific manner have pharmacologically useful properties; however, in contrast to the actions of the compounds according to the invention, these lie in completely different fields of indication.

Thus, ω-pyridylalkane and/or alkene amides with anti-allergic activity are described in EP 0 210 782 which are referred to as having a 5-lipoxygenase-inhibiting and anti-histamine action, wherein the amide components of these compounds contain a piperizine or homopiperizine ring and the pyridine ring can be linked together in the 2-, 3- or 4-position.

JP 63,179,869 describes further pyridyl amides, co-pyridyl alkane and alkene amides as anti-allergic effective substances containing a substituted piperidine ring in the amine component. Similarly structured compounds with the same properties are mentioned in Chem. Pharm. Bull 37, 100-105 (1989) as well as in J. Med. Chem. 1989, 583-593.

The synthesis and pharmacological evaluation of heterocyclic carboxamides which can be substituted at an end of the molecule by completely different heterocycles such as thiophene, quinoline, indole, benzimidazole or indazole as well as pyridine are described in J. Med. Chem., 1996, pages 4692-4706. However, these compounds possess an activity directed against psychoses.

Pyridyl ureas, pyridyl thioureas and pyridyl carbonamides, wherein the amide portion is bound over an aryl-substituted alkyl chain with a piperidine ring or piperidine ring or piperazine ring, are described for example in EP-A-0 428 434 or in the publication EP-A-0 512 902 as antagonists of the neurokinin receptor and substance P. Furthermore, pyridyl(alkyl)carbonamides, pyridyl(alkyl)sulfonamides and analogous ureas, wherein the amide portion is bound to piperidine ring over an alkyl chain, are disclosed in published EP-A-0 479 601 as active ingredients with anti-arrhythmic properties.

Further structurally closely related compounds are represented by the piperidine compounds described in EP-A-0 330 026. These known compounds are distinguished by an anti-cholinesterase activity, an anti-amnesia activity as well as activities directed against hyperkinesia, senile dementia, mania and Alzheimer's disease.

Compounds in the form of α,ω-diaryl-substituted 2-aminopentan-3-oles or 4-aminopent-1-en-3-oles whose nitrogen atom can be substituted, among others, by 3- or 4-pyridylcarbonyl, pyridylalkylcarbonyl or pyridylalkenecarbonyl are known from WO 94/01402 on the basis of a few exemplified substitutions. However, these known compounds represent tachykinin antagonists which are used for the treatment of pain, inflammation, migraines and arthritis.

Further amides with a piperidine residue and specific several-fold substituted 2-aryl-4-piperidyl-butylamine and their use as neurokinin antagonists are named in GB 2 304 714 A, however no concrete examples of a compound are disclosed for a 3-pyridyl substitution as an aryl residue.

Aside from esters, ethers, thioethers or thioamides and many other functional derivatives, alkane and alkene amides of ω-imidazolyl alkane/alkene amines with a chain of up to 6 C-atoms are also comprised by the general formula published in WO 93/14070 as antagonists of the histamine-$H_3$ receptor with anti-convulsive, anti-depressive, anti-allergic and anti-secretory action. However, not a single example of a compound is concretely described or even mentioned for a pyridyalkane or alkene amide.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(-)-niguldipin and further analogous dihydropyridines with cytotoxic activity have larger structural differences. However, as compared to these known pyridyl compounds, the compounds according to the invention unexpectedly possess a better activity and a wider spectrum of action despite the large structural difference, whereby the therapy possibilities according to the invention with the new compounds extend to the combat of numerous other types of tumors with different causal mechanisms as well as for immunosuppressive treatment possibilities such as autoimmune diseases.

In view of this art, the finding that the compounds according to the general formula (I) with the particular substitutions defined below have superior pharmacological activities which make them particularly suitable in an excellent manner for the therapy of tumor illnesses over a broad anti-proliferative spectrum, was completely unexpected.

The pharmacological finding that, aside from the cytostatic effectiveness, especially with different tumor spectra, the compounds according to the invention also possess immunosuppressive properties and additionally favorable abortive properties without harmful mutagenic effects is to be considered as equally surprising. As a result of the particular molecular structure now found, a further class of compounds with, among others, pronounced cancerostatic, cytostatic, anti-proliferative and abnormal cell growth-inhibiting activity with a novel mode of action is offered.

The new aryl-substituted pyridyl carboxamides are comprised by the following general formula:

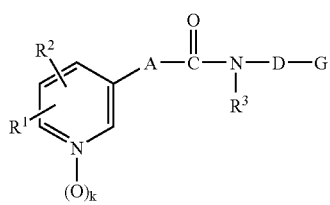
(I)

wherein G is selected from G1, G2, G3, G4, G5 or G6 under the proviso that G must contain at least one aromatic ring thereby G1, G2, G3, G4, C5 and G6 correspond to the following formulas:

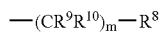
(G1)

(G2)

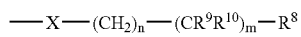
(G3a)

(G3b)

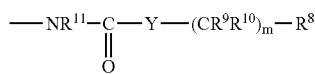
(G4a)

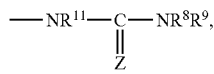
(G4b)

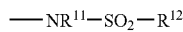
(G5)

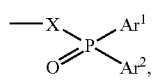
(G6)

whose substituent meanings are more closely specified below.

The synthesis of these new compounds occurs by means of known analogous methods, whose suitable provisions, reactants such as respective suitable starting and intermediate products as well as solvents are illustrated below in detail. Summarizing, the various suitable method variants are based on the following steps:

according to method (A), compounds of the formula (I) are prepared in the manner that carboxylic acids of formula (II),

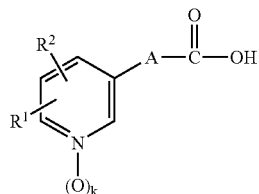
(II)

wherein $R^1$, $R^2$, A and k have the meanings given above or their reactive derivatives are reacted with compounds of formula (III)

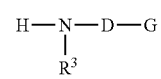
(III)

wherein D, G and $R^3$ are defined above, for example in the form of their activated esters, anhydrides, acid halides, especially acid chlorides, or simple lower alkyl esters as free bases or acid addition salts, optionally in the presence of condensation agents, for example carbodiimides, in a suitable, preferably inert solvent or polar aprotic solvent or solvent mixture, as well as, optionally, in the presence of an auxiliary base in the form of a carbonate or organic amine, at a reaction temperature especially between −40° C. and 180° C., preferably between −10° C. and 130° C.; or according to method (B), compounds of formula (I), wherein G corresponds to the meanings of G3a, G4, G5 or G6, and, optionally X is equal to $NR^{11}$, can be produced that compounds of formula (IV)

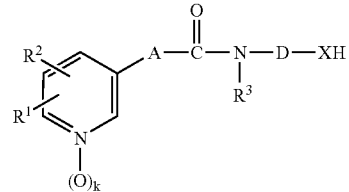
(IV)

are reacted with suitable alkylation or arylation agents and/or carboxylic acid, carbamic acid, thiocarbamic acid, sulfonic acid or phosphinic acid derivatives of formula (Va) to (Ve),

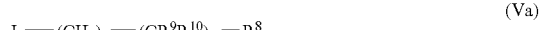
(Va)

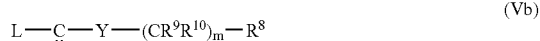
(Vb)

(Vc)

(Vd)

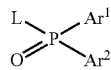 (Ve)

wherein each L represents a suitable nucleofuge, or according to method (B1), compounds of formula (I), wherein G has the meanings of G3a with X=NR$^{11}$ according to the above definition, can also be produced in the manner that compounds of formula (IV) are reacted in a suitable inert solvent and/or solvent mixture with a suitable alkylation and/or arylation agent of formula (Va), wherein m, n, R$^8$, R$^9$ and R$^{10}$ are defined as above and the leaving group L can be a reactive derivative of an alcohol, for example a halogen atom, or sulfonic acid ester, whereby the reaction preferably takes place in the presence of bases as named above in method (A) and, in the case of the use of compounds of formula (Va) in the form of their chlorides or bromides as starting products, the reaction can be accelerated by addition of alkali metal iodides such as sodium iodide or potassium iodide and whereby the reaction temperature can vary, especially between 0° C. and 180° C., preferably between 20° C. and 130° C.; or according to method (B2), compounds of formula (I), wherein G has the meaning G4 to G6 according to the above definition, can also be produced in that starting products of formula (IV) are reacted with a carboxylic acid, thiocarbamic acid carbamic acid, sulfonic acid and/or phosphinic acid of formula (VIb) to (VIe),

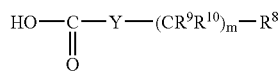 (VIb)

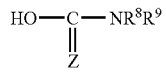 (VIc)

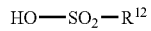 (VId)

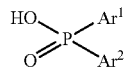 (VIe)

wherein m, Y, Z, R$^8$, R$^9$, R$^{10}$, R$^{12}$, Ar$^1$, Ar$^2$ and optionally the group NR$^8$R$^9$ have the above meanings or with their derivatives capable of reaction, preferably in the presence of auxiliary bases in solvents and under conditions as they are described in method (A), or according to method (B3), compounds of formula (I), herein G represents a carbamoyl residue according to the definition G4b with Z=O, i.e. is a group

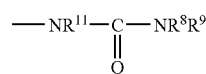

can also be produced in the manner that compounds of formula (IV), wherein X=NR$^{11}$ are reacted to an intermediate product with a carbonyl group transmitter, preferably with a bis-trichloromethy carbonate (triphosgene) or carbonyldiimidazole, especially in an absolute, inert solvent in the presence of a tertiary organic amine as an auxiliary base and, subsequently, without purification or isolation of the intermediate product, this is reacted with a primary or secondary amine of formula (VII),

H—NR$^8$R$^9$ (VII)

wherein R$^8$ and R$^9$ or optionally the residue NR$^8$R$^9$ have the meanings according to the above definitions, whereby the temperature for the first partial reaction can lie especially between −40° C. and 50° C., preferably at 0° C. to 30° C., and, for the second partial reaction, between 0° C. and 150° C., preferably in the range of 20° C. to 120° C., and whereby compounds of formula (I) wherein G represents a thiocarbamoyl residue according to the definition G4b with Z=S, i.e. is a group

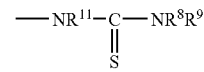

can be produced in an identical manner from the starting compounds of the formulas (IV) and (VII) in that thiocarbonyldiimidazole or thiophosgene is used as a thiocarbonyl group transmitter, or according to method (B4), compounds of formula (I), wherein G represents a carbamoyl residue or thiocarbamoyl residue according to the definition G4b with R$^9$=hydrogen, i.e. is a group

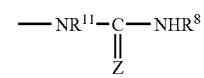

can be produced in the manner, that the starting compounds of formula (IV), wherein X=NR$^{11}$ are reacted with an isocyanate or isothiocyanate of formula (VIII),

Z=C=N—R$^8$ (VIII)

wherein R$^8$ has the meanings defined above, preferably in absolute, inert solvents as they are considered in the above method (B3), especially at a reaction temperature which can vary in the range of −20° C. to 150° C., preferably at 20° C. to 100° C.

Subject matter of the invention are further pharmacologically acceptable acid addition salts of the compounds of Formula (I) with inorganic or organic acids. Preferable examples for addition salts with suitable inorganic acids are hydrochlorides, hydrobromides, hydroiodides, sulfates and phosphates. Addition salts of organic acids are preferably acetates, benzoates, citrates, fumarates, gluconates, malates, maleates, methanesulfonates, lactates, oxalates, succinates, tartrates and tosylates.

Compounds of Formula (I) as well as their acid addition salts can also be optionally present as hydrates or other solvates. The invention includes such hydrates and solvates.

In the compounds of Formula (I) which are defined below and in the claims in detail, the definitions for their atoms or atomic groups preferably have the following meanings:

Halogen means fluorine, chlorine, bromine or iodine;

Alkyl can be straight chained or branched and preferably signifies a C$_1$-C$_6$-alkyl residue, especially a methyl-, ethylpropyl-, isopropyl-, butyl-, isobutyl-, sec-butyl-, tert-butyl-, cyclopropylmethyl-, pentyl-, isopentyl-, tert-pentyl-neopentyl-, cyclopropylethyl-, cyclobutylmethyl- or hexyl group.

Alkylene signifies for example methylene, ethylene, propylene, tetramethylene, pentamethylene, hexamethylene, heptamethylene, octamethylene, nonamethylene, decamethylene, undecamethylene or dodecamethylene.

Alkenyl preferably signifies $C_3$-$C_6$-alkenyl and can be straight chained or branched and preferably signifies an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl-group.

Alkenylene signifies for example ethenylene, propenylene, butenylene, pentenylene, hexenylene, hexadienylene, heptenylene, heptadienylene, octenylene, octadienylene, nonenylene, nonadienylene or decenylene, decadienylene, undecenylene, undecadienylene, dodecenylene or dodecadienylene.

Alkinyl preferably signifies $C_2$-$C_6$-alkinyl which can be straight chained or branched and can preferably signify an ethinyl-, propargyl-, 2-butinyl-, 3-butinyl-, 4-pentinyl-, 5-hexinyl- or 4-methyl-2-pentinyl group.

Alkinylene signifies for example propinylene, butinylene, pentinylene, hexinylene, hexeninylene, heptinylene, octinylene, noninylene, noneninylene, decinylene, deceninylene, undecinylene or dodecinylene.

Cycloalkyl is preferably a $C_3$-$C_8$-cycloalkyl residue, especially a cyclopropyl-, cyclobutyl-, cyclopentyl-, cyclohexyl-, cycloheptyl- or cyclooctyl group.

Cycloalkylene preferably signifies cyclopropylene, cyclobutylene, cyclopentylene, cyclohexylene, cycloheptylene or cyclooctylene.

Hydroxyalkyl contains a hydroxyl group in one of the above mentioned alkyl residues, especially in a $C_1$-$C_6$-alkyl residue, whereby among the $C_1$-$C_6$-hydroxyalkyl residues, the hydroxymethyl- and the hydroxyethyl residue are preferred.

Aside from the oxygen atom, alkoxy residues, preferably $C_1$-$C_6$-alkoxy or $C_3$-$C_8$-cycloalkoxy, especially contain one of the above mentioned preferred alkyl and/or cycloalkyl groups with up to 6 or 8 carbon atoms. Particularly preferred groups for this are the methoxy-, ethoxy-, isopropoxy-, tert-butoxy-, cyclopentyloxy- and cyclohexyloxy groups.

Alkoxy, especially $C_1$-$C_6$-alkoxy, entirely or partially replaced by fluorine is for example difluoromethoxy, trifluoromethoxy or 2,2,2-trifluoroethoxy.

Aralkyl such as phenylalkyl, especially phenyl-$C_1$-$C_3$-alkyl and/or diarylalkyl such as diphenyl-$C_1$-$C_3$-alkyl or triaralkyl such as triphenylmethyl contain 1 and/or 2 and/or 3 phenyl groups on a methyl-, ethyl-, propyl- or isopropyl group at any position. Among these, benzyl- and diphenylmethyl residues are particularly preferred.

Aside from the sulphur atom, alkylthio residues contain one of the above mentioned preferred $C_1$-$C_6$-alkyl groups, especially the methylthio-, ethylthio-, isopropylthio- and tert-butylthio groups.

Aside from the oxygen atom, alkanoyloxy residues preferably contain an aliphatic acyl group with 1 to 7 carbon atoms. Among preferred alkanoyloxy groups are the acetoxy-, propionyloxy- and pivaloyloxy groups.

Carboxyalkyl, especially $C_2$-$C_7$-carboxyalkyl, and carboxyalkenyl, especially $C_3$-$C_7$-carboxyalkenyl, contain a carboxyl group on one of the above named alkylene and alkenyl residues especially $C_1$-$C_6$-alkylene and/or $C_2$-$C_6$-alkenylene residues. Among these, the carboxymethyl-, carboxyethyl-, carboxyethenyl-, carboxybutyl- and carboxybutadienyl residues are preferred.

Alkoxycarbonyl groups, preferably $C_2$-$C_7$-alkoxycarbonyl groups contain, aside from the carbonyl group, one of the above mentioned alkoxy groups, especially $C_1$-$C_6$-alkoxy groups. Preferred alkoxycarbonyl groups are the methoxycarbonyl-, ethoxycarbonyl-, isopropoxycarbonyl-, isobutoxycarbonyl- and tert-butoxycarbonyl groups.

Aside from the carbonyl group, alkylaminocarbonyl, especially $C_2$-$C_7$-alkylaminocarbonyl and dialkylaminocarbonyl groups, preferably $C_3$-$C_{13}$-dialkylaminocarbonyl groups, contain an alkylamino- and/or dialkylamino residue whose alkyl groups especially correspond to the $C_1$-$C_6$-alkyl groups of the above description. Preferred groups are the dimethylaminocarbonyl-, diethylaminocarbonyl- and diisopropylaminocarbonyl groups.

Aminoalkyl residues, especially $C_1$-$C_6$-aminoalkyl residues, each contain an amino group in one of the above named $C_1$-$C_6$-alkyl residues, hereby the aminomethyl- and aminoethyl groups are particularly preferred.

Aside from the unsubstituted amino group, the amino group of the Formula $NR^4R^5$ is one of the below mentioned alkylamino groups, especially $C_1$-$C_6$-alkylamino groups and/or dialkyl-amino groups, especially di-($C_1$-$C_6$-alkyl) amino groups.

Alkylamino especially contains one of the above mentioned $C_1$-$C_6$-alkyl groups. Preferred groups are the methylamino-, ethylamino-, propylamino-, isopropylamino-, butylamino-, and the tert-butylamino groups.

The preferred di-($C_1$-$C_6$-alkyl)amino residue carries two of the same or different of the above mentioned $C_1$-$C_6$-alkyl groups on the nitrogen atom. Preferred groups are the dimethylamino-, diethylamino-, dipropylamino-, diisopropylamino-, isopropyl-, methylamino-, dibutylamino- or tert-butylmethylamino groups.

Acyl, especially $C_1$-$C_6$-acyl, signifies the residue of an aliphatic saturated or unsaturated, straight chained, branched or cyclic carboxylic acid. Preferred acyl residues are formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and dimethylacryloyl groups.

Alkanesulfonyl, especially $C_1$-$C_6$-alkanesulfonyl is preferably the methanesulfonyl-, ethanesulfonyl-, propanesulfonyl-, butanesulfonyl-, pentanesulfonyl- or hexanesulfonyl groups.

Saturated four- to seven-membered heterocycles with one or two hetero-atoms, are for example azetidine, tetrahydrofuran, tetrahydrothiophene, pyrrolidine, tetrahydropyran, tetrahydropyridine, piperidine, hexahydroazepine, piperazine, morpholine, thiomorpholine, hexahydrodiazepine or hexahydrooxazepine.

Monocyclic aromatic five- or six-membered heterocycles with one to three hetero-atoms are for example furyl, thienyl, pyrrolyl, oxazolyl, isoxazolyl, thiazolyl, isothiazolyl, imidazolyl, pyrazolyl, oxadiazolyl, thiadiazolyl, triazolyl, pyridinyl, pyrazinyl, pyridazinyl, pyrimidinyl or triazinyl.

Anellated bi- and tricyclic aromatic or partially hydrated carbocyclic ring systems with 8 to 16 ring atoms and at least one aromatic ring are preferably benzocyclobutyl, indanyl, indenyl, naphthyl, dihydronaphthyl, tetrahydronaphthyl, dihydrobenzocycloheptenyl, tetrahydrobenzocycloheptenyl, biphenylenyl, fluoroenyl, anthryl, dihydroanthryl, phenanthryl, dihydrophenanthryl, dibenzocycloheptenyl, dihydrodibenzocycloheptenyl, dihydrodibenzocyclooctenyl or tetrahydrodibenzocyclooctenyl. Their mono- or dioxoderivates, i.e. for example the residues of indanone, tetralone, anthrone, anthraquinone, fluoroenone, phenanthrone, dibenzocycloheptenone, dihydrodibenzo-cycloheptenone or tetrahydrodibenzocyclooctenone are also to be understood as partially hydrated carbocyclic ring systems.

Anellated bi- and tricyclic aromatic or partially hydrated heterocyclic ring systems with 8 to preferably 16 ring atoms and at least one aromatic ring are, for example, imidazothiazolyl, benzofuryl, dihydrobenzofuryl, benzo-thienyl, dihydrobenzothienyl, indolyl, indolinyl, isoindolinyl, benzimidazolyl, indazolyl, benzooxazolyl, benzoisoxazolyl, benzothiazolyl, benzoisothiazolyl, benzofurazanyl, benzothiadiazolyl, benzotriazolyl, oxazolopyridyl, thiazolopyridyl, isothiazolopyridyl, imidazopyridyl, pyrazolopyridyl, thienopyrimidinyl, chromanyl, benzopyranyl, quinolinyl, isoquinolinyl, dihydroquinolinyl, tetrahydroquinolinyl, benzodioxanyl, quinoxalinyl, quinazolinyl, naphthyridinyl, carbazolyl, tetrahydrocarbazolyl, pyridoindolyl, 1,1-dioxo-1-thia-2-aza-acenaphtene, acridinyl, phenanthridinyl, dihydrophenanthridinyl, dihydrobenzoisoquinolinyl, phenothiazinyl, dihydrodibenzooxepinyl, benzocycloheptathienyl, dihydrothienobenzothiepinyl, dihydrodibenzothiepinyl, octahydrodibenzothiepinyl, dibenzoazepinyl, dihydrodibenzoazepinyl, octahydrodibenzoazepinyl, benzocycloheptapyridyl, dihydrobenzocycloheptapyridyl, pyridobenzoazepinyl, dihydropyridobenzoazepinyl, dihydropyridobenzodiazepinyl, dihydrodibenzooxazepinyl, dihydropyridobenzooxepinyl, dihydropyridobenzooxazepinyl, dihydrodibenzothiazepinyl or dihydropyridobenzothiazepinyl.

Furthermore, their mono- or dioxo-derivatives and/or optionally their possible tautomers are also to be understood as partially hydrated heterocyclic ring systems, i.e. for example the residues of indolinone, isatin, of benzoxazolone and/or its tautomer hydroxybenzoxazole, of benzisoxazolone, benzothiazolone, benzoisothiazolone and benzimidazolone and/or their tautomers hydroxybenzoisoxazole, hydroxybenzothiazole, hydroxybenzoisothiazole and hydroxy-benzimidazole, of indazolinone, of oxazolopyridinones, thiazolopyridinones, pyrazolopyridinones and imidazo-pyridinones and/or their tautomers hydroxyoxazolopyridines, hydroxythiazolopyridines, hydroxypyrazolopyridines and hydroxyimidazopyridine, the residues of chromanone, chromone, uinolinone, dihydroquinolinone, tetrahydrocarbazolone, acridone, phenanthridone, benzoisoquinolinone of dihydrodibenzooxepinones, benzocycloheptathiophenones, dihydrothienobenzothiepinones, dihydrodibenzothiepinones, dihydrodibenzoazepinones, benzocycloheptapyridinones, dihydropyridobenzoxazepinones, dihydropyridobenzodiazepinones, dihydropyridobenzooxazepinones, dihydrodibenzothiazepinones and of dihydropyridobenzo-thiazepinones.

Saturated and unsaturated, four- to seven-membered heterocycles which can contain one or two hetero-atoms selected from N and/or S and/or O, are for example azetidine, pyrrolidine, piperidine, (1H)-tetrahydropyridine, hexahydroazepine, (1H)-tetrahydroazepine, pyrazolidine, piperazine, morpholine, thiomorpholine thiomorpholin-1,1-dioxide, hexahydrodiazepine or hexahydrooxazepine.

Anellated bi- or tricyclic, aromatic or partially hydrated heterocyclic ring systems with 8 to 16 ring atoms and at least one aromatic ring (as the group —NR$^8$R$^9$) which, aside from the essential nitrogen atom, can optionally contain one or two further hetero-atoms, selected from N and/or S and/or O, are for example indoline, isoindoline, (1H)-dihydroquinoline, (1H)-tetrahydroquinoline, (2H)-tetrahydroisoquinoline, (1H)-tetrahydroquinoxaline, (4H)-dihydrobenzooxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indole, (10H)-dihydroacridine, (10H)-dihydrophenanthridine, 1,2,3,4-tetrahydroacridanone, (10H)-phenoxazine, (10H)-phenothiazine, (5H)-dibenzoazepine, (5H)-dihydrodibenzoazepine, (5H)-octahydrodibenzoazepine, dihydrobenzo[d,e]isoquinoline, (5H)-dihydrodibenzodiazepine, (5H)-benzo[b]-pyrido[f]azepine, (5H)-dihydrobenzo[b]pyrido[f]azepine, (11H)-di-hydrodibenzo[b,e]oxazepine, (11H)-dihydrodibenzo[b,e]-thiazepine, (10H)-dihydrodibenzo[b,f]oxazepine, (10H)-dihydrodibenzo[b,f]-thiazepine, (5H)-tetrahydrodibenzoazocine, (11H)-dihydrobenzo[e]-pyrido[b]-1,4-diazepin-6-one or (11H)-dihydrobenzo[b]pyri-do[e]-1,4-diazepin-5-one.

Concretely, the invention relates to new pyridylalkane, pyridylalkene and pyridylalkine acid amides of the general formula (I)

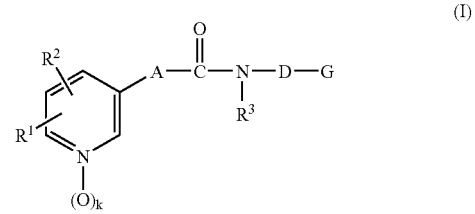

wherein the substituents have the following meanings:
R$^1$ is selected from
   hydrogen, halogen, cyano, alkyl, alkenyl, alkinyl, fluoroalkyl such as trifluoromethyl, cycloalkyl, hydroxyalkyl, hydroxy, alkoxy, cycloalkyloxy, aralkyloxy such as benzyloxy, alkanoyloxy, alkylthio, alkoxycarbonyl, aminocarbonyl, alkylaminocarbonyl, dialkylaminocarbonyl, carboxy, aryl such as phenyl, aryloxy such as phenoxy, arylthio such as phenylthio, heteroaryloxy such as pyridyloxy, heteroarylthio such as pyridylthio, and NR$^4$R$^5$, whereby
R$^4$ and R$^5$ are selected independently of each other from
   hydrogen, alkyl, alkenyl, alkinyl, aralkyl such as benzyl and aryl such as phenyl;
R$^2$ is selected from
   hydrogen, halogen, cyano, alkyl, fluoroalkyl such as trifluoromethyl, hydroxy, alkoxy and aralkyloxy such as benzyloxy;
R$^3$ is selected from
   hydrogen, alkyl, alkenyl, alkinyl, hydroxy, alkoxy and aralkyloxy such as benzyloxy;
k is the number 0 or 1,
A is selected from
   alkylene, optionally substituted one to three-fold by alkyl, hydroxy, alkoxy, fluorine, or aryl such as phenyl;
   alkylene, wherein a ethylene unit is isosterically replaced by O, S, NR$^6$, CO, SO or SO$_2$, whereby, with the exception of CO, the isosteric substitution cannot be adjacent to the amide group and R$^6$ is hydrogen, alkyl, alkenyl, acyl or alkanesulfonyl;
   1,2-cyclopropylene;

alkenylene, optionally substituted once or twice by alkyl, hydroxy, alkoxy, fluorine, cyano or aryl such as phenyl;

alkadienylene, optionally substituted once or twice by alkyl, fluorine, cyano or aryl such as phenyl;

1,3,5-hexatrienylene, optionally substituted by alkyl, fluorine, cyano or aryl such as phenyl; and ethinylene D is selected from alkylene with at least 3 carbon atoms, optionally substituted once or twice by alkyl, hydroxy, alkoxy or aryl such as phenyl;

alkenylene with at least 3 carbon atoms or alkadienylene with at least 5 carbon atoms, optionally substituted once or twice by alkyl, hydroxy, alkoxy or aryl such as phenyl;

alkinylene with at least 3 carbon atoms or alkeninylene, with at least 5 carbon atoms, optionally substituted once or twice by alkyl, hydroxy, alkoxy or aryl such as phenyl; as well as alkylene, alkenylene or alkinylene each with at least 3 carbon atoms, wherein one to three methylene units, with the exception of the (G)-terminal methylene group, are isosterically replaced by O, S, $NR^7$, CO, SO or $SO_2$, whereby $R^7$ is synonymous with $R^6$, but is selected independently thereof;

G is selected from G1, G2, G3, G4, G5 or G6 with the proviso that G must contain at least one aromatic ring, whereby $G^1$ has the meaning

   (G1)

whereby m is the number 0 or 1, and $R^8$ is selected from aralkyl such as benzyl or diphenylmethyl, aryl such as phenyl;

monocyclic aromatic five- or six-membered heterocycles, which can contain one to three hetero-atoms selected from N and/or S and/or O and are either bound directly or over a methylene group;

anellated bi- and tricyclic aromatic or partially hydrated carbocyclic ring systems with 8 to 18 ring atoms and at least one aromatic ring, whereby the linkage can occur either over an aromatic or a hydrated ring and either directly or over a methylene group; anellated bi- and tricyclic aromatic or partially hydrated heterocyclic ring systems with 8 to 18 ring atoms and at least one aromatic ring, whereby one to three ring atoms can be selected from N and/or S and/or and the linkage can occur either over an aromatic or a hydrated ring and either directly or over a methylene group;

$R^9$ is selected from hydrogen, alkyl, alkenyl, alkinyl, cycloalkyl; aralkyl such as benzyl, aryl such as phenyl; saturated or unsaturated, four- to six-membered heterocycles, which can contain one or two hetero-atoms selected from N and/or S and/or O;

monocyclic aromatic five- or seven-membered heterocycles, which can contain one to three hetero-atoms selected from N and/or S and/or O and are either bound directly or over a methylene group; anellated bi- and tricyclic aromatic or partially hydrated carbocyclic ring systems with 8 to 18 ring atoms and at least one aromatic ring, whereby the linkage can occur either over an aromatic or a hydrated ring and either directly or over a methylene group; anellated bi- and tricyclic aromatic or partially hydrated heterocyclic ring systems with 8 to 18 ring atoms and at least one aromatic ring, whereby one to three ring atoms can be selected from N and/or S and/or and the linkage can occur either over an aromatic or a hydrated ring and either directly or over a methylene group;

$R^{10}$ is synonymous with $R^9$, but can be selected independently thereof, and also hydroxy;

$G^2$ is the grouping

   (G2)

which is bound to D by means of a double bond, wherein $R^8$ and $R^9$ have the above meaning, or whereby this grouping $=CR^8R^9$ can also be a ring system bound over the carbon atom, selected from anellated bi- and tricyclic partially hydrated carbocyclic ring systems with 8 to 18 ring atoms and at least one aromatic ring;

anellated bi- and tricyclic partially hydrated hetero-cyclic ring systems with 8 to 18 ring atoms and at least one aromatic ring, whereby one to three ring atoms can be selected from N and/or S and/or O;

$G^3$ is selected from

   (G3a)

or

   (G3b)

whereby m and the substituents $R^8$, $R^9$ and $R^{10}$ can have above meanings, and n is the number 0, 1 or 2, X has the meaning $NR^{11}$, O or S, whereby $R^{11}$ has the same meaning as $R^4$, but is selected independently thereof, or the grouping $—NR^8R^9$ can also be a nitrogen heterocycle bound over the nitrogen atom, selected from anellated bi- and tricyclic aromatic or partially hydrated heterocyclic ring systems with 8 to 18 ring atoms and at least one aromatic ring, which, aside from the essential nitrogen atom, can contain 1 or 2 further hetero-atoms selected from N and/or S and/or O; and $G^4$ is selected from

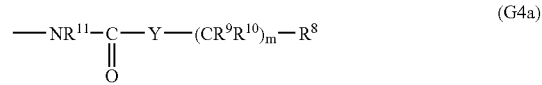   (G4a)

or

   (G4b)

with the proviso, that the structural element D—G cannot contain a total of more than 1 amide grouping (>N—CO—C← or →C—CO—N<), whereby m and the substituents $R^8$, $R^9$, $R^{10}$, $R^{11}$ and the grouping $NR^8R^9$ can have the above defined meanings with the proviso that the residues

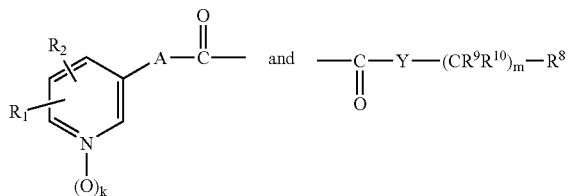

cannot be identical, and
Y is selected from
methylene, ethylene, ethenylene, cycloalkylene or represent a bond, and
Z has the meaning O or S;
$G^5$ has the meaning $$—NR^{11}—SO_2—R^{12} \quad (G5)$$

wherein $R^{11}$ has the above meaning, and
$R^{12}$ is selected from
alkyl, aryl such as phenyl;
monocyclic aromatic five- or six-membered heterocycles, which can contain one to three hetero-atoms selected from N and/or S and/or O;
anellated bi- and tricyclic aromatic or partially hydrated carbocyclic ring systems with 8 to 18 ring atoms and at least one aromatic ring, whereby the linkage can occur either over an aromatic or a hydrated ring;
anellated bi- and tricyclic aromatic or partially hydrated heterocyclic ring systems with 8 to 18 ring atoms and at least one aromatic ring, whereby one to three ring atoms can be selected from N and/or S and/or O and the linkage can occur either over an aromatic or a hydrated ring;
$G^6$ is selected from

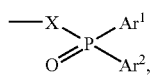

wherein X can have the above meanings and
$Ar^1$ and $Ar^2$ are selected independently from each other from
aryl such as phenyl or naphthyl as well as heteroaryl such as pyridyl;

and whereby aromatic ring systems in the substituents $R^1$, $R^2$, $R^3$, $R^4$, $R^5$, $R^8$, $R^9$, $R^{10}$, $R^{11}$, $R^{12}$, $Ar^1$ and $Ar^2$ and/or in ring systems $=CR^8R^9$ and $—NR^8R^9$ can be substituted independently from each other by one to three of the same or different groups selected from halogen, cyano, alkyl, fluoroalkyl such as trifluoromethyl, cycloalkyl, aralkyl such as benzyl, aryl such as phenyl, hydroxy, hydroxyalkyl, alkoxy, alkoxy entirely or partially substituted by fluorine, aralkyloxy such as benzyloxy, aryloxy such as phenoxy, mercapto, alkylthio, arylthio such as phenylthio, sulfo, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino and, for two adjacent residues on the aromatic ring, methylenedioxy and whereby alkyl- and cycloalkyl residues in the group G can be substituted by one or two of the same or different residues selected from hydroxy, carboxy, alkoxycarbonyl, aralkyloxycarbonyl such as benzyloxycarbonyl, amino, mono-alkylamino and di-(alkyl)amino;

the cis- and trans-isomers as well as E- and Z-isomers of the above defined compounds, especially in the case that A is a cyclopropane ring or D contains one or more double bonds, including the enantiomers, diastereomers and other isomers of the above defined compounds, optionally in pure form or as their racemic and/or non-racemic mixtures;

the tautomers of the above defined compounds, in the optinal case that G represents a heterocyclic aromatic ring or one which simultaneously contains substitutions by free hydroxy-, mercapto- or amino groups; as well as the corresponding acid addition salts of the compounds defined above including their hydrates and solvates.

According to a preferred embodiment, the invention relates to new pyridylalkane, pyridylalkene and pyridylalkine acid amides of the formula (I)

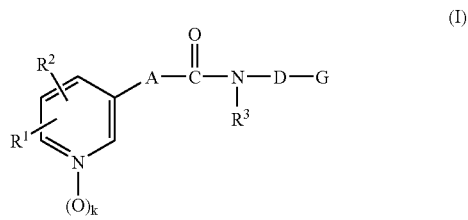

wherein the substituents have the following meanings:
$R^1$ is selected from
hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridyl thio, and $NR^4R^5$, whereby
$R^4$ and $R^5$ are selected independently of each other from
hydrogen, $C_1$-$C_6$-alkyl, $C_3$-$C_6$-alkenyl, $C_3$-$C_6$-alkinyl, benzyl and phenyl;
$R^2$ is selected from
hydrogen, halogen, cyano, $C_1$-$C_6$-Alkyl, trifluoromethyl, hydroxy, $C_1$-$C_6$-alkoxy and benzyloxy;
$R^3$ is selected from
hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;
k is 0 or 1,
A is selected from
$C_1$-$C_6$-alkylene, optionally substituted one to three-fold by $C_1$-$C_3$-alkyl, hydroxy, $C_1$-$C_3$-alkoxy, fluorine, or phenyl;
$C_2$-$C_6$-alkylene, in which a methylene unit is isosterically replaced by O, S, $NR^6$, CO, SO or $SO_2$, whereby, with the exception of CO, the isosteric substitution cannot be adjacent to the amide group and $R^6$ is selected from hydrogen, $C_1$-$C_6$-alkyl, $C_3$-$C_6$-alkenyl, $C_1$-$C_6$-Acyl or $C_1$-$C_6$-alkanesulfonyl;
1,2-cyclopropylene;
$C_2$-$C_6$-alkenylene, optionally substituted once or twice by $C_1$-$C_3$-alkyl, hydroxy, $C_1$-$C_3$-alkoxy, fluorine, cyano or phenyl;

C$_4$-C$_6$-alkadienylene, optionally substituted once or twice by C$_1$-C$_3$-alkyl, fluorine, cyano or phenyl;
1,3,5-hexatrienylene, optionally substituted by C$_1$-C$_3$-alkyl, fluorine, cyano or phenyl; as well as ethinylene D is selected from
   C$_3$-C$_{12}$-alkylene, optionally substituted once or twice by C$_1$-C$_6$-alkyl, hydroxy, C$_1$-C$_6$-alkoxy or phenyl;
   C$_3$-C$_{12}$-alkenylene or C$_5$-C$_{12}$-alkadienylene, optionally substituted one or twice by C$_1$-C$_6$-alkyl, hydroxy, C$_1$-C$_6$-alkoxy or phenyl;
   C$_3$-C$_{12}$-alkinylene or C$_5$-C$_{12}$-alkeninylene, optionally substituted one or twice by C$_1$-C$_6$-alkyl, hydroxy, C$_1$-C$_6$-alkoxy or phenyl; and
   C$_3$-C$_{12}$-alkylene, C$_3$-C$_{12}$-alkenylene or C$_3$-C$_{12}$-alkinylene, wherein, with the exception of the (G)-terminal methylene group, one to three methylene units are isosterically replaced by O, S, NR$^7$, CO, SO or SO$_2$, whereby R$^7$ is synonymous with R$^6$, but is selected independently thereof;

G is selected from G1, G2, G3, G4, G5 or G6 with the proviso that G must contain at least one aromatic ring, whereby G$^1$ has the meaning $$-(CR^9R^{10})_m-R^8 \qquad (G1)$$

and
m is 0 or 1,
R$^8$ is selected from
   benzyl, diphenylmethyl, phenyl;
   monocyclic aromatic five- or six-membered heterocycles, which can contain one to three hetero-atoms selected from N and/or S and/or O and are either bound directly or over a methylene group;
   anellated bi- and tricyclic aromatic or partially hydrated carbocyclic ring systems with 8 to 18, especially with up to 16 ring atoms, and at least one aromatic ring, whereby the linkage can occur either over an aromatic or a hydrated ring and either directly or over a methylene group;
   anellated bi- and tricyclic aromatic or partially hydrated heterocyclic ring systems with 8 to 18, especially with up to 16 ring atoms, and at least one aromatic ring, whereby one to three ring atoms can be selected from N and/or S and/or O and the linkage can occur either over an aromatic or a hydrated ring and either directly or over a methylene group;
R$^9$ is selected from
   hydrogen, C$_1$-C$_6$-alkyl, C$_3$-C$_6$-alkenyl, C$_2$-C$_6$-alkinyl, C$_3$-C$_8$-cycloalkyl;
   benzyl, phenyl;
   saturated or unsaturated, four- to seven-membered heterocycles, which can contain one or two hetero-atoms selected from N and/or S and/or O;
   monocyclic aromatic five- or six-membered heterocycles, which can contain one to three hetero-atoms selected from N and/or S and/or O and are either bound directly or over a methylene group;
   anellated bi- and tricyclic aromatic or partially hydrated carbocyclic ring systems with 8 to 18, especially with up to 16 ring atoms, and at least one aromatic ring, whereby the linkage can occur either over an aromatic or a hydrated ring and either directly or over a methylene ground;
   anellated bi- and tricyclic aromatic or partially hydrated heterocyclic ring systems with 8 to 18, especially with up to 16 ring atoms, and at least one aromatic ring, whereby one to three ring atoms can be selected from N and/or S and/or O and the linkage can occur either over an aromatic or a hydrated ring and either directly or over a methylene group;

R$^{10}$ is synonymous with R$^9$, but is selected independently thereof, or can be hydroxy;
G$^2$ is the grouping $$=CR^8R^9 \qquad (G2)$$

which is bound to D by means of a double bond,
   wherein R$^8$ and R$^9$ have the above meaning or whereby the grouping =CR$^8$R$^9$ can also be a ring system bound over the carbon atom, selected from
   anellated bi- and tricyclic partial hydrated carbocyclic ring systems with 8 to 18, especially up to 16 ring atoms, and at least an aromatic ring;
   anellated bi- and tricyclic partially hydrated hetero-cyclic ring systems with 8 to 18, especially up to 16 ring atoms, and at least one aromatic ring, whereby one to three ring atoms can be selected from N and/or S and/or O;
G$^3$ is selected from $$-X-(CH_2)_n-(CR^9R^{10})_m-R^8 \qquad (G3a)$$

or $$-NR^8R^9 \qquad (G3b)$$

whereby m and the substituents R$^8$, R$^9$ and R$^{10}$ can have the above meanings, and
n is the number 0, 1 or 2
X has the meanings NR$^{11}$, O or S, whereby
R$^{11}$ has the same meanings as R$^4$, but is selected independently thereof, or the grouping —NR$^8$R$^9$ can also be a nitrogen heterocycle bound over the nitrogen atom, selected from
   anellated bi- and tricyclic aromatic or partially hydrated heterocyclic ring systems with 8 to 16 ring atoms and at least an aromatic ring, which, aside from the essential nitrogen atom, can contain 1 or 2 further hetero-atoms selected from N, and/or S and/or O; and
G$^4$ is selected from $$-NR^{11}-\underset{\underset{O}{\|}}{C}-Y-(CR^9R^{10})_m-R^8 \qquad (G4a)$$

with the proviso that the structural element D—G cannot contain a total of more than 1 amide grouping (>N—CO—C← or →C—CO—N<), whereby m and the substituents R$^8$, R$^9$, R$^{10}$, R$^{11}$ and the grouping NR$^8$R$^9$ can have the above meaning with the proviso that the residues

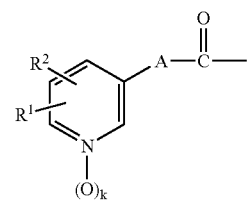

cannot be identical, and

Y is selected from
  methylene, ethylene, ethenylene, $C_3$-$C_7$-cycloalkylene or represents a bond, and
Z is O or S;
$G^5$ has the meaning $$—NR^{11}—SO_2—R^{12} \qquad (G5)$$

wherein $R^{11}$ has the above meaning, and
$R^{12}$ is selected from
  $C_1$-$C_6$-alkyl, phenyl;
  monocyclic aromatic five- or six-membered heterocycles, which can contain one to three hetero-atoms selected from N and/or S and/or O;
  anellated bi- and tricyclic aromatic or partially hydrated carbocyclic ring systems with 8 to 18, especially up to 16 ring atoms, and at least an aromatic ring, whereby the linkage can occur either over an aromatic or a hydrated ring;
  anellated bi- and tricyclic aromatic or partially hydrated heterocyclic ring systems with 8 to 18 ring atoms, especially up to 16 ring atoms, and at least one aromatic ring, whereby one to three ring atoms can be selected from N and/or S and/or O and the linkage can occur either over an aromatic or a hydrated ring;
$G^6$ is selected from (G6)

wherein x can have the above meanings and $Ar^1$ and $Ar^2$ are selected independently of each other from phenyl, pyridyl or naphthyl;

and whereby aromatic ring systems in the substituents $R^1$, $R^2$, $R^3$, $R^4$, $R^5$, $R^8$, $R^9$, $R^{10}$, $R^{11}$, $R^{12}$, $Ar^1$ and $Ar^2$ and/or in ring systems $=CR^8R^9$ and $—NR^8R^9$ can be substituted independently from each other by one to three of the same or different groups selected from halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C^6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy and whereby alkyl and cycloalkyl residues in the Group G can be substituted by one or two of the same or different groups, selected from hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;

the cis- and trans-isomers, E- and Z-isomers of the above defined compounds, especially in the case that A is a cyclopropane ring or D contains one or more double bonds, including the corresponding enantiomers, diastereomers and other isomers of the above defined compounds, optionally in pure form or as their racemic and/or non-racemic mixtures;

the tautomers of the above defined compounds, in the optional case that G represents or contains a heterocyclic aromatic ring with simultaneous substitution by the hydroxy-, mercapto- or amino groups; as well as the corresponding acid addition salts of the compounds defined above including their hydrates and solvates.

According to a further, particularly preferred embodiment, the invention relates to new compounds according to the general formula (I)

(I)

wherein the substituents have the following meaning:
$R^1$ is selected from
  hydrogen, halogen, cyano, $C_1$-$C_6$-alkyl, trifluoromethyl, ethinyl, hydroxy, $C_1$-$C_4$-alkoxy, benzyloxy, $C_1$-$C_4$-alkyl-thio, $C_2$-$C_5$-alkoxycarbonyl, aminocarbonyl, $C_3$-$C_9$-dialkylaminocarbonyl, carboxy, phenoxy, phenylthio and pyridyloxy;
$R^2$ is selected from
  hydrogen, fluorine, chorine, bromine, $C_1$-$C_4$-alkyl, trifluoromethyl, hydroxy, $C_1$-$C_4$-alkoxy;
$R^3$ is selected from
  hydrogen, $C_1$-$C_3$-alkyl, alkyl, hydroxy, $C_1$-$C_3$-alkoxy and benzyloxy;
k is 0 or 1,
A is selected from
  $C_1$-$C_6$-alkylene, optionally substituted once or twice by $C_1$-$C_3$-alkyl, hydroxy, fluorine or phenyl;
  $C_2$-$C_6$-alkylene, wherein a methylene unit is isosterically replaced by O, S, NH, N($CH_3$) or CO, hereby, with the exception of CO, the isosteric substitution cannot be adjacent to the amide group, and
  1,2-cyclopropylene;
  $C_2$-$C_6$-alkenylene, optionally substituted once or twice by $C_1$-$C_3$-alkyl, phenyl, hydroxy and/or fluorine;
  $C_4$-$C_6$-Alkadienylene, optionally substituted once or twice by methyl or fluorine;
  1,3,5-hexatrienylene, optionally substituted by methyl or fluorine, and
  ethinylene
D is selected from
  $C_3$-$C_{12}$-alkylene, optionally substituted once or twice by $C_1$-$C_3$-alkyl, hydroxy or phenyl;
  $C_3$-$C_{12}$-alkenylene, optionally substituted once or twice by $C_1$-$C_3$-alkyl, hydroxy or phenyl;
  $C_3$-$C_{12}$-alkinylene, optionally substituted once or twice by $C_1$-$C_3$-alkyl, hydroxy or phenyl, and
  $C_3$-$C_{12}$-alkylene, $C_3$-$C_{12}$-alkenylene or $C_3$-$C_{12}$-alkinylene, wherein one to three methylene units are isosterically replaced by O, S, NH, N($CH_3$), N($COCH_3$), N($SO_2CH_3$), CO or $SO_2$;
G is selected from G1, G2, G3, G4, G5 or G6 with the proviso that G must contain at least one aromatic ring, whereby
$G^1$ has the meaning $$—(CR^9R^{10})_m—R^8 \qquad (G1)$$

whereby m is the number 0 or 1,

R$^8$ is selected from benzyl, diphenylmethyl, phenyl;

benzocyclobutyl, indanyl, indenyl, oxoindanyl, naphthyl, dihydronaphthyl, tetrahydronaphthyl, biphenylenyl, fluoroenyl, oxofluoroenyl, anthryl, dihydroanthryl, oxodihydroanthryl, dioxodihydroanthryl, phenanthryl, dibenzocycloheptenyl, dihydrodibenzocycloheptenyl, oxodihydrodibenzocycloheptenyl, dihydrodibenzocyclooctenyl or tetrahydrodibenzocyclooctenyl, bound directly or over a methylene group;

furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, dihydrobenzofuryl, benzothienyl, dihydrobenzothienyl, indolyl, indolinyl, isoindolinyl, oxoindolinyl, dioxoindolinyl, benzooxazolyl, oxobenzooxazolinyl, benzoisoxazolyl, oxobenzoisoxazolinyl, benzothiazolyl, oxobenzothiazolinyl, benzoisothiazolyl, oxobenzoisothiazolinyl, benzoimidazolyl, oxobenzoimidazolinyl, indazolyl, oxoindazolinyl, benzofurazanyl, benzothiadiazolyl, benzotriazolyl, oxazolopyridvl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinolyl, isoquinolinyl, dihydroquinolinyl, oxodihydroquinolinyl, tetrahydroquinolinyl, oxotetrahydroquinolinyl, benzodioxanyl, quinoxalinyl, quinazolinyl, naphthyridinyl, carbazolyl, tetrahydrocarbazolyl, pyridoindolyl, 1,1-dioxo-1-thia-2-aza-acenaphthenyl, acridinyl, oxodihydroacridinyl, phenanthridinyl, oxodihydrophenanthridinyl, dihydrobenzoisochinolinyl, oxodihydrobenzosoquinolinyl, phenothiazinyl, dihydrodibenzooxepinyl, oxodihydrodibenzooxepinyl, benzocyclcheptathienyl, oxobenzocycloheptathienyl, dihydrothienobenzothiepinyl, oxodihydrothienobenzothiepinyl, dihydrodibenzothiepinyl, oxodihydrodibenzothiepinyl, octahydrodibenzothiepinyl, dibenzoazepinyl, dihydrodibenzoazepinyl, oxodihydrodibenzoazepinyl, octahydrodibenzoazepinyl, benzocycloheptapyridyl, oxobenzocycloheptapyridyl, pyridobenzoazepinyl, dihydropyridobenzoazepinyl, oxodihydropyridobenzoazepinyl, dihydropyridobenzo-diazepinyl, oxodihydropyridobenzodiazepinyl, dihydrodibenzooxazepinyl, dihydropyridobenzooxepinyl, dihydropyridobenzooxazepinyl, oxodihydropyridobenzo-oxazepinyl, dihydrodibenzothiazepinyl, oxodihydrodibenzothiazepinyl, dihydropyridobenzo-thiazepinyl or oxodihydropyridobenzothiazepinyl, bound directly or over a methylene group;

R$^9$ is selected from hydrogen, $C_1$-$C_6$-alkyl, $C_3$-$C_6$-alkenyl, $C_2$-$C_6$-alkinyl, $C_3$-$C_8$-cycloalkyl;

benzyl, phenyl;

azetidinyl, tetrahydrofuryl, tetrahydrothienyl, pyrrolidinyl, tetrahydropyridinyl, piperidinyl, hexahydroazepinyl, piperazinyl, morpholinyl or hexahydrodiazepinyl;

furyl, thienyl, pyrrolyl, oxazolyl, isoxazolyl, thiazolyl, iso-thiazolyl, pyrazolyl, imidazolyl, oxadiazolyl, thiadiazolyl, triazolyl, pyridyl, triazinyl, bound directly or over a methylene group indanyl, indenyl, oxoindanyl, naphthyl, dihydronaphthyl, tetrahydronaphthyl, biphenylenyl, fluoroenyl, oxofluoroenyl, anthryl, dihydroanthryl, oxodihydroanthryl, phenanthryl, dibenzocycloheptenyl, dihydrodibenzocycloheptenyl, oxodihydrodibenzo-cycloheptenyl, bound directly or over a methylene group;

benzofuryl, benzothienyl, indolyl, indolinyl, isoindolinyl, oxoindolinyl, dioxoindolinyl, benzooxazolyl, oxobenzooxazolinyl, benzoisoxazolyl, oxobenzoisoxazolinyl, benzothiazclyl, oxobenzothiazolinyl, benzoisothiazolyl, oxobenzoiso-thiazolinyl, benzoimidazolyl, oxobenzoimidazolinyl, indazolyl, oxoindazolinyl, benzothiadiazolyl, benzotriazolyl, oxazolopyridyl, thiazolopyridyl, isothiazolopyridyl, imidazopyridyl, quinolinyl, isoquinolinyl, oxodihydroquinolinyl, tetrahydroquinolinyl, oxotetrahydroquinolinyl, carbazolyl, pyridoindolyl, dihydrobenzoisoquinolinyl, phenothiazinyl, bound directly or over a methylene group;

R$^{10}$ is synonymous with R$^9$, but is selected independently thereof, or is hydroxy;

G$^2$ is the grouping $$=CR^8R^9 \qquad (G2)$$

which is bound to D over a double bond, wherein R$^8$ and R$^9$ have the above meaning, or whereby the grouping =CR$^8$R$^9$ can also be a ring system bound over the carbon atom, selected from indanyl, indenyl, tetrahydronaphthyl, fluoroenyl, dihydroanthryl, tetrahydrobenzocycloheptenyl, dibenzocycloheptenyl, dihydrodibenzocyclohectenyl; indolinyl, isoindolinyl, oxoindolinyl, tetrahydroquinolinyl, tetrahydroisoquinolinyl, dihydroacridinyl, dihydrodibenzooxepinyl, dihydrothienobenzothiepinyl, dihydrodibenzothiepinyl, dibenzoazepinyl, dihydrodibenzoazepinyl, benzocycloheptapyridinyl, dihydrobenzo-cycloheptapyridinyl, pyridobenzoazepinyl, dihydropyrido-benzoazepinyl, oxodihydropyrido-benzooxepinyl, dihydropyridobenzothiepinyl;

G$^3$ is selected from $$-X-(CH_2)_n-(CR^9R^{10})_m-R^8 \qquad (G3a)$$

or $$-NR^8R^9 \qquad (G3b)$$

whereby m and the substituen's R$^8$, R$^9$ and R$^{10}$ can have the above defined meanings and n is the number 0 or 1, X has the meaning NR$^{11}$, O or S, whereby R$^{11}$ is selected from hydrogen, $C_1$-$C_3$-alkyl, allyl, propinyl, benzyl and phenyl, or the grouping —NR$^8$R$^9$ can also be a nitrogen heterocycle bound over the nitrogen atom, selected from indoline, isoindoline, (1H)-dihydroquinoline, (1H)-tetrahydroquinoline, (2H)-tetrahydroisoquinoline, (4H)-dihydrobenzooxazine, (4H)-dihydrobenzothiazine, (1H)-tetrahydrobenzo[b]azepine, (1H)-tetrahydrobenzo-[c]azepine, (1H)-tetrahydrobenzo[d]azepine, (5H)-tetrahydrobenzo[b]oxazepine, (5H)-tetrahydrobenzo-[b]thiazepine, 1,2,3,4-tetrahydro-9H-pyrido[3,4-b]indole, carbazole, tetrahydrocarbazole, 1,1-dioxo-1-thia-2-aza-acenaphthene, (10H)-dihydroacridine, (10H)-dihydrophenanthridine, 1,2,3,4-tetrahydroacridanone, (10H)-phenoxazine, (10H)-phenothiazine, dihydrobenzo[d,e]iso-quinoline, (5H)-dibenzoazepine, (5H)-dihydrodibenzoazepine, (5H)-octahydrodi-benzoazepine, (5H)- dihydrodibenzodiazepine, (5H)-benzo[b]pyrido[f]azepine, (5H)-dihydrobenzo[b]pyrido-[f]azepine, (11H)-dihydrodibenzo[b,e]oxazepine, (11H)-dihydrodibenzo[b,e]thiazepine, (10H)-dihydrodibenzo-[b,f]oxazepine, (10H)-dihydrodibenzo[b,f]thiazepine, (5H)-tetrahydrodibenzoazocine, (11H)-dihydrobenzo[e]pyrido[b]-1,4-diazepin-6-one or (11H)-dihydrobenzo[b]pyrido[e]-1,4-diazepin-5-one;

$G^4$ is selected from

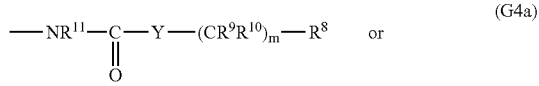

(G4a)

(G4b)

with the proviso that the structural element D—G cannot contain a total of more than 1 amide grouping (>N—CO—C← or →C—CO—N<), whereby m and the substituents $R^8$, $R^9$, $R^{10}$, $R^{11}$ and the grouping $NR^8R^9$ can have the above meanings with the proviso that the residues

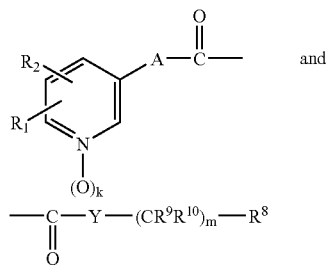

and cannot be identical, and

Y is selected from
 methylene, ethylene, ethenylene, cyclopropylene or represents a bond, and Z has the meaning O or S;

$G^5$ has the meaning

(G5)

wherein $R^{11}$ has the above meaning, and
$R^{12}$ is selected from
 phenyl, indenyl, naphthyl, anthryl;
 furyl, thienyl, thiazolyl, pyridyl, indolyl, benzothienyl or quinolinyl;

$G^6$ is selected from

(G6)

wherein X can have the above meanings and $Ar^1$ and $Ar^2$ are selected independently of each other from phenyl, pyridyl or naphthyl;

and whereby aromatic ring systems in the substituents $R^1$, $R^3$, $R^8$, $R^9$, $R^{10}$, $R^{11}$, $R^{12}$, $Ar^1$ and $Ar^2$ and/or in ring systems =$CR^8R^9$ and —$NR^8R^9$ can be substituted independently from each other by one to three of the same or different groups selected from halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-Alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy and whereby allyl and cycloalkyl residues in the Group G can be substituted by one or two of the same or different residues, selected from hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino.

According, to a very particular embodiment the invention relates to compounds according to the general formula (I)

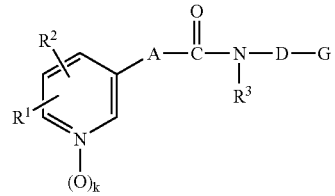

(I)

wherein the substituents have the following meanings:

$R^1$ is selected from
 hydrogen, fluorine, chlorine, bromine, methyl, ethyl, trifluoromethyl, hydroxy, $C_1$-$C_4$-alkoxy, phenoxy, methylthio, ethylthio, methoxycarbonyl, aminocarbonyl and carboxy;

$R^2$ is selected from
 hydrogen, chlorine, methyl, hydroxy and methoxy;

$R^3$ is hydrogen;

k is 0,

A is selected from
 $C_2$-$C_6$-alkylene, optionally substituted once or twice by hydroxy or fluorine;
 $C_2$-$C_6$-alkylene, wherein a methylene unit is isosterically replaced by O, S, or CO, whereby, with the exception of CO, the isosteric substitution cannot be adjacent to the amide group;
 $C_2$-$C_6$-alkenylene, optionally substituted by methyl and/or fluorine;
 $C_4$-$C_6$-alkadienylene, optionally substituted by methyl;
 ethinylene;

D is selected from
 $C_3$-$C_{10}$-alkylene, optionally substituted by methyl, hydroxy or phenyl;
 $C_3$-$C_{10}$-alkenylene, optionally substituted by methyl, hydroxy or phenyl;
 $C_3$-$C_{10}$-alkinylene, optionally substituted by hydroxy or phenyl;
 $C_3$-$C_{10}$-alkylene, $C_3$-$C_{10}$-alkenylene or $C_3$-$C_{10}$-alkinylene, wherein, respectively, a methylene unit is isosterically replaced by O, NH, N(CH$_3$), or CO, or an ethylene group is isosterically replaced by a group NH—CO and/or CO—NH, or a propylene group isosterically replaced by a group NH—CO—NH or NH—CO—O and/or O—CO—NH;

G is selected from G1, G2, G3, G4, G5 or G6 with the proviso that G must contain at least one aromatic ring, whereby $G^1$ has the meaning $$—(CR^9R^{10})_m—R^8 \qquad (G1)$$

whereby m is the number 0 or 1, $R^8$ is selected from benzyl, diphenylmethyl, phenyl;

indanyl, indenyl, oxoindanyl, naphthyl, tetrahydronaphthyl, fluoroenyl, oxofluoroenyl, anthryl, dihydroanthryl, oxodihydroanthryl, phenanthryl, dibenzocycloheptenyl, dihydrodibenzocycloheptenyl, oxodihydrodibenzocycloheptenyl, bound directly or over a methylene group;

furyl, thienyl, pyrrolyl, oxazolyl, isoxazolyl, thiazolyl, pyrazolyl, imidazolyl, thiadiazolyl, triazolyl, pyridyl, pyrazinyl, pyrimidinyl, benzofuryl, benzothienyl, indolyl, indolinyl, isoindolinyl, oxoindolinyl, benzooxazolyl, oxobenzooxazolinyl, benzoisoxazolyl, oxobenzoisoxazolinyl, benzothiazolyl, oxobenzothiazolinyl, benzoisothiazolyl, oxobenzoisothiazolinyl, benzoimidazolyl, oxobenzoimidazolinyl, benzothiadiazolyl, benzotriazolyl, oxazolopyridyl, oxodihydrooxazolopyridyl, thiazolopyridyl, isothiazolopyridyl, imidazopyridyl, oxodihydroimidazopyridyl, thienopyrimidinyl, chromanonyl, quinolyl, isoquinolinyl, oxodihydroquinolinyl, tetrahydroquinolinyl, oxotetrahydroquinolinyl, quinoxalinyl, quinazolinyl, naphthyridinyl, carbazoleyl, pyridoindolyl, 1,1-dioxo-1-thia-2-aza-acenaphthenyl, acridinyl, oxodihydroacridinyl, phenanthridinyl, dihydrobenzoisoquinolinyl, oxodihydrobenzoisoquinolinyl, dihydrodibenzooxepinyl, dibenzoazepinyl, dihydrodibenzoazepinyl, oxodihydrodibenzoazepinyl, benzocycloheptapyridyl, pyridobenzoazepinyl, dihydropyridobenzoazepinyl, dihydropyridobenzodiazepinyl, oxodihydropyridobenzodiazepinyl, dihydropyridobenzooxepinyl or dihydrodibenzothiazepinyl, bound directly or over a methylene group;

$R^9$ is selected from hydrogen, $C_1$-$C_3$-alkyl, $C_3$-$C_8$-cycloalkyl, benzyl, phenyl, indanyl, indenyl, naphthyl, anthryl;

furyl, thienyl, pyrrolyl, oxazolyl, thiazolyl, isothiazolyl, pyrazolyl, imidazolyl, thiadiazolyl, triazolyl, pyridyl, benzofuryl, benzothienyl, indolyl, benzooxazolyl, oxobenzooxazolinyl, benzoisoxazolyl, benzothiazolyl, benzoisothiazolyl, benzoimidazolyl and benzotriazolyl;

$R^{10}$ is synonymous with $R^9$, but is selected independently thereof, or can be hydroxy;

$G^2$ is the grouping $$=CR^8R^9 \qquad (G2)$$

which is bound to D over a double bond, wherein $R^8$ and $R^9$ have the above meaning, or whereby the grouping $=CR^8R^9$ can also be a ring system bound over the carbon atom, selected from indanyl, tetrahydronaphthyl, fluoroenyl, dihydroanthryl, tetrahydrobenzocycloheptenyl, dibenzocycloheptenyl, dihydrodibenzocycloheptenyl;

indolinyl, isoindolinyl, oxoindolinyl, tetrahydroquinolinyl, tetrahydroisoquinolinyl, dihydroacridinyl, dihydrodibenzooxepinyl, dihydrothienobenzothiepinyl, dihydrodibenzothiepinyl, dibenzoazepinyl, dihydrodibenzoazepinyl, benzocycloheptapyridinyl, dihydrobenzocyclohepta-pyridinyl, pyridobenzoazepinyl, dihydropyridobenzoazepinyl, oxodihydropyridobenzooxepinyl, dihydropyridobenzothiepinyl;

$G^3$ is selected from $$—X—(CH_2)_n—(CR^9R^{10})_m—R^8 \qquad (G3a)$$

or $$—NR^8R^9 \qquad (G3b)$$

whereby m and the substituents $R^8$, $R^9$ and $R^{10}$ can have the above defined meanings and n is the number 0 or 1, X has the meaning $NR^{11}$, O or S, whereby $R^{11}$ is selected from hydrogen, $C_1$-$C_3$-alkyl, benzyl and phenyl, or the grouping —$NR^8R^9$ can also be a nitrogen heterocycle bound over the nitrogen atom selected from indoline, isoindoline, (1H)-dihydroquinoline, (1H)-tetrahydroquinoline, (2H)-tetrahydroisoquinoline, (1H)-tetrahydrobenzo[b]azepine, (1H)-tetrahydrobenzo-[c]azepine, (1H)-tetrahydrobenzo[d]azepine, (5H)-tetrahydrcbenzo[b]oxazepine, (5H)-tetrahydrobenzo-[b]thiazepine, carbazole, 1,1-dioxo-1-thia-2-aza-acenaphthene, (10H)-dihydroacridine, (10H)-dihydrophenanthridine, dihydrobenzo[d,e]isoquinoline, (5H)-dihydrodibenzoazepine, (5H)-dihydrodibenzo-diazepine, (5H)-dihydrobenzo[b]pyrido[f]azepine, (11H)-dihydroben-zo[b,e]oxazepine, (11H)-dihydrodibenzo-[b,e]thiazepine, (10H)-dihydrodibenzo[b,f]oxazepine, (10H)-dihydrodibenzo[b,f]thiazepine, (5H)-tetrahydrodibenzoazocine, (11H)-dihydrobenzo [e]pyrido[b]-1,4-diazepin-6-one or (11H)-dihydrobenzo[b]pyrido[e]-1,4-diazepin-5-one;

$G^4$ is selected from $$—NR^{11}—\underset{\underset{O}{\|}}{C}—Y—(CR^9R^{10})_m—R^8 \qquad or \qquad (G4a)$$

$$—NR^{11}—\underset{\underset{Z}{\|}}{C}—NR^8R^9, \qquad (G4b)$$

with the proviso that the structural element D—G cannot contain a total of more than 1 amide grouping (>N—CO—C← or →C—CO—N<), whereby m and the substituents $R^8$, $R^9$, $R^{10}$, $R^{11}$ and the grouping $NR^8R^9$ can have the above meanings with the proviso that the residues

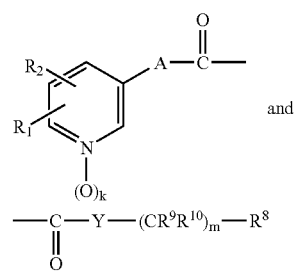

cannot be identical, and

Y is selected from
    methylene, ethenylene, or represents a bond, and
Z has the meaning O or S;
$G^5$ has the meaning

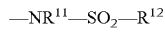 (G5)

wherein $R^{11}$ has the above meaning, and
$R^{12}$ is selected from
    phenyl, naphthyl, anthryl;
    thienyl, pyridyl, benzothienyl or quinolinyl;
$G^6$ is selected from

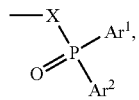 (G6)

wherein X can have the above meanings and $Ar^1$ and $Ar^2$ are selected independently of each other from phenyl, pyridyl or naphthyl;

and whereby aromatic ring systems in the substituents $R^1$, $R^3$, $R^8$, $R^9$, $R^{10}$; $R^{11}$, $R^{12}$, $Ar^1$ and $Ar^2$ and/or in ring systems =$CR^8R^9$ and —$NR^8R^9$ can be substituted independently from each other by one to three of the same or different groups selected from halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-Alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy and whereby alkyl and cycloalkyl residues in the Group G can be substituted by one or two of the same or different residues, selected from hydroxy, carboxy, $C_2$-$C_7$-alkoxycarbonyl, benzyloxycarbonyl, amino, mono-$C_1$-$C_6$-alkylamino and di-($C_1$-$C_6$-alkyl) amino.

Furthermore, according to a very particularly preferred embodiment, the invention relates to compounds according to the general formula (I)

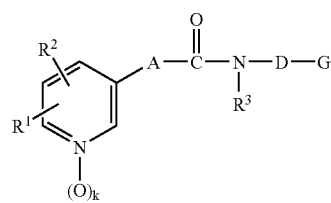 (I)

wherein the substituents have the following meanings:
$R^1$ is selected from
    hydrogen, fluorine, methyl, trifluoromethyl, ethylthio;
$R^2$ is hydrogen;
$R^3$ is hydrogen;
k is 0, A is selected from
    ethylene or butylene, optionally substituted by hydroxy or one or two fluorine atoms, or
    $OCH_2$, $SCH_2$,
    ethenylene or 1,3-butadienylene;
D is selected from
    $C_3$-$C_8$-alkylene, optionally substituted by hydroxy or phenyl;
    $C_3$-$C_8$-alkenylene, optionally substituted by phenyl, $C_3$-$C_8$-alkinylene; or
    $C_3$-$C_8$-alkylene, $C_3$-$C_8$-alkenylene or $C_3$-$C_8$-alkinylene, in which one or two methylene units are isosterically replaced by O, NH or CO;
G is selected from
    cyclopentylphenylmethylene, cyclohexylphenylmethyl, cyclohexylhydroxyphenylmethyl, diphenylmethyl, diphenylhydroxymethyl, diphenylmethylene, diphenylethyl, diphenylhydroxy ethyl, diphenylethylene, triphenylmethyl, triphenylethyl, triphenylhydroxyethyl, triphenylethylene, naphthylmethylene, naphthyl, tetrahydronaphthyl, hydroxytetrahydronaphthyl, tetrahydronaphthylidene, fluoroenyl, hydroxyfluoroenyl, fluoroenylidene, tetrahydrobenzocycloheptenyl, hydroxytetrahydrobenzocycloheptenyl, tetrahydrobenzocycloheptenylidene, dihydrodibenzocycloheptenyl, hydroxydihydrodibenzo-cycloheptenyl, dihydrodibenzocycloheptenylidene;
    phenyl-thienylmethyl, phenyl-thienylhydroxymethyl, phenyl-thienylmethylene, dithienylmethyl, dithienylhydroxymethyl, dithienylmethylene, phenyl-furylmethyl, phenyl-furyl-hydroxymethyl, phenyl-furylmethylene, phenyl-pyridylmethyl, phenyl-pyridylhydroxymethyl, phenyl-pyridylmethylene;
    tetrahydroquinolinyl, tetrahydroisoquinolinyl, benzocycloheptapyridinyl, benzocycloheptapyridinylidene, dihydrobenzocycloheptapyridinyl, dihydrobenzocycloheptapyridinylidene, dihydrodibenzooxepinyl, dihydrodibenzooxepinylidene, dihydrodibenzothiepinyl, dihydrodibenzothiepinylidene;
    phenylpyrrolyl, diphenylpyrrolyl, phenylthienyl, diphenyl-thienyl, phenylpyrazolyl, diphenylpyrazolyl, phenylimidazolyl, diphenylimidazolyl, phenylpyridyl, diphenylpyridyl, indolyl, oxoindolinyl, benzoimidazolyl, oxobenzoimidazolyl, benzothiazolyl, oxobenzothiazolyl, benzoisothiazolyl, benzooxazolyl, oxobenzooxazolyl, benzotriazolyl;
    diphenylmethylamino, diphenylmethyl-methylamino, dibenzylamino, benzylphenylamino, cyclohexylphenylamino, triphenylmethylamino, biphenylylamino, diphenylamino; N-indolinyl, N-isoindolinyl, N-tetrahydroquinolinyl, N-tetrahydrobenzazepinyl, N-phenyl-tetrahydrobenzoazepinyl, N-1,1-dioxo-1-thia-2-aza-acenaphthenyl, N-1H,3H-benzo[de]-isoquinolinyl, N-dihydrodibenzoazepinyl; diphenylmethyloxy, diphenylmethylthio;
    diphenylacetylamino, diphenylacetyl-phenylamino, diphenylpropionylamino, diphenylacryloylamino, naphthylacetylamino, furoylacrylamino, benzoylamino, naphthoylamino, oxofluoroenylcabonylamino, furoylamino;
    diphenylmethylaminocarbonylamino, dibenzylaminocarbonyl-amino, naphthylmethylaminocarbonylamino, dibenzylaminocarbonylamino, biphenylylaminocarbonyl-amino, naphthylaminocarbonylamino, benzylphenylaminocarbonylamino, diphenylaminocarbonylamino; diphenylaminocarbonyl-phenylamino; diphenylfurylaminocarbonylamino, indolinyl-N-carbonyl-amino, isoindolinyl-N-carbonylamino, 1H,3H-benzo[de]isoquinolinyl-N-carbonylamino, tetrahydrobenzoazepinyl-N-carbonylamino, phenyltetrahydrobenzoazepinyl-N-carbo-nylamino, dihydrodibenzoazepin-N-carbonylamino, dihydrobenzopyridoazepinyl-N-carbonylamino;

tolylsulfonylamino, naphthylsulfonylamino, diphenylphosphinoylamino and diphenylphosphinoyloxy, and whereby aromatic ring systems in G can be substituted independently from each other by one to three of the same or different groups selected from halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and for two adjacent residues on the aromatic ring, methylenedioxy, and whereby alkyl and cycloalkyl residues in the group G can be substituted by one or two of the same or different groups selected from hydroxy, carboxy, $C_2$-$C_7$-alkoxycarbonyl, benzyloxycarbonyl, amino, mono-$C_1$-$C_6$-alkylamino and di-($C_1$-$C_6$-alkyl) amino.

Very particularly, preferred concrete embodiments of the invention are represented by the following end products:

(1) N-[8,8-bis-(4-fluorophenyl)-octyl]-3-pyridin-3-yl-acrylamide.hydrochloride (substance 23 as hydrochloride)
(2) N-[6-(3,3-diphenyl-ureido)-hexyl]-3-pyridin-3-yl-acrylamide (substance 270)
(3) N-[4-(1-phenyl-1,2,4,5-tetrahydrobenzo[d]azepin-3-yl)-butyl]-3-pyridin-3-yl-acrylamide (substance 207)
(4) N-(8,8-diphenyl-octyl)-3-pyridin-3-yl-acrylamide (substance 17)
(5) N-(8-hydroxy-8,8-diphenyl-octyl)-3-pyridin-3-yl-acrylamide (substance 41)
(6) N-[4-(3,3-diphenyl-ureido)-butyl]-3-pyridin-3-yl-acrylamide (substance 268)
(7) N-[4-(1H,3H-benzo[de]isoquinolin-2-yl)-butyl]-3-pyridin-3-yl-acrylamide (substance 225)
(8) N-[6-(10,11-dihydrodibenzo[b,f]azepin-5-yl-carbonylamino)-hexyl]-3-pyridin-3-yl-acrylamide (substance 295)
(9) 3-pyridin-3-yl-N-[6-(tosylamino)-hexyl]-acrylamide (substance 310)
(10) N-[4-(1,1-dioxo-1-thia-2-aza-acenaphthylen-2-yl)-butyl]-3-pyridin-3-yl-acrylamide (substance 214)
(11) N-(6-hydroxy-6,6-diphenyl-hexyl)-3-pyridin-3-yl-acrylamide (substance 31)
(12) N-(6,6-diphenyl-hex-5-enyl)-3-pyridin-3-yl-acrylamide (substance 120)
(13) N-[4-(4,5-diphenyl-imidazol-1-yl)-butyl]-3-pyridin-3-yl-acrylamide (substance 63)
(14) N-[4-(trans-2-phenyl-cyclopropyl-carbonylamino)-butyl]-3-pyridin-3-yl-acrylamide (substance 250)
(15) N-(5-hydroxy-5,5-diphenyl-pentyl)-3-pyridin-3-yl-acrylamide (substance 27)
(16) N-(7-phenyl-heptyl)-3-pryrdin-3-yl-acrylamide (substance 3)
(17) N-(4-diphenylacetylamino-butyl)-3-pyridin-3-yl-acrylamide (substance 247)
(18) N-[4-(benzhydryl-amino)-butyl]-3-pyridin-3-yl-acrylamide (substance 187) and
(19) N-(4-{[2-(benhydrylmethylamino)-ethyl]-methylamino}-butyl)-3-pyridin-3-yl-acrylamide (substance 193).

Further subject-matter of the invention are known analogous methods already briefly mentioned above according to the different variants for the production of the compounds of formula (I) according to the invention.

According to the method (A), compounds of formula (I) are obtained by reacting carboxylic acids of formula (II)

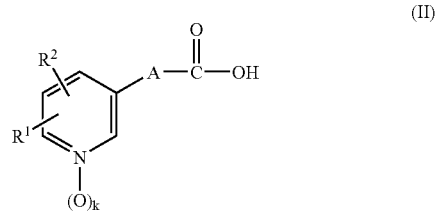

(II)

in which $R^1$, $R^2$, A and k have the meanings given above or their reactive derivatives with compounds of formula (III)

(III)

wherein D, G and $R^4$ are defined as above.

Reactive derivatives of compound (II) can be, for example, activated esters, anhydrides, acid halides (especially acid chlorides) or simple low alkyl esters. Suitable activated esters are, for example, p-nitrophenyl ester, 2,4,6-trichlorophenyl ester, pentachlorophenyl ester, cyanomethyl ester, esters of N-hydroxysuccinimide, N-hydroxyphthalimides, 1-hydroxybenzotriazole, N-hydroxypiperidine, of 2-hydroxypyridine, of 2-mercaptopyridine, etc. Anhydrides can be symmetric anhydrides or mixed, as they are obtained, for ex ample, with pivaloyl chloride or with chloroformates. Aromatic (for example chloroformic phenyl ester), araliphatic (for example chloroformic benzyl ester) or aliphatic chloroformates (for example chloroformic methyl ester, ethyl ester or isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)-carbodiimide hydrochloride, N,N'-carbonyldiimidazole, 1-ethoxycarbonyl-2-ethoxy-1,2-dihydroaquinoline, etc. If carbodiimides are used as the condensation agent, reagents such as N-hydroxysuccinimide, N-hydroxyphthalimide, 1-hydroxybenzotriazole, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates for example.

Reaction of compounds (II) or their reactive derivatives with compounds (III) are normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), ethers (for example diethyl ether, tetrahydrofuran, dioxane, glycol dimethyl ether), ethyl acetate, acetonitrile or polar aprotic solvents such as, for example, dimethylsulfoxide, dimethylformamide or N-methyl-pyrrolidone are to be named. Pure solvents, as well as mixtures of two or more, can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can—depending on reactivity of the educts—vary in a wide range. Generally, the reaction is carried out at temperatures between −40° C. and 180° C., preferably between −10° C. and 130° C., especially at the boiling point of the solvent used.

The starting compounds (II) and (III) are known and/or can be produced according to known methods in an analogous manner. Moreover, the production of representative examples is described in the following.

According to method (B), compounds of formula (I), wherein G corresponds to the meanings G3a, G4, G5 or G6 and, optionally, X equals $NR^{11}$, can also be produced by reacting compounds of formula (IV)

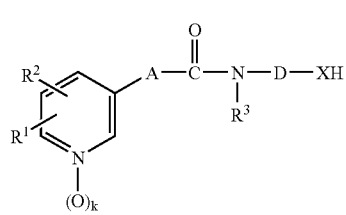
(IV)

with suitable alkylation or Arylation agents and/or carboxylic acid, carbamic acid, thiocarbamic acid, sulfonic acid or phosphinic acid derivatives of formula (Va) to (Ve),

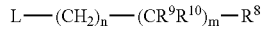
(Va)

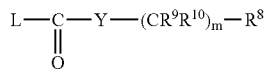
(Vb)

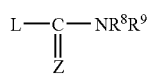
(Vc)

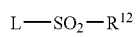
(Vd)

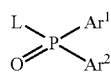
(Ve)

wherein each L is a suitable nucleofuge. The type of nucleofuge L and the conditions of the reaction depend on he nature of the residue to be transmitted.

Aside from method (A), compounds of formula (I) in which G as the meaning of G3a with $X=NR^{11}$ according to the above definition, can also be produced pursuant to a further method variant according to method (B1) by reacting compounds of formula (IV) with a suitable alkylation agent and/or arylation agent of formula (Va) wherein m, n, $R^8$, $R^9$ and $R^{10}$ are as defined above and the leaving group L can be the reactive derivatives of an alcohol for example, a halogen atom such as chlorine, bromine or iodine, or a sulfonic acid ester, i.e. for example, a methanesulfonyloxy residue, trifluoromethansulfonyloxy-, ethanesulfonyloxy-, benzenesulfonyloxy-, p-toluenesulfonyloxy-, p-brom-benzenesulfonyloxy-, m-nitrobenzenesulfonyloxy residue.

The reaction of compounds (IV) and (Va) are usually conducted in a suitably inert solvent. Such solvents can be for example, aromatic hydrocarbons (benzene, toluene, xylene) ethers (for example tetrahydrofuran, dioxane, glycol dimethyl ether), ethyl acetate, acetonitrile, ketones (acetone, ethyl methyl ketone), polar protic solvents such as alcohols (ethanol, isopropanol, butanol, glycol monomethyl ether) or polar aprotic solvents such as, for example, dimethylsulfoxide, dimethylformamide or N-methylpyrrolidone. Pure solvents as well as mixtures of two or more can also be used. Preferably, the reactions are carried out in the presence of bases, whereby the same bases as named in method (A) above can be used. If chlorides or bromides are used as compound (Va), the reaction can be accelerated by the addition of alkali metal iodides, for example sodium iodide, potassium iodide. The reaction temperatures can vary between 0° C. and 180° C. depending on the reactivity of the educts, but preferably lie between 20° C. and 130° C.

Aside from method (A), compounds of formula (I), wherein G has the meanings G4 to G6 according to the above definition, can also be produced according to method (32) by reacting compounds of formula (IV) with a carboxylic acid, thiocarbamic acid, Carbamic acid, sulfonic acid and/or phosphinic acid of the formulas (VIb) to (VIe), wherein m, Y, Z,$R^8$, $R^9$, $R^{10}$, $R^{12}$, $Ar^1$, $Ar^2$ and, optionally, the group $NR^8R^9$, have the above meanings,

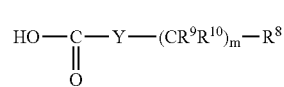
(VIb)

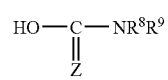
(VIc)

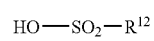
(VId)

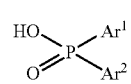
(VIe)

or their derivatives capable of reacting.

Preferred derivatives of carboxylic acids (VIb) and/or sulfonic acids (VId) which are capable of reaction are symmetric or unsymmetric carboxylic acid anhydrides and/or sulfonic acid anhydrides or acyl- and/or sulfonyl halides, especially acyl- and/or sulfonyl chlorides. Preferred derivatives of carbamic acids and/or thiocarbamic acids (VIc) and/or phosphinic acids (Vie) which are capable of reaction are the carbamoyl, thiocarbamoyl and/or phosphinyl halides, especially carbamyl, thiocarbamoyl and/or phosphinyl chlorides. The reaction of the acids (VI) and/or their reactive derivatives with compounds (IV) preferably occurs in the presence of auxiliary bases in solvents and under conditions as they are described in method (A).

Aside from methods (A) and (B2), compounds or formula (I), wherein G represents a carbamoyl residue according to the definition

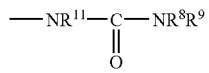

can also be produced according to method (B3) by reacting compounds of formula (IV), wherein X=NR$^{11}$, with a carbonyl group transmitter to an intermediate, and, subsequently, without purification or isolation of the intermediate, this is reacted with a primary or secondary amine of the formula (VII),

H—NR$^8$R$^9$ (VII), wherein R$^8$ and R$^9$ or, optionally, the residues NR$^8$R$^9$, have the meanings according to the above definitions.

Bis-trichloromethyl carbonate (triphosgene) and carbonyldiimidazole have been proven as particularly reactive carbonyl group transmitters. The reaction of compounds of formula (IV) with triphosgene and/or carbonyldiimidazole are typically conducted in an absolute, inert solvent in the presence of a tertiary organic amine as an auxiliary base in such a manner that the solution of compounds (IV) and the auxiliary base are slowly poured into a solution of an equivalent amount of carbonyl group transmitter. Thereby, the reaction requires molar ratios of 1:1 for the reaction of compound (IV) and carbonyldiimidazol, and, in contrast, a ratio of 1:0.35 for the use of triphosgene. After complete reaction of the components to the intermediate product, compound (VII) is added in stoichiometric amounts or in excess as a solution or a solid, whereby the reaction is typically completed at elevated temperature. Suitable inert solvents are, for example hydrocarbons such as hexane, heptane, benzene, toluene, xylene, chlorinated hydrocarbons (for example dichloromethane, chloroform, 1,2-dichloroethane, trichloroethylene), ethers (for example diethyl ether, tetrahydrofuran, dioxane), esters such as ethyl acetate, butyl acetate, acetonitrile or polar aprodic solvents such as formamide or dimethylformamide. Pure solvents as well as mixtures of various solvents can be used. Sometimes it is of advantage to carry out the first partial reaction at low temperature in a low-viscosity, highly-volatile solvent and to remove the solvent after formation of the intermediate and replace it by a higher boiling solvent. Amines such as for example triethylamine, ethyl diisopropylamine, tributylamine, N-methylmorpholine or pyridine are suitable as auxiliary bases. If compounds (IV) or (VII) are used as salts, the amount of the auxiliary base is increased accordingly. The reaction temperatures can lie between −40° C. and 50° C. for the first partial reaction, preferably 0° C. to 30° C., and between 0° C. and 150° C. for the second partial reaction, preferably 20° C. to 120° C.

Compounds of formula (I), wherein G represents a thiocarbamoyl residue according to the definition G4b with Z=S, i.e., is a group

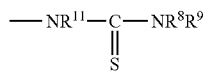

can be produced in a completely corresponding manner from compounds (IV) and (VII), by using thiocarbonyldiimidazole or thiophosgene as a thiocarbonyl group transmitter.

Finally, aside from methods (A), (B2) and (B3), compounds of formula (I), Wherein G represents a carbamoyl residue or thiocarbamoyl residue according to the definition G4b with R$^9$=hydrogen, i.e. is a group

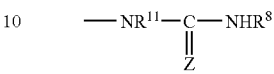

can also be produced according to method (B4) by reacting starting compounds of the formula (IV) wherein X=NR$^{11}$, with an isocyanate or isothiocyanate of the formula (VIII), in which R$^8$ has the meaning according to definition,

Z=C=N=R$^8$ (VIII)

Reaction of the compounds of formula (IV) with the isocyanates and/or isothio cyanates of formula (VIII) are conducted thereby in an absolute, inert solvents as they are named in method (B3). Mixtures of various solvents can also be used. Thereby, the reaction temperatures can vary in the region from −20° C. to 150° C., but preferably lie at 20° C. to 100° C.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compounds (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile; ketones such as acetone or ethyl methyl ketone; esters such as methyl acetate or ethyl acetate or low molecular alcohols such as methanol, ethanol or isopropanol; and water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

Synthetic examples for end products according to the invention are given in the following for further illustrating the above method variants:

SYNTHETIC EXAMPLES FOR THE END PRODUCTS OF THE INVENTION ACCORDING TO FORMULA (I)

In the production examples for the end products, the abbreviations stand for the following terms:
MP=melting point,
RT=room temperature,
MPLC=intermediate pressure liquid chromatography
THF=tetrahydrofuran,
DMF=dimethylformamide,
abs=absolute,
CDI=carbonyldiimidazole,
EDC=N-(3-dimethylaminopropyl)-N'-ethyl-carbodiimide hydrochloride, HOBT=1-hydroxybenzotriazole,
TEA=triethylamine.
$^1$H-NMR-Spectrum=proton resonance spectrum, taken at 100 MHz. The chemical shifts are given in ppm against TMS as a standard (δ=0.0), whereby
- s=singlet,
- d=doublet,
- t=triplet,
- dt=doublet-triplet,
- m=multiplet,
- ar=aromatic,
- py=pyridine.

Example 1

N-[8,8-bis-(4-fluoro-phenyl)-octyl]-3-pyridin-3-yl-acrylamide.hydrochloride (Substance 23 as a hydrochloride)

1.34 g (9.0 mmol) 3-(3-pyridyl)-acrylic acid are suspended in 20 ml abs. dichloromethane and, after addition of two drops pyridine, are cooled in an ice bath to ca. 0° C. under moisture exclusion. 2 ml (23.2 mmol) oxalyl chloride are slowly added, and the mixture is first stirred for 30 min under ice cooling and then overnight at RT. Subseauently, the solvent and oxalyl chloride are distilled off on a rotary evaporator. In order to completely remove the oxalyl chloride, the colourless residue is further dried for two hours under high vacuum. The acid chloride obtained in this manner is suspended in 20 ml abs. dichloromethane and cooled in an ice bath at ca. 0° C. under moisture exclusion. 2.4 g (7.5 mmol) 8,8-bis-(4-fluorophenyl)-octylamine in 40 ml abs. dichloromethane together with 0.9 g (9.0 mmol) TEA are added dropwise to the suspension. After complete addition, the ice bath is removed and the reaction is stirred for a further two hours at RT. The mixture is subsequently concentrated, taken up in 10% sodium hydroxide solution and extracted three time with acetic acid ethyl ester. The combined organic phases are washed with saturated NaCl solution, dried over sodium sulfate and the solvent is removed under vacuum. The residue is chromatographically purified over silica gel with CHCl$_3$/CH$_3$OH (95/5) and. After withdraw of the solvent, the residue is dissolved in methanol and added to a methanolic HCl solution. The drawn off HCl salt is crystallized twice from 70 ml acetone. Colorless crystals with MP. 126-129° C. Yield 2.4 g (42%).

$C_{28}H_{30}F_2N_2O_3$·HCl (485.0)

| IR-Spectrum (KBr): | ν(NH) | 3280 cm$^{-1}$ |
| --- | --- | --- |
| | ν(C=O) | 1670, 1635, 1550 cm$^{-1}$ |
| | ν(C=C) | 1600 cm$^{-1}$ |
| $^1$H-NMR-Spectrum (CDCl$_3$): | 1.00-2.15(12H, m, C—(CH$_2$)$_6$—C) | |
| | 3.20-3.55(2H, m, CONHC<u>H</u>$_2$) | |
| | 3.84(1H, t, Ar$_2$CH, J=7.7Hz) | |
| | 6.80-3.00(13H, m, Ar, Py, CH=CH, NH, HCl) | |
| | 8.30-8.45(1H, m, Py) | |
| | 8.60-8.75(1H, m, Py) | |
| | 9.30-9.45(1H, m, Py) | |

Example 2

N-[6-(3,3-diphenyl-ureido)-hexyl]-3-pyridin-3-yl-acrylamide (Substance 270)

Production analogous to Example 1.
Batch size: 2.6 g (17.6 mmol) 3-(3-pyridyl)-acrylic acid, 1.8 ml (20.8 mmol) oxalyl chloride and 5.0 g (16.0 mmol) 6-(3,3-diphenyl-ureido)-hexylamine.

In the purification, chromatography first occurs over silica gel with CHCl$_3$/CH$_3$OH (100/0 bis 95/5), subsequently, this is crystallized from 25 ml acetic acid ethyl ester/petroleum ether (4/1): Colorless crystals with MP. 105-107° C.; Yield 1.1 g (15%).

$C_{27}H_{30}N_4O_2$ (442.6)

| IR-Spectrum (KBr): | ν(NH) | 3340, 3270 cm$^{-1}$ |
| --- | --- | --- |
| | ν(C=O) | 1655, 1540 cm$^{-1}$ |
| | ν(C=C) | 1615 cm$^{-1}$ |
| $^1$H-NMR-Spectrum (CDCl$_3$): | 1.25-1.80(8H, m, C—(CH$_2$)$_4$—C) | |
| | 3.20-3.60(4H, m, CONHC<u>H</u>$_2$) | |
| | 4.50-4.75(1H, m, NH) | |
| | 6.38(1H, d, CH=CHCO, J=13.7Hz) | |
| | 6.40-6.65 (1H, m, NH) | |
| | 7.05-7.50 (11H, m, Ar, Py) | |
| | 7.54 (1H, d, C<u>H</u>=CHCO, J=15.7Hz) | |
| | 7.60-7.75 (1H, m, Py) | |
| | 8.50-8.60 (1H, m, Py) | |
| | 8.60-8.70 (1H, m, Py) | |

Example 3

N-[4-(1-phenyl-1,2,4,5-tetrahydrobenzo[d]azepin-3-yl)-butyl]-3-pyridin-3-yl-acrylamide (Substance 207)

Production analogous to Example 1.
Batch size: 2.8 g (18.8 mmol) 3-(3-Pyridyl)-acrylic acid, 2.2 ml (25.5 mmol) oxalyl chloride and 5.0 g (17.0 mmol) 4-(1-phenyl-1,2,4,5-tetrahydrobenzo[d]azepin-3-yl)-butylamine.

In the purification, chromatography first occurs over silica gel with CHCl$_3$/CH$_3$OH (95/5); subsequently, the oily residue is rubbed with diisopropyl ether until crystillization occurs: Colorless crystals with MP. 92-94° C.; Yield 0.7 g (9%).

$C_{28}H_{31}N_3O$ (425.6)

| IR-Spectrum (KBr): | ν(NH) | 3300 cm$^{-1}$ |
| --- | --- | --- |
| | ν(C=O) | 1655, 1530 cm$^{-1}$ |
| | ν(C=C) | 1615 cm$^{-1}$ |
| $^1$H-NMR-Spectrum (CDCl$_2$): | 1.45-1.85(4H, m, C—CH$_2$—CH$_2$—C) | |
| | 2.33-3.60(10H, m, N—CH$_2$, Tetrahydroazepine, CONHC<u>H</u>$_2$) | |
| | 4.30-4.55(1H, m, ArCH) | |
| | 6.10-6.35(1H, m, NH) | |
| | 6.37(1H, d, CH=C<u>H</u>CO, J=15.7Hz) | |
| | 6.60-7.50(10H, m, Ar, Py) | |
| | 7.59(1H, d, C<u>H</u>=CHCO, J=15.7Hz) | |
| | 7.60-7.90(1H, m, Py) | |
| | 8.50-8.65(1H, m, Py) | |
| | 8.65-8.80(1H, m, Py) | |

Example 4

N-(8,8-diphenyl-octyl)-3-pyridin-3-yl-acrylamide (Substance 17)

Production analogous to Example 1.
Batch size: 2.7 g (18.0 mmol) 3-(3-pyridyl)-acrylic acid, 5 ml (57.9 mmol) oxalyl chloride, 3.9 ml (28.0 mmol) TEA and 4.0 g (14,0 mmol) 8,8-diphenyloctylamine.

In the purification, chromatography first occurs over silica gel with CHCl$_3$/CH$_3$OH (95/5); subsequently, this is crystallized twice from 100 ml acetic acid ethyl ester/diisopropyl ether: Colorless crystals with MP. 92-93° C. in a yield of 3.1 g (54%)

C$_{28}$H$_{32}$N$_2$O (412.6)

| | | |
|---|---|---|
| IR-Spectrum (KBr): | ν(NH) | 3240 cm$^{-1}$ |
| | ν(C=O) | 1645, 1530 cm$^{-1}$ |
| | ν(C=C) | 1610 cm$^{-1}$ |
| $^1$H-NMR-Spectrum (CDCl$_3$): | 1.10-2.20(12H, m, C—(CH$_2$)$_6$—C) | |
| | 3.36(2H, dt, CONHC$\underline{H}_2$, J=6.5Hz, J=12.7Hz) | |
| | 3.88(1H, t, Ar$_2$CH, J=7.7Hz) | |
| | 5.55-5.80(1H, m, NH) | |
| | 6.43(1H, d, CH=C$\underline{H}$CO, J=15.6Hz) | |
| | 7.03-7.40(11H, m, Ar, Py) | |
| | 7.61(1H, d, C$\underline{H}$=CHCO, J=13.6Hz) | |
| | 7.65-7.85(1H, m, Py) | |
| | 8.50-8.65(1H, m, Py) | |
| | 8.65-8.80(1H, m, Py) | |

Example 5

N-(8-hydroxy-8,8-diphenyloctyl)-3-pyridin-3-yl-acrylamide (Substance 41)

3.4 g (23.0 mmol) 3-(3-pyridyl)-acrylic acid and 3.7 g (23.0 mmol) CDI are heated under reflux in 50 ml THF under moisture exclusion. After one hour this is cooled to RT and 6.5 g (21.9 μmmol) 8-hydroxy-8,8-diphenyloctylamine, dissolved in 20 ml THF, is added dropwise. After complete addition, stirring is carried out for a further three hours at RT and this is left to stand overnight. 50 ml water is added to the mixture and extracted three times with acetic acid ethyl ester by shaking. The combined organic phases are washed with saturated NaCl solution, dried over sodium sulfate, and the solvent is removed under vacuum. The residue is chromatographically purified over silica gel with CHCl$_3$/CH$_3$OH (95/5) and subsequently, crystallized twice from 200-ml and 140 ml acetic acid ethyl ester: Colorless crystals with MP. 139-140° C. in a yield of 3.7 g (39%). C$_{28}$H$_{32}$N$_2$O$_2$ (428.6)

| | | |
|---|---|---|
| IR-Spectrum (KBr): | ν(NH) | 3270 cm$^{-1}$ |
| | ν(C=O) | 1660, 1540 cm$^{-1}$ |
| | ν(C=C) | 1610 cm$^{-1}$ |
| $^1$H-NMR-Spectrum (CDCl$_3$): | 1.05-1.70(10H, m, C—(CH$_2$)$_5$—C) | |
| | 2.05-2.40(2H, m, C(OH)—C$\underline{H}_2$) | |
| | 3.27(2H, dt, CONHC$\underline{H}_2$, J=6.4Hz, J=12.3Hz) | |
| | 4.59(1H, s, OH) | |
| | 6.66(1H, d, CH=C$\underline{H}$CO, J=15.8Hz) | |
| | 7.05-7.65 (13H, m, Ar, Py, C$\underline{H}$=CHCO, NH) | |
| | 7.75-7.90(1H, m, Py) | |
| | 8.45-8.60(1H, m, Py) | |
| | 8.65-8.75(1H, m, Py) | |

Example 6

N-[4-(3,3-diphenyl-ureido)-butyl]-3-pyridin-3-yl-acrylamide (Substance 268)

Production analogous to Example 1.

Batch size: 3.5 g (23.5 mmol) 3-(3-pyridyl)-acrylic acid, 4.0 g (31.5 mmol) oxalyl chloride and 6.0 g (21.1 mmol) 4-(3,3-diphenyl-ureido)-butylamine.

In the purification, chromatography first occurs with CHCl$_3$/CH$_3$OH (95/5), subsequently; this is crystallized from 100 ml acetic acid ethyl ester. Beige colored crystals with MP. 123-125° C. Yield 4.1 g (46%).

C$_{25}$H$_{26}$N$_4$O$_2$ (414,5)

| | | |
|---|---|---|
| IR-Spectrum (KBr): | ν(NH) | 3400, 3280 cm$^{-1}$ |
| | ν(C=O) | 1670, 1640, 1560 cm$^{-1}$ |
| | ν(C=C) | 1600 cm$^{-1}$ |
| $^1$H-NMR-Spectrum (CDCl$_3$): | 1.45-1.70(4H, m, C—CH$_2$—CH$_2$—C) | |
| | 3.10-3.55(4H, m, CONHC$\underline{H}_2$) | |
| | 4.60-4.80(1H, m, NH) | |
| | 6.50(1H, d, CH=C$\underline{H}$CO, J=15.7Hz) | |
| | 6.70-6.95(1H, m, NH) | |
| | 7.05-7.50(11H, m, Ar, Py) | |
| | 7.58(1H, d, C$\underline{H}$=CNCO, J=15.7Hz) | |
| | 7.60-7.80(1H, m, Py) | |
| | 8.45-8.60(1H, m, Py) | |
| | 8.60-8.75(1H, m, Py) | |

Example 7

N-[4-(1H,3H-benzo[de]isoquinolin-2-yl)-butyl]-3-pyridin-3-yl-acrylamide (Substance 225)

Production analogous to Example 1.

Batch size: 1.8 g (12.1 mmol) 3-(3-pyridyl)-acrylic acid, 4.0 g (31.5 mmol) oxalyl chloride and 2.6 g (10.8 mmol) 4-(1H,3H-benzo[de]isoquinolin-2-yl)-butylamine.

In the purification, chromatography first occurs over silica gel with CHCl$_3$/CH$_3$OH (90/10); subsequently, this is crystallized from 10 ml acetic acid ethyl ester: Colorless crystals with MP. 118-120° C. in a yield of 0.37 g (9%).

C$_{24}$H$^{25}$N$_3$O (371.5)

| | | |
|---|---|---|
| IR-Spectrum (K3r): | ν(NH) | 3260 cm$^{-1}$ |
| | ν(C=O) | 1630, 1350 cm$^{-1}$ |
| | ν(C=C) | 1615 cm$^{-1}$ |
| $^1$H-NMR-Spectrum (CDCl$_3$): | 1.50-2.10(4H, m, C—CH$_2$—CH$_2$—C) | |
| | 2.55-2.90(2H, m, N—CH$_2$) | |
| | 3.25-3.55(2H, m, CONHC$\underline{H}_2$) | |
| | 4.00(4H, s, ArCH$_2$) | |
| | 5.60(1H, d, CH=C$\underline{H}$CO, J=15.6Hz) | |
| | 7.00-7.90(10H, m, Ar, Py, NH, CH=C$\underline{H}$CO) | |
| | 8.30-8.45(1H, m, Py) | |
| | 8.45-8.65(1H, m, Py) | |

Example 8

N-[6-(10,11-dihydro-dibenzo[b,f]azepin-5-yl-carbonylamino)-hexyl]-3-pyridin-3-yl-acrylamide (Substance 295)

Production analogous to Example 1.

Batch size: 2.2 g (14.8 mmol) 3-(3-pyridyl)-acrylic acid, 2.5 g (19.7 mmol) oxalyl chloride, 4.5 g (44.5 mmol) TEA and 5.0 g (13.4 mmol) 6-(10,11-dihydro-dibenzo[b,f]azepin-5-yl-carbonylamino)-hexylamine hydrochloride.

In the purification, chromatography first occurs over silica gel with CHCl$_3$/CH$_3$OH (95/5 to 93/7) subsequently, this is crystallized from 15 ml acetonitrile: Colorless crystals with MP. 97-99° C. in a yield of 1.35 g (21%).

C$_{29}$H$_{32}$N$_4$O$_2$ (468.6)

| | | |
|---|---|---|
| IR-Spectrum (K3r): | ν(NH) | 3280 cm$^{-1}$ |
| | ν(C=O) | 1670, 1540 cm$^{-1}$ |
| | ν(C=C) | 1620 cm$^{-1}$ |
| $^1$H-NMR-Spectrum (CDCl$_3$): | 1.10-1.75(8H, m, C—(CH$_2$)$_4$—C) | |
| | 2.80-3.55(8H, m, CONHC$\underline{H}_2$, ArCH$_2$) | |
| | 4.50-4.70(1H, m, NH) | |
| | 6.31(1H, d, CH=C$\underline{H}$CO, J=15.7Hz) | |
| | 6.65-6.85(1H, m, NH) | |
| | 7.00-7.40(9H, m, Ar, Py) | |
| | 7.50(1H, d, C$\underline{H}$=CHCO, J=15.7Hz) | |
| | 7.55-7.75(1H, m, Py) | |
| | 8.45-8.70(2H, m, Py) | |

Example 9

3-Pyridin-3-yl-N-[6-(tosylamino)-hexyl]-acrylamide (Substance 310)

Production Analogous to Example 1.

Batch size: 4.1 g (27.5 mmol) 3-(3-pyridyl)-acrylic acid, 4.7 g (37.0 mmol) oxalyl chloride, 5.0 g (49.4 mmol) TEA and 8.6 g (25.0 mmol) 6-(tosylamino)-hexylamine.dihydrochloride.

In the purification, chromatography first occurs over silica gel with CHCl$_3$/CH$_3$OH (95/5) and subsequently crystallized from 60 ml acetonitrile: Colorless crystals with MP. 91-93° C. in a yield of 4.0 g (40%).

$C_{21}H_{27}N_3O_3S$ (401.5)

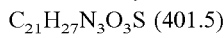

| | | |
|---|---|---|
| IR-Spectrum (KBr): | ν(NH) | 3320, 3280 cm$^{-1}$ |
| | ν(C=O) | 1650, 1530 cm$^{-1}$ |
| | ν(C=C) | 1620 cm$^{-1}$ |
| $^1$H-NMR-Spectrum (CDCl$_3$): | 1.15-1.70(8H, m, C—(CH$_2$)$_4$—C) | |
| | 2.40(3H, s, CH$_3$) | |
| | 2.75-3.05(2H, m, SO$_2$NHC$\underline{H}_2$) | |
| | 3.15-3.50(2H, m, CONHC$\underline{H}_2$) | |
| | 5.55-5.80(1H, m, NH) | |
| | 6.62(1H, d, CH=C$\underline{H}$CO, J=15.9Hz) | |
| | 6.60-6.85(1H, m, NH) | |
| | 7.15-7.95(7H, m, Ar, Py, C$\underline{H}$=CHCO) | |
| | 8.45-8.60(1H, m, Py) | |
| | 8.60-8.80(1H, m, Py) | |

Example 10

N-[4-(1,1-dioxo-1-thia-2-aza-acenaphthylen-2-yl)-butyl]-3-pyridin-3-yl-acrylamide (Substance 214)

8.0 g (36.3 mmol) N-(4-hydroxy-butyl)-3-pyridin-3-yl-acrylamide, 9.5 g (36.3 mmol) triphenylphosphine and 7.6 g (36.3 mmol) 1,8-naphthalinsultam are suspended in 100 ml THF. And 6.3 g (36.3 mmol) azodicarboxylic acid diethyl ester dissolved in 50 ml THF are added dropwise within three hours under protective atmosphere and light cooling (to ca. 15° C.). The mixture is left standing overnight at RT without further cooling. Subsequently, the solvent is removed under vacuum and the residue is chromatography purified twice over silica gel with CHCl$_3$/CH$_3$OH (90/10) and CHCl$_3$/CH$_3$OH (99/1 to 95/5) and, after withdraw of the solvent, crystallized from 30 ml acetic acid ethyl ester. Colorless crystals with MP. 122-124° C. Yield 1.0 g (6%).

$C_{23}H_{21}N_3O_3S$ (407.5)

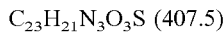

| | | |
|---|---|---|
| IR-Spectrum (KBr): | ν(NH) | 3280 cm$^{-1}$ |
| | ν(C=O) | 1640, 1580 cm$^{-1}$ |
| | ν(C50 C) | 1610 cm$^{-1}$ |
| $^1$H-NMR-Spectrum (CDCl$_3$): | 1.60-2.35(4H, m, C—CH$_2$—CH$_2$—C) | |
| | 3.47(2H, dt, CONHC$\underline{H}_2$, J=6.2Hz, J=12.2Hz) | |
| | 3.87(2H, t, SO$_2$NCH$_2$, J=6.5Hz) | |
| | 6.25-6.60(1H, m, NH) | |
| | 6.49(1H, d, CH=C$\underline{H}$CO, J=15.7Hz) | |
| | 6.60-6.90(1H, m, Ar) | |
| | 7.10-8.20(8H, m, Ar, Py) | |
| | CH=C$\underline{H}$CO | |
| | 8.40-8.85(2H, m, Py) | |

Example 11

N-(6-hydroxy-6,6-diphenyl-hexyl)-3-pyridin-3-yl-acrylamide (Substance 31)

Production Analogous to Example 5.

Batch size: 3.2 g (21.6 mmol) 3-(3-pyridyl)-acrylic acid, 3.85 g (23.8 mmol) CDI and 4.2 g (25.9 mmol) 6-hydroxy-6,6-diphenyl-hexylamine in 60 ml abs. THF.

In carrying out the reaction, the amine is added dropwise at 0° C. In the work-up, chloroform is used in the extraction. Purification occurs by chromatography on silica gel with CHCl$_3$/CH$_3$OH (92/8). Subsequently, this is crystallized twice from 25 ml acetic acid ethyl ester and 45 ml acetonitrile. Colorless crystals with MP. 145-147° C. Yield 2.5 g (29%).

$C_{26}H_{28}N_2O_2$ (400.5)

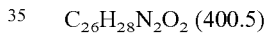

| | | |
|---|---|---|
| IR-Spectrum (KBr): | ν(NH) | 3240 cm$^{-1}$ |
| | ν(C=O) | 1650, 1560 cm$^{-1}$ |
| | ν(C=C) | 1610 cm$^{-1}$ |
| $^1$H-NMR-Spectrum (CDCl$_3$): | 1.15-1.80(6H, m, C—(CH$_2$)$_3$—C) | |
| | 2.15-2.65(3H, m, C(OH)CH$_2$) | |
| | 3.20-3.50(2H, m, CONHC$\underline{H}_2$) | |
| | 5.65-6.00(1H, m, NH) | |
| | 6.42(1H, d, CH=C$\underline{H}$CO, J=15.7Hz) | |
| | 7.05-7.55(11H, m, Ar, Py) | |
| | 7.58(1H, d, CH=C$\underline{H}$CO, J=15.7Hz) | |
| | 7.60-7.85(2H, m, Py) | |
| | 8.40-8.60(1H, m, Py) | |
| | 8.60-8.80(1H, m, Py) | |

Example 12

N-(6,6-diphenyl-hex-5-enyl)-3-pyridin-3-yl-acrylamide (Substance 120)

Production analogous to Example 1.

Batch size: 2.6 g (17.4 mmol) 3-(3-pyridyl)-acrylic acid, 6.0 g (47.3 mmol) oxalyl chloride and 4.0 g (15.9 mmol) 6,6-diohenyl-hex-5-enylamine.

In the purification, chromatography first occurs with CHCl$_3$/CH$_3$OH (90/10) and, subsequently, this is crystallized twice from acetic acid ethyl ester. Colorless crystals with MP. 120-121° C. Yield 2.2 g (36%)

$C_{26}H_{26}N_2O$ (382.5)

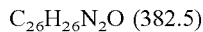

| | | |
|---|---|---|
| IR-Spectrum (KBr): | ν(NH) | 3250 cm$^{-1}$ |
| | ν(C=O) | 1650, 1560 cm$^{-1}$ |
| | ν(C=C) | 1610 cm$^{-1}$ |
| $^1$H-NMR-Spectrum (CDCl$_3$): | 1.30-1.85(4H, m, C—CH$_2$—CH$_2$—C) | |
| | 1.95-2.40(2H, m, =CH—CH$_2$) | |
| | 3.20-3.60(2H, m, CONHCH$_2$) | |
| | 5.70-5.90(1H, m, NH) | |
| | 6.06(1H, t, =CH—CH$_2$, J=7.3Hz) | |
| | 6.43(1H, d, CH=CHCO, J=15.6Hz) | |
| | 7.00-7.60(11H, m, Ar, Py) | |
| | 7.61(1H, d, CH=CHCO, J=15.6Hz) | |
| | 7.65-7.95(1H, m, Py) | |
| | 8.50-8.65(1H, m, Py) | |
| | 8.65-8.90(1H, m, Py) | |

Example 13

N-[4-(4,5-diphenyl-imidazol-1-yl)-butyl]-3-pyridin-3-yl-acrylamide (Substance 63)

Production analogous to Example 1.

Batch size: 2.5 g (17.0 mmol) 3-(3-pyridyl)-acrylic acid, 5.9 g (46.3 mmol) oxalyl chloride and 4.5 g (15.4 mmol) 4-(4,5-diphenyl-imidazol-1-yl)-butylamine.

In the purification, pre-purification first occurs by chromatography over silica gel with CHCl$_3$/CH$_3$OH/NH$_4$OH (85/15/2) and, subsequently, flash-chromatography is carried out with CHCl$_3$/CH$_3$OH (95/5). Subsequently, a crystallization from acetonitrile occurs. Colorless crystals with MP. 183° C. Yield 4.6 g (70%).

C$_{27}$H$_{26}$N$_4$O (422.5)

| | | |
|---|---|---|
| IR-Spectrum (KBr): | ν(NH) | 3230 cm$^{-1}$ |
| | ν(C=O) | 1665, 1550 cm$^{-1}$ |
| | ν(C=C) | 1625 cm$^{-1}$ |
| $^1$H-NMR-Spectrum (CDCl$_3$): | 1.25-1.90(4H, m, C—CH$_2$—CH$_2$—C) | |
| | 3.10-3.45(2H, m, CONHCH$_2$) | |
| | 3.70-4.00(2H, m, Imidazol-CH$_2$) | |
| | 6.49(1H, d, CH=CHCO, J=15.7Hz) | |
| | 7.05-7.80(15H, m, Ar, Py, NH, CH=CHCO, Imidazol) | |
| | 8.45-8.60(1H, m, Py) | |
| | 8.60-8.75(1H, m, Py) | |

Example 14

N-[4-(trans-2-phenyl-cyclopropyl-carbonylamino)-butyl]-3-pyridin-3-yl-acrylamide (Substance 250)

2.4 g (16.1 mmol) 3-(3-pyridyl)-acrylic acid and 5.3 ml (38.0 mmol) TEA are suspended in 80 ml abs. dichloromethane and cooled to ca. 0° C. under moisture exclusion. 2.9 g (18.9 mmol) 88% HOBT and 3.6 g (18.8 mmol) EDC are added and the mixture is stirred for 30 min under ice cooling. 5.3 g (17.0 mmol) 4-(trans-2-phenyl-cyclopropyl-carbonylamino)-butylamine are dissolved in 30 ml abs. dichloromethane and added drop-wise under ice cooling. The mixture is stirred overnight at RT without further cooling. The formed precipitate is filtered off and crystallized from 120 ml isopropanol. Colorless crystals with MP. 194-196° C. Yield 4.2 g (71%).

C$_{22}$H$_{25}$N$_3$O$_2$ (363.5)

| | | |
|---|---|---|
| IR-Spectrum (KBr): | ν(NH) | 3280 cm$^{-1}$ |
| | ν(C=O) | 1650, 1545 cm$^{-1}$ |
| | ν(C=C) | 1620 cm$^{-1}$ |
| $^1$H-NMR-Spectrum ((CD$_3$)$_2$SO): | 1.05-1.60(6H, m, C—CH$_2$—CH$_2$—C, cyclopropane) | |
| | 1.70-1.95(1H, m, cyclopropane) | |
| | 2.10-2.35(1H, m, cyclopropane) | |
| | 2.90-3.35(4H, m, CONHCH$_2$) | |
| | 6.52(1H, d, CH=CHCO, J=15.9Hz) | |
| | 7.00-7.55(7H, m, Ar, Py, CH=CHCO) | |
| | 7.85-8.30(3H, m, NH, Py) | |
| | 8.45-8.60(1H, m, Py) | |
| | 8.70-8.80(1H, m, Py) | |

Example 15

N-(5-hydroxy-5,5-diphenyl-pentyl)-3-pyridin-3-yl-acrylamide (Substance 27)

Production analogous to Example 5.

Batch size: 1.7 g (11.3 mmol) 3-(3-pyridyl)-acrylic acid, 1.7 g (10 mmol) CDI and 2.4 g (9.4 mmol) 5-hydroxy-5,5-diphenyl-pentylamine in 40 ml abs. THF.

In carrying out the reaction, the amine is added dropwise at 0° C. In the work-up chloroform: is used for the extraction. Purification occurs by chromatograhy on silica gel with CHCl$_3$/CH$_3$OH (90/10). Subsequently, crystallization occurs three times from acetic acid ethyl ester. Colorless crystals with MP. 157-159° C. Yield 1.1 g (30%).

C$_{25}$H$_{26}$N$_2$O$_2$ (386.5)

| | | |
|---|---|---|
| IR-Spectrum (KBr): | ν(NH) | 3250 cm$^{-1}$ |
| | ν(C=O) | 1650, 1540 cm$^{-1}$ |
| | ν(C=C) | 1610 cm$^{-1}$ |
| $^1$H-NMR-Spectrum (CDCl$_3$): | 1.20-1.85(4H, m, C—CH$_2$—CH$_2$—C) | |
| | 2.15-2.50(2H, m, C(OH)CH$_2$) | |
| | 2.50-3.10(1H, m, OH) | |
| | 3.20-3.50(2H, m, CONHCH$_2$) | |
| | 5.80-6.10(1H, m, NH) | |
| | 6.40(1H, d, CH=CHCO, J=15.7Hz) | |
| | 7.00-7.90(13H, m, Ar, Py, CH=CHCO) | |
| | 8.45-8.60(1H, m, Py) | |
| | 8.60-8.80(1H, m, Py) | |

Example 16

N-(7-phenyl-heptyl)-3-pyridin-3-yl-acrylamide (Substance 3)

Production analogous to Example 1.

Batch size: 5.1 g (33.9 mmol) 3-(3-pyridyl)-acrylic acid, 6.6 ml (76.4 mmol) oxalyl chloride and 5.9 g (30.8 mmol) 7-phenyl-heptylamine.

In the purification, pre-purification first occurs by chromatography on silica gel with CHCl$_3$/CH$_3$OH (95/5) and, subsequently, flash-chromatography is carried out with CHCl$_3$/CH$_3$OH (95/5). Amorphous solid material with MP. 61-63° C. Yield 2.3 g (23%).

C$_{21}$H$_{26}$N$_2$O (322.5)

| IR-Spectrum (KBr): | ν(NH) | 3280 cm⁻¹ |
| --- | --- | --- |
| | ν(C=O) | 1650, 1530 cm⁻¹ |
| | ν(C=C) | 1610 cm⁻¹ |
| ¹H-NMR-Spectrum (CDCl₃): | 1.10-1.80(10H, m, C—(CH₂)₅—C) | |
| | 2.60(2H, t, Ar—CH₂, J=7.4Hz) | |
| | 3.38(2H, dt, CONHCH₂, J=6.5Hz, J=12.6Hz) | |
| | 5.80-6.10(1H, m, NH) | |
| | 6.47(1H, d, CH=CHCO, J=15.6Hz) | |
| | 7.05-7.40(6H, m, Ar, Py) | |
| | 7.61(1H, d, CH=CHCO, J=15.6Hz) | |
| | 7.65-7.85(1H, m, Py) | |
| | 8.50-8.60(1H, m, Py) | |
| | 8.65-8.80(1H, m, Py) | |

Example 17

N-(4-diphenylacetylamino-butyl)-3-pyridin-3-yl-acrylamide (Substance 247)

Production analogous to Example 14.

Batch size: 2.0 g (13.4 mmol) 3-(3-pyridyl)-acrylic acid, 3.0 g (29.6 mmol) TEA, 2.4 g (15.6 mmol) 88% HOBT, 3.0 g (15.6 mmol) EDC and 4.0 g (13.4 mmol) 4-diphenylacetylamino-butylamine hydrochloride.

In the purification, the formed precipitate is filtered of chromatographically purified over silica gel with CHCl₃/CH₃OH. (95/5) and, subsequently, crystallized from 70 ml isopropanol. The formed crystals are once again purified by chromatography over silica gel with CHCl₃/CH₃OH (95/5). Amorphous solid material with MP. 171-172° C. Yield 2.85 g (51%).

C₂₆H₂₇N₃O₂ (413.5)

| IR-Spectrum (KBr): | ν(NH) | 3280 cm⁻¹ |
| --- | --- | --- |
| | ν(C=O) | 1660, 1640, 1545 cm⁻¹ |
| | ν(C=C) | 1600 cm⁻¹ |
| ¹H-NMR-Spectrum (CDCl₃): | 1.40-1.70(4H, m, C—CH₂—CH₂—C) | |
| | 3.20-3.50(4H, m, CONHCH₂) | |
| | 4.94(1H, s, Ar₂CH) | |
| | 6.00-6.20(1H, m, NH) | |
| | 6.49(1H, d, CH=CHCO, J=15.7Hz) | |
| | 6.60-6.80(1H, m, NH) | |
| | 7.05-7.50(11H, m, Ar, Py) | |
| | 7.58(1H, d, CH=CHCO, J=15.7Hz) | |
| | 7.60-7.80(1H, m, Py) | |
| | 8.50-8.60(1H, m, Py) | |
| | 8.60-8.75(1H, m, Py) | |

Example 18

N-[4-(benzhydryl-amino)-butyl]-3-pyridin-3-yl-acrylamide (Substance 187)

Production analogous to Example 5.

Batch size: 1.9 g (12.6 mmol) 3-(3-pyridyl)-acrylic acid, 2.5 g (15.1 mmol) CDI and 3.7 g (14.5 mmol) 4-(benzhydryl-amino)-butylamine in 60 ml abs. THF.

In carrying out the reaction, the amine is added dropwise at −15° C., and the reaction mixture is stirred for three hours at this temperature. In the work-up, chloroform is used for extraction. Purification occurs by chromatography over silica gel with CHCl₃/CH₃OH (95/5). Subsequently, this is crystallized three times from 20 ml and 13 ml 1-chlorobutane and 10 ml acetonitrile. Beige colored crystals with MP. 101-102° C. Yield 1.0 g (20%).

C₂₅H₂₇N₃O (385.5)

| IR-Spectrum (KBr): | ν(NH) | 3260 cm⁻¹ |
| --- | --- | --- |
| | ν(C=O) | 1660, 1560 cm⁻¹ |
| | ν(C=C) | 1630 cm⁻¹ |
| ¹H-NMR-Spectrum (CDCl₃): | 1.45-1.90(4H, m, C—CH₂—CH₂—C) | |
| | 2.50-2.80(2H, m, NCH₂) | |
| | 3.25-3.55(2H, m, CONHCH₂) | |
| | 4.81(1H, s, Ar₂CH) | |
| | 6.32(1H, d, CN=CHCO, J=15.7Hz) | |
| | 6.30-6.55(1H, m, NH) | |
| | 7.10-7.80(14H, m, Ar, Py, NH, CH=CHCO) | |
| | 8.45-8.75(2H, m, Py) | |

Example 19

N-(4-{[2-(benzhydryl-methyl-amino)-ethyl]-methyl-amino}-butyl)-3-pyridin-3-yl-acrylamide (Substance 193)

Production analogous to Example 1.

Batch size: 5.5 g (36.8 mmol) 3-(3-pyridyl)-acrylic acid, 12.7 g (100.0 mmol) oxalyl chloride and 10.9 g (33.5 mmol) 4-([2-(benzhydryl-methyl-amino)-ethyl]-methyl-amino)-butylamine.

In the purification, this is first chromatographed with CHCl₃/CH₃OH (97/3 to 90/10) and, subsequently, the oily residue is rubbed with diisopropyl ether until crystallization occurs. Colorless crystals with MP. 89-91° C. Yield 3.0 g (19%).

C₂₉H₃₆N₄O (456.6)

| IR-Spectrum (KBr): | ν(NH) | 3300 cm⁻¹ |
| --- | --- | --- |
| | ν(C=O) | 1670, 1650, 1530 cm⁻¹ |
| | ν(C=C) | 1620 cm⁻¹ |
| ¹H-NMR-Spectrum (CDCl₃): | 1.40-1.75(4H, m, C—CH₂—CH₂—C) | |
| | 2.21(6H, s, CH₃) | |
| | 2.25-2.75(6H, m, NCH₂) | |
| | 3.20-3.55(2H, m, CONHCH₂) | |
| | 4.39(1H, s, Ar₂CH) | |
| | 6.43(1H, d, CH=CHCO, J=15.7Hz) | |
| | 7.00-7.55(12H, m, Ar, Py, NH) | |
| | 7.60(1H, d, CH=CHCO, J=15.7Hz) | |
| | 7.65-7.85(1H, m, Py) | |
| | 8.50-8.60(1H, m, Py) | |
| | 8.65-8.80(1H, m, Py) | |

PRODUCTION OF THE STARTING SUBSTANCES

Example i 8,8-bis-(4-fluorophenyl)-octylamine a) 8-hydroxy-8,8-bis-(4-fluorophenyl)-octyl bromide 7.65 g (313.8 mmol) magnesium shavings are placed under protective gas atmosphere and 55.1 g (314.8 mmol) 4-bromofluorobenzene dissolved in 250 ml abs. THF are added dropwise so that the reaction mixture boils gently. After complete addition, the mixture is heated for 30 minutes under reflux, and, afterwards, the suspension is cooled.

While cooling in an ice bath, a solution of 25.0 g (105.4 mmol) 8-bromoctanoic acid methyl ester in 100 ml abs. THF is added dropwise. Subsequently, the mixture is heated for a further 30 minutes under reflux. After cooling, NH$_4$Cl-solution is added to the reaction and this is extracted by diisopropyl ether by shaking. The organic phase is washed with saturated NaCl solution, dried over sodium sulfate and the solvent is removed under vacuum. The residue is chromatographically purified over silica gel with petroleum ether/acetic acid ethyl ester (20/1 to 10/1): Yield 36.4 g (87%).

b) 8,8-bis-(4-fluorophenyl)-oct-7-enyl bromide 31.9 g (80 mmol) 8-hydroxy-8,8-bis-(4-fluorophenyl)-octyl bromide dissolved in toluene are added to 0.3 g toluene sulfonic acid and the mixture is subsequently heated for an hour with water separator under reflux. After withdraw of the solvent, the residue is chromatographically purified over silica gel with petroleum ether/acetic acid ethyl ester (90/1): Yield 28.6 g (94%).

c) 8,8-bis-(4-fluorophenyl)-octyl bromide 9.7 g (25.5 mmol) 8,8-bis-(4-fluorophenyl)-oct-7-enyl bromide are dissolved in 350 ml ethanol and added to 0.5 g palladium (5%) on activated carbon. The mixture is stirred under hydrogen atmosphere (ca. one hour) until the theoretical amount of hydrogen to be taken up is consumed. Subsequently, the mixture is filtered off from a catalyst and the solvent is removed under vacuum. The residue is chromatographically purified over silica gel with petroleum ether/acetic acid ethyl ester (80/1 to 40/1)): Yield 8.6 g (89%).

d) 2-[8,8-bis-(4-fluorophenyl)-octyl]-isoindol-1,3-dione 9.0 g (23.6 mmol) 8,8-bis-(4-fluorophenyl)-octyl bromide and 4.7 g (25.0 mmol) phthalide potassium salt are stirred in 80 ml DMF for two hours at 70° C. After cooling, the mixture is concentrated and extracted with acetic acid ethyl ester and NaCl solution by shaking. The organic phase is dried over sodium sulfate and the solvent is removed under vacuum. The residue is chromatographically purified over silica gel with petroleum ether/acetic acid ethyl ester (60/1 to 30/1): Yield 8.1 g (77%).

e) 8,8-bis-(4-fluorophenyl)-octylamine 8.1 g (18.1 mmol) 2-[8,8-bis-(4-fluorophenyl)-octyl]-isoindol-1,3-dione and 1.8 ml (37.0 mmol) hydrazine hydrate are heated under reflux in 50 ml ethanol for two hours. The cooled solution is concentrated under vacuum and the residue is purified by chromatography over silica gel with CHCl$_3$/CH$_3$OH/TEA (98/2/2): Yield 2.4 g (42%).

Example ii 6-(3,3-diphenyl-ureido)-hexylamine 8.0 g (69.0 mmol) hexamethylene diamine are dissolved in 20 ml dichloromethane and 10.0 g (42.3 mmol) N,N-diphenylcarbamide acid chloride dissolved in 20 ml dichloromethane are added dropwise under cooling. The mixture is stirred for 12 hours at RT and, subsequently 2M NaOH solution is added. The organic phase is washed with 30 ml water, dried over sodium sulfate and the solvent is removed under vacuum. The residue is chromatographically purified over silica gel with CHCl$_3$/CH$_3$OH/TEA. (95/5/0 bis 95/5/1): Yield 5.7 g (43%).

Example iii 4-(1-phenyl-1,2,4,5-tetrahydro-benzo[d]azepin-3-yl)-butylamine a) 2-[4-(1-phenyl-1,2,4,5-tetrahydro-benzo[d]azepin-3-yl)-butyl]-isoindol-1,3-dione 20.0 g (89.5 mmol) 1-phenyl-1,2,4,5-tetrahydrobenzo[d]azepine, 25.2 g (89.5 mmol) N-(4-bromobutyl)-phthalimide and 18.5 g (134.3 mmol) potassium carbonate are stirred in 200 ml DMF for 6 hours at 60° C. The mixture is concentrated under vacuum and the residue is distributed between 300 ml acetic acid ethyl ester and 100 ml water. The watery phase is extracted with 50 ml acetic acid ethyl ester and the combined organic phases are washed with water. The organic phase is dried over sodium sulfate and evaporated under vacuum until dried: Yield 39.5 g.

b) 4-(1-phenyl-1,2,4,5-tetrahydro-benzo[d]azepin-3-yl)-butylamine

The reaction of the phthalimide to the amine follows analogously to Example i)e).

Batch size: 38.0 g (<89.5 mmol) 2-[4-(1-phenyl-1,2,4,5-tetrahydro-benzo[d]azepin-3-yl)-butyl]-isoindol-1,3-dione and 8.7 ml (179 mmol) hydrazine hydrate in 200 ml ethanol. The reaction mixture is filtered and the filtrate is concentrated under vacuum. The residue is taken up in 400 ml dichloromethane and washed twice each with 50 ml 10% NaCH solution. The organic phase is dried over sodium sulfate and, subsequently, the solvent is removed under vacuum. The purification occurs chromatographically over silica gel with CHCl$_3$/CH$_3$OH/TEA (95/5/0 to 90/9/1): Yield 15.6 g (59%).

Example iv 8,8-diphenyloctylamine a) 8-hydroxy-8,8-diphenyloctyl bromide

The Grignard reaction occurs analogously to Example i)a).

Batch size: 16 g (658 mmol) magnesium shavings, 103 g (656 mmol) bromobenzene and 52 g (219 mmol) 8-bromooctanoic acid ester: Yield 66.5 g (84%).

b) 2-(8-hydroxy-8,8-diphenyl-octyl)-isoindol-1,3-dione

The production of the phthalimide occurs analogously to Example i)d).

Batch size: 66.0 g (183 mmol) 8-hydroxy-8,8-diphenyl-octyl bromide and 33.3 g (180 mmol) phthalimide potassium salt. The reaction time is increased to five hours.

The purification occurs by crystallization from 1-chlorobutane: Yield 60.6 g (79%).

c) 2-(8,8-diphenyl-oct-7-enyl)-isoindol-1,3-dione

The production of the double bond occurs analogously to Example i)b).

Batch size: 39.6 g (92.7 mmol) 2-(8-hydroxy-8,8-diphenyl-octyl)-isoindol-1,3-dione and 0.3 g toluene sulfonic acid. The accumulated crude product is further processed without further purification: Yield 37.9 g (100%).

d) 2-(8,8-diphenyl-octyl)-isoindol-1,3-dione

The hydration of the double bond occurs analogously to Example i)c).

Batch size: 20.0 g (48.9 mmol) 2-(8,8-diphenyl-oct-7-enyl)-isoindol-1,3-dione and 0,7 g palladium (5%) on activated carbon in ethanol/acetic acid ethyl ester (1/1).

The accumulated crude product is further processed without further purification: Yield 18.9 g (94%).

e) 8,8-diphenyl-octylamine

The reaction of the phthalimide to the amine occurs analogously to Example i)e).

Batch size: 18.5 g (45.0 mmol) 2-(8,8-diphenyl-octyl)-iso-indol-1,3-dione and 8.0 ml (160 mmol) hydrazine.hydrate in ethanol.

The reaction mixture is concentrated under vacuum. The residue is taken UD in 400 ml chloroform and washed twice each with 50 ml 10% NaOH solution. The organic phase is dried over sodium sulfate and, subsequently, the solvent is removed under vacuum. The accumulated crude product is further processed without further purification: Yield 12.6 g (100%).

Example v 8-hydroxy-8,8-diphenyl-octylamine

The reaction of the phthalimide to the amine occurs analogously to Example i)e).

Batch size: 10.0 g (23.4 mmol) 2-(8-hydroxy-8,8-diphenyl-octyl)-isoindol-1,3-dione and 2.5 ml (51.4 mmol) hydrazine.hydrate in ethanol.

The reaction mixture is concentrated under vacuum. The residue is taken UD in chloroform and washed twice each with 50 ml 10% NaOH solution. The organic phase is dried over sodium sulfate and subsequently, the solvent is removed under vacuum. The accumulated crude product is further purified without further processing: Yield 6.7 g (97%).

Example vi 4-(3,3-diphenyl-ureido)-butylamine

The reaction of the diamine occurs analogously to Example 21.

Batch size: 10.5 g (45.3 mmol) N,N-diphenylcarbamic acid chloride and 12.0 g (136.3 mmol) 1,4-diaminobutane in dichloromethane.

The purification occurs chromatographically on silica gel with CHCl$_3$/CH$_3$OH/NH$_4$OH (95/5/0 to 95/5/1): Yield 9.0 g (70%).

Example vii 4-(1H,3H-benzo[de]isoquinolin-2-yl)-butylamine a) 4-(1,3-dioxo-1H,3H-benzo[de]isoquinolin-2-yl)-butylamine 20 g (100.9 mmol) naphthalic acid anhydride and 9.9 g (111.0 mmol) 1,4-diaminobutane are stirred for 6 hours in 250 ml toluene at 80° C. After cooling, the reaction mixture is concentrated under vacuum, taken up in 200 ml water and extracted three times each with 300 ml chloroform. The combined organic phases are dried over sodium sulfate and the solvent is removed under vacuum. The residue is taken up in 150 ml acetic acid ethyl ester and the insoluble portion is filtered off. The solvent is removed under vacuum and the accumulated crude product is further processed without further purification: Yield 13.0 g (48%).

b) 4-(1H,3H-benzo[de]isoquinolin-2-yl)-butylamine 5.0 g (18.6 mmol) 4-(1,3-dioxo-1H,3H-benzo[de]isoquinolin-2-yl)-butylamine are dissolved in 200 ml THF and 6.1 g (160.7 mmol) LiAlH$_4$ are added in portions under cooling. The suspension is stirred for 24 hours at RT and for 8 hours under reflux. After cooling, ethanol is carefully added dropwise until no more foam appears. The mixture is filtered and the filtrate is concentrated under vacuum. The residue is distributed between chloroform and water. The organic phase is dried over sodium sulfate and, after withdraw of the solvent, chromatographically purified over silica gel with CHCl$_3$/CH$_3$OH/NH$_4$OH (90/10/0.5 to 90/10/1): Yield 2.2 g (49%).

Example viii 6-(10,11-dihydro-dibenzo[b,f]azepin-5-yl-carbonylamino)-hexylamine.hydrochloride a) N-[6-(10,11-dihydro-dibenzo[b,f]azepin-5-yl-carbonylamino)-hexyl]-carbamic acid tert-butyl ester 5.4 g (20.8 mmol) N,N-diphenylcarbamic acid chloride, 4.5 g (20.8 mmol) N-(tert-butoxycarbonyl)-1,6-diaminohexane and 2.1 g (20.6 mmol) TEA are dissolved in 80 ml dichloromethane and stirred at RT for 12 hours. Subsequently, the mixture is washed twice each with 50 ml water. The organic phase is dried over sodium sulfate and the solvent is removed under vacuum. The accumulated crude product is further processed without further purification: Yield 8.75 g (85%).

b) 6-(10,11-dihydro-dibenzo-[b,f]azepin-5-yl-carbonylamino)-hexylamine.hydrochloride 7.5 g (17.7 mmol) N-[6-(10,11-dihydro-dibenzo[b,f]azeoin-5-yl-carbonylamino)-hexyl]-carbamic acid tert-butyl ester are dissolved in 70 ml ethanol and, after addition of 3.8 ml (45 mmol) concentrated hydrochloric acid, heated for three hours under reflux. The cooled solution is concentrated under vacuum and the residue is crystallized from isopropanol: Yield 5.6 g (84%).

Example ix

6-(tosyl-amino)-hexylamine dihydrochloride a) N-[6-(tosyl-amino)-hexyl]-carbamic acid tert-butyl ester

The reaction of the amine occurs analogously to reaction viii)a).

Batch size: 6.7 g (35.1 mmol) toluene-4-sulfonyl chloride, 7.5 g (35.0 mmol) N-(tert-butoxycarbonyl)-1,6-diaminohexane and 3.6 g (35.6 mmol) TEA in 60 ml dichloromethane.

The accumulated crude product is further processed without further purification: Yield 13.5 g.

b) 6-(tosyl-amino)-hexylamine.dihydrochloride

The release of the amine occurs analogously to Example viii)b).

Batch size: 13.0 g (<35 mmol) N-[6-(tosyl-amino)-hexyl]-carbamic acid tert-butyl ester and 7.7 ml (93 mmol) concentrated hydrochloric acid in 100 ml ethanol.

The reaction mixture is heated for three hours under reflux. The accumulated crude product is further processed without further purification: Yield 9.8 g (80%).

Example x

N-(4-hydroxybutyl)-3-pyridin-3-yl-acrylamide a) 3-(pyridin-3-yl)-acrylic acid-(N-hydroxysuccinimide ester)

38,5 g (335 mmol) N-hydroxysuccinimide and 76.0 g (369 mmol) dicyclohexylcarbodiimide are dissolved in 700 ml dioxane and 50.0 g (335 mmol) 3-(3-pyridyl)-acrylic acid are added. The suspension is stirred at RT for 20 hours. The mixture is filtered and the filtrate is concentrated under vacuum. The residue is crystallized twice each from 400 ml isopropanol: Yield 36.2 g (44%).

b) N-(4-hydroxybutyl)-3-pyridin-3-yl-acrylamide 19 g (77,1 mmol) 3-(pyridin-3-yl)-acrylic acid-(N-hydroxysuccin-imide ester) are dissolved in 200 ml THF and 6.9 g (77.1 mmol) 4-amino-1-butanol are added. The mixture is stirred at RT for three days. After withdraw of the solvent the residue is chromatographically purified over silica gel with $CHCl_3/CH_3OH$ (90/10): Yield 10.7 g (63%).

Example xi

6-hydroxy-6,6-diphenyl-hexylamine a) 6-hydroxy-6,6-diphenyl-hexyl bromide

The Grignard reaction occurs analogously to Example i) a).

Batch size: 6.6 g (272.7 mmol) magnesium shavings, 42.8 g (272.7 mmol) bromobenzene and 19 g (90.9 mmol) 6-bromohexanoic acid methyl ester in 360 ml THF.

In the work-up, dichloromethane is used for extraction. The purification occurs by chromatography on silica gel with dichloromethane: Yield 23.8 g (78%).

b) 2-(6-hydroxy-6,6-diphenyl-hexyl)-isoindol-1,3-dione

The production of the phthalimide occurs analogously to Example i)d).

Batch size: 23.8 g (71.4 mmol) 6-hydroxy-6,6-diphenyl-hexylbromide and 13.2 g (71.4 mmol) phthalimide.potassium salt in 150 ml DMF.

The reaction time is increased to 6 hours at 70° C. In the work-up, the mixture is distributed between chloroform and water. The purification occurs by chromatography on silica gel with $CHCl_3/CH_3CH$ (99/1): Yield 20.2 g (70%).

c) 6-hydroxy-6,6-diphenyl-hexylamine

The reaction of the phthalimide to the amine occurs analogously to Example i)e)

Batch size: 8.0 g (20.0 mmol) 2-(6-hydroxy-6,6-d phenyl-hexyl)-isoindol-1,3-dione and 2. g (40.0 mmol) hydrazine hydrate in 80 ml ethanol.

The reaction mixture is filtered and the filtrate is concentrated under vacuum. The residue is taken up in 180 ml dichloromethane and washed twice each with 20 ml 10% NaOH solution. The organic phase is dried over sodium sulfate and, subsequently, the solvent is removed under vacuum. The accumulated crude product is crystallized from 12 ml acetic acid ethyl ester: Yield 4.4 g (81%).

Example xii

6,6-diphenyl-hex-5-enylamine a) 2-(6,6-diphenyl-hex-5-enyl)-isoindol-1,3-dione

Die production of the double bond occurs analogously to Example i)b).

Batch size: 11.6 g (29.0 mmol) 2-(6-hydroxy-6,6-diphenyl-hexyl)-isoindol-1,3-dione and 0,3 g p-toluenesulfonic acid in 25 ml toluene.

The accumulated crude product is crystallized from 23 ml acetic acid ethyl ester: Yield 8.0 g (72%).

b) 6,6-d-phenyl-hex-5-enyl amine

The reaction of the phthalimide to the amine occurs analogously to Example i)e).

Batch size: 7.8 g (20. mmol) 2-(6,6-diphenyl-hex-5-enyl)-isoindol-1,3-dione and 2.0 g (40.0 mmol) hydrazine.hydrate in 80 ml ethanol.

The reaction mixture is filtered and the filtrate is concentrated under vacuum. The residue is taken up in 120 ml acetic acid ethyl ester and washed twice each with 10 ml 10% NaOH solution. The organic phase is dried over sodium sulfate and subsequently the solvent is removed under vacuum. The accumulated crude product is further processed without further purification: Yield 4.0 g (78%).

Example xiii

4-(4,5-diphenylimidazol-1-yl)-butylamine a) 2-[4-(4,5-diphenylimidazol-1-yl)-butyl]-isoindol-1,3-dione 1.7 g (70.8 mmol) sodium hydride are placed in 130 ml DMF and 1.0 g (54.5 mmol) 4,5-diphenylimidazole are added under cooling. The suspension is stirred for four hours at RT and, subsequently, 15.4 g (54.5 mmol) N-(4-bromobutyl)-phthalimide dissolved in DMF is added dropwise under cooling. After complete addition, the reaction mixture is stirred for 12 hours at RT, 18 ml methanol are carefully added dropwise and the suspension is filtered. The filtrate is concentrated under vacuum and the residue is distributed between 500 ml chloroform and 170 ml water. The organic phase is dried over sodium sulfate and evaporated under vacuum until dry dried. The residue is purified by chromatography on silica gel with $CHCl_3/CH_3OH$ (95/5) and subsequently crystallized from methanol: Yield 16.5 g (72%).

b) 4-(4,5-diphenyl-imidazol-1-yl)-butylamine

The reaction of the phthalimide to the amine occurs analogously to Example i)e).

Batch size: 14.0 g (33.2 mmol) 2-[4-(4,5-diphenyl-imidazol-1-yl)-butyl]-isoindol-1,3-dione and 3.3 ml (66.4 mmol) hydrazine hydrate in 130 ml ethanol.

The reaction mixture is filtered and the filtrate is concentrated under vacuum. The residue is taken up in 250 ml chloroform and washed twice each with 25 ml 10% NaOH solution. The organic phase is dried over sodium sulfate and, subsequently, the solvent is removed under vacuum. The accumulated crude product is further processed without further purification: Yield 9.0 g (93%).

Example xiv

4-(trans-2-phenyl-cyclopropyl-carbonylamino)-butylamine hydrochloride a) N-[4-(trans-2-phenyl-cyclopropyl-carbonylamino)-butyl]-carbamic acid tert-butyl ester The reaction of the amine occurs analogously to reaction viii)a).

Batch size: 5.0 g (25.6 mmol) trans-2-phenylcyclopropane-1-carboxylic acid chloride, 4.8 g (25.6 mmol) N-(tert-butoxycarbonyl)-1,4-diaminobutane and 2.6 g (25.6 mmol) TEA in 60 ml dichloromethane.

In the work-up, the organic phase is first washed with 30 ml 10% NaOH solution and then twice each with 50 ml water. The purification occurs b, chromatography on silica gel $CHCl^3/CH_3OH$ (99/1). Yield 8.25 g (93%).

b) 4-(trans-2-phenyl-cyclopropyl-carbonylamino)-butyl-amine.hydrochloride

The release of the amine occurs analogously to Example viii)b).

Batch size: 7.5 g (21.6 mmol) N-[4-(trans-2-phenyl-cyclopro-pyl-carbonylamino)-butyl]-carbamic acid tert-butyl ester and 6.4 ml (77 mmol) concentrated hydrochloric acid in 150 ml ethanol.

The reaction mixture is heated for 6 hours under reflux. The accumulated crude product is further processed without further purification: Yield 5.3 g (80%).

Example xv

5-hydroxy-5,5-diphenyl-pentylamine a) 5-hydroxy-5,5-diphenyl-pentyl bromide

Die Grignard reaction occurs analogously to Example i)a).

Batch size: 9.3 g (382. mmol) magnesium shavings, 60.0 g (382.1 mmol) bromobenzene and 20.1 ml (127.4 mmol) ethyl 5-bromovalerate acid-ethylester in 510 ml THF.

In the work-up, dichloromethane is used for extraction. The purification occurs by chromatography on silica gel with chloroform: Yield 26.2 g (64%).

b) 2-(5-hydroxy-5,5-diphenyl-pentyl)-isoindol-1,3-dione

The production of the phthalimide occurs analogously to Example i)d).

Batch size: 26.0 g (81.4 mmol) 5-hydroxy-5,5-diphenyl-pentyl bromide and 15.1 g (81.4 mmol) phthalimide potassium salt in 170 ml DMF.

The reaction time is increased to 6 hours at 70° C. In the work-up, the mixture is distributed between chloroform and water. The purification occurs by chromatography on silica gel with chloroform: Yield 14.9 g (48%).

c) 5-hydroxy-5,5-diphenyl-pentylamine

The reaction of the phthalimide to the amine occurs analogously to Example i)e).

Batch size: 5.0 g (13.0 mmol) 2-(5-hydroxy-5,5-diphenyl-pentyl)-isoindol-1,3-dione and 1.3 g (26.0 mmol) hydrazine hydrate in 50 ml ethanol.

The reaction mixture is filtered and the filtrate is concentrated under vacuum. The residue is taken up in 120 ml chloroform and washed twice each with 10 ml 10% NaOH solution. The organic phase is dried over sodium sulfate and, subsequently, the solvent is removed under vacuum. The accumulated crude product is further processed without further purification: Yield 2.4 g (72%).

Example xvi

7-phenyl-heptylamine a) 2-(7-phenylheptyl)-isoindol-1,3-dione b)

Production analogous to Example 10.

Batch size: 10.0 g (52.0 mmol) 7-phenyl-heptanol, 13.6 g (5.0 mmol) triphenylphosphine, 7.7 g (52.0 mmol) phthalimide and 8.2 ml (52.0 mmol) azodicarboxylic acid diethyl ester in 200 ml THF.

The purification occurs by chromatography on silica gel with dichloromethane: Yield 11.2 g (67%).

b) 7-phenylheptylamine

The reaction of the phthalimide to the amine occurs analogously to Example i)e).

Batch size: 11.0 g (34.2 mmol) 2-(7-phenyl-heptyl)-isoindol-1,3-dione and 3.4 g (68.4 mmol) hydrazine.hydrate in 100 ml ethanol.

The reaction mixture is filtered and the filtrate is concentrated under vacuum. The residue is taken up in 300 ml chloroform and washed twice each with 20 ml 10% NaOH solution. The organic phase is dried over sodium sulfate and, subsequently, the solvent is removed under vacuum. The accumulated crude product is further-processed without further purification: Yield 6.1 g (93%).

Example xvii

4-diphenylacetylamino-butylamine.hydrochloride a) N-(4-diphenylacetylamino-butyl)-carbamic acid tert-butyl ester

The reaction of the amine occurs analogously to reaction viii)a).

Batch size: 4.6 g (19.9 mmol) diphenylchloroacetyl chloride, 3.8 g (20.2 mmol) N-(tert-butoxycarbonyl)-1,4-diaminobutane and 2.1 g (20.7 mmol) TEA in 60 ml dichloromethane.

The purification occurs by crystallization from isopropanol: Yield 5.5 g (72%).

b) 4-diphenylacetylamino-butylamine.hydrochloride

The release of the amine occurs analogously to Example viii)b).

Batch size: 5.5 g (14.4 mmol) N-(4-diphenylacetylamino-butyl)-carbamic acid tert-butyl ester and 4.1 ml (49 mmol) concentrated hydrochloric acid in 60 ml ethanol.

The reaction mixture is heated for three hours under reflux. The accumulated crude product is further processed without further purification: Yield 4.2 g (90%).

Example xviii

4-(benzhydryl-amino)-butylamine a) N-[4-(benzhydryl-amino)-butyl]-carbamic acid tert-butyl ester 5.0 g (26.6 mmol) N-(tert-butoxycarbonyl)-1,4-diaminobutane 5.5 g (39.8 mmol) potassium carbonate and 0.9 g (5.3 mmol) potassium iodide are placed in 50 ml DMF and 6.6 g (26.6 mmol) benzhydryl bromide are added dropwise at RT. The mixture is stirred for 12 hours at 70° C. and the suspension is filtered after cooling and the filtrate is concentrated under vacuum. The residue is taken up in 200 ml chloroform and washed with 100 ml water. The organic phase is dried over sodium sulfate and, subsequently, the solvent is removed under vacuum. The accumulated crude product is further processed without further purification: Yield 10.8 g.

b) 4-(benzhydryl-amino)-butylamine

The release of the amine occurs analogously to Example viii)b).

Batch size: 4.6 g (<11.3 mmol) N-[4-(benzhydryl-amino)-butyl]-carbamic acid tert-butyl ester and 5.2 ml (63 mmol) concentrated hydrochloric acid in 50 methanol.

The reaction mixture is stirred at RT for 12 hours, subsequently concentrated under vacuum and the residue is distributed between 80 ml chloroform and 80 ml water. The aqueous phase is made alkaline with 30% sodium hydroxide solution and extracted twice each with 50 ml chloroform by shaking. The combined organic phases are dried over sodium sulfate and subsequently, the solvent is removed under vacuum. The accumulated crude product is further processed without further purification: Yield 1.7 g (58%).

Example xix

4-{[2-(benzhydryl-methylamino)-ethyl]-methylamino}-butylamine a) N1-benzhydryl-N1,N2-dimethyl-ethan-1,2-diamine 15.1 g (171 mmol) N,N'-dimethylethylenediamine, 35 g (255 mmol) potassium carbonate are placed in 250 ml DMF and 30.9 g (125 mmol) benzhydryl bromide are added dropwise at RT. The mixture is concentrated under vacuum. The residue is taken up in chloroform and washed with water. The organic phase is dried over sodium sulfate and the solvent is removed under vacuum. The purification occurs by chromatography on silica gel with chloroform: Yield 14.5 g (45%).

b) 2-(4-{[2-(benzhydryl-methyl-amino)-ethyl]-methylamino}-butyl)-isoindol-1,3-dione 13.9 g (54,7 mmol) N1-benzhydryl-N1,N2-dimethyl-ethan-1,2-diamine, 15.4 g (54.7 mmol) N-(4-bromobutyl)-phthalimide, 15.1 g (109.5 mmol) potassium carbonate and 1.6 g (10.6 mmol) sodium iodide are stirred for four hours in DMF at 70° C. After cooling, the mixture is concentrated under vacuum and the residue is distributed between chloroform and water. The organic phase is dried over sodium sulfate and evaporated under vacuum until dry. The purification occurs by chromatography on silica gel with $CHCl_3$/$CH_3OH$ (100/0 to 99/1): Yield 20.8 g (83%).

c) 4-{[2-(benzhydryl-methylamino)-ethyl]-methylamino}-butylamine

The reaction of the phthalimide to the amine occurs analogously to Example i)e).

Batch size: 20.8 g (45.6 mmol) 2-(4-{[2-(benzhydryl-methyl-amino)-ethyl]-methylamino}-butyl)-isoindol-1,3-dione and 4.6 g (91.9 mmol) hydrazine.hydrate in 200 ml ethanol.

The reaction mixture is filtered and the filtrate is concentrated under vacuum. The residue is taken up in acetic acid ethyl ester and washed with 10% NaOH solution. The organic phase is dried over sodium sulfate and subsequently, the solvent is removed under vacuum. The accumulated crude product is further processed without further purification: Yield 10.9 g (73%).

In the following Table a series of Examples for the end products according to the invention are listed:

TABLE 1
Exemplifying compounds of formula (I) according to the invention
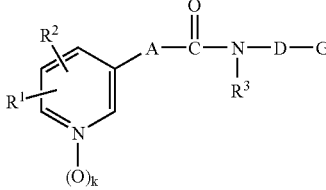
| Nr | R¹, R² | k | A | R³ | D—G |
|----|--------|---|---|----|----|
| 1 | H | 0 | CH=CH | H | (CH$_2$)$_6$—C$_6$H$_5$ |
| 2 | H | 0 | CH$_2$CH$_2$ | H | (CH$_2$)$_7$—C$_6$H$_5$ |
| 3 | H | 0 | CH=CH | H | " |
| 4 | H | 0 | CH=CH | H | 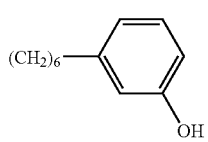 |
| 5 | H | 0 | CH$_2$CH$_2$ | H | 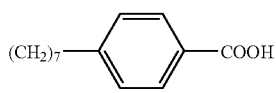 |
| 6 | H | 0 | CH=CH | H | 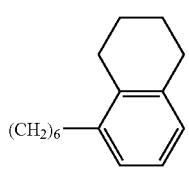 |
| 7 | H | 0 | CH=CH | H | 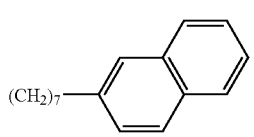 |
| 8 | H | 0 | CH=C(CH$_3$) | H | 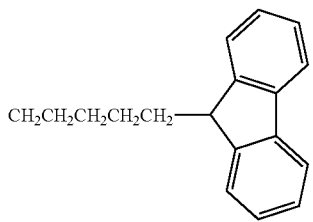 |
| 9 | H | 0 | CH$_2$CH$_2$ | H | 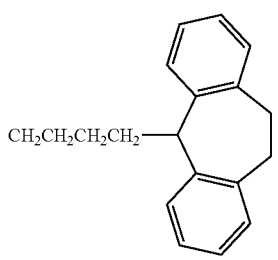 |
| 10 | H | 0 | CH=CH | H | " |
| 11 | 6-CH$_3$ | 0 | CH=CH | H | 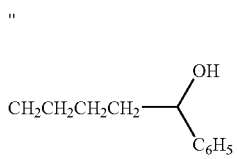 |

TABLE 1-continued

Exemplifying compounds of formula (I) according to the invention

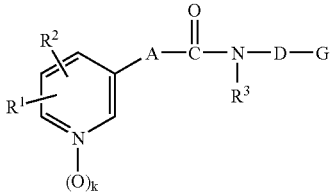

| Nr | R¹, R² | k | A | R³ | D—G |
|---|---|---|---|---|---|
| 12 | H | 0 | CH=CH | H | $(CH_2)_7$—CH(C$_6$H$_5$)—CH$_3$ |
| 13 | H | 0 | CH=CH | H | CH$_2$CH$_2$CH$_2$CH$_2$—CH(C$_6$H$_5$)(cyclopropyl) |
| 14 | H | 0 | CH$_2$CH$_2$ | H | CH$_2$CH$_2$CH$_2$CH$_2$—CH(C$_6$H$_5$)$_2$ |
| 15 | H | 0 | CH=CH | H | $(CH_2)_6$—CH(C$_6$H$_5$)$_2$ |
| 16 | H | 0 | CH$_2$CH$_2$ | H | $(CH_2)_7$—CH(C$_6$H$_5$)$_2$ |
| 17 | H | 0 | CH=CH | H | " |
| 18 | H | 0 | CH=CH | CH$_3$ | CH$_2$CH$_2$N(CH$_3$)—C(=O)—NHCH$_2$CH$_2$—CH(C$_6$H$_5$)$_2$ |
| 19 | H | 0 | CH$_2$CH$_2$ | H | CH$_2$CH$_2$CH$_2$CH$_2$CH$_2$—CH(C$_6$H$_5$)(4-Br-C$_6$H$_4$) |
| 20 | H | 0 | CH=CH | H | $(CH_2)_6$—CH(C$_6$H$_5$)(4-COOH-C$_6$H$_4$) |

TABLE 1-continued
Exemplifying compounds of formula (I) according to the invention
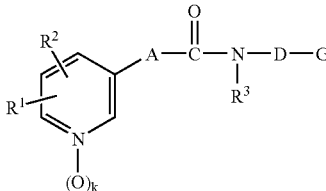
| Nr | R¹, R² | k | A | R³ | D—G |
|----|--------|---|------|-------|-----|
| 21 | H | 0 | CH=CH | H | 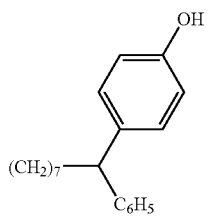 |
| 22 | H | 0 | CH=CH | H | 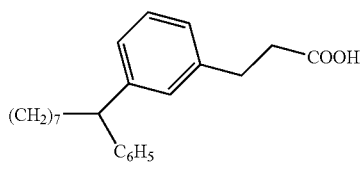 |
| 23 | H | 0 | CH=CH | H | 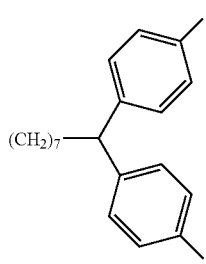 |
| 24 | H | 0 | CH₂CH₂ | H | 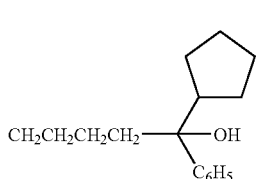 |
| 25 | H | 0 | CH=CH | H | 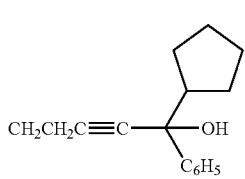 |
| 26 | H | 0 | OCH₂ | H | 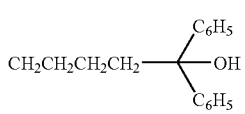 |
| 27 | H | 0 | CH=CH | H | " |
| 28 | 5-F | 0 | CH=CH | H | " |
| 29 | H | 0 | CH=CH | C₂H₅ | " |
| 30 | H | 0 | CH=CH | H | 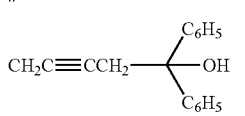 |

TABLE 1-continued

Exemplifying compounds of formula (I) according to the invention

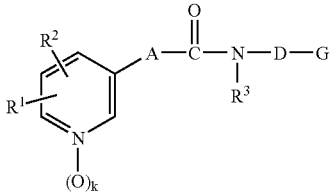

| Nr | R¹, R² | k | A | R³ | D—G |
|----|--------|---|---|-----|-----|
| 31 | H | 0 | CH=CH | H | CH₂CH₂CH₂CH₂CH₂—C(C₆H₅)(C₆H₅)—OH |
| 32 | 6-C₂H₅S | 0 | CH=CH | H | " |
| 33 | H | 1 | CH=CH | H | " |
| 34 | H | 0 | △ | H | " |
| 35 | H | 0 | CH₂CH₂CH₂CH₂ | H | " |
| 36 | H | 0 | CH₂CH₂ | H | CH₂CH₂OCH₂CH₂—C(C₆H₅)(C₆H₅)—OH |
| 37 | H | 0 | CH=CH | H | (CH₂)₆—C(C₆H₅)(C₆H₅)—OH |
| 38 | H | 0 | CH=CH | CH₂—CH=CH₂ | " |
| 39 | H | 0 | C≡C | H | " |
| 40 | H | 0 | SCH₂ | H | (CH₂)₇—C(C₆H₅)(C₆H₅)—OH |
| 41 | H | 0 | CH=CH | H | " |
| 42 | H | 0 | CH=CH | H | (CH₂)₉—C(C₆H₅)(C₆H₅)—OH |
| 43 | H | 0 | CH=CH | H | CH₂CH₂CH₂CH₂CH₂—C(o-H₂N-C₆H₄)(C₆H₅)—OH |
| 44 | H | 0 | CH₂CH₂ | H | (p-HOOC-CH₂CH₂-C₆H₄)-CH₂CH₂CH₂CH₂CH₂—C(C₆H₅)—OH |

TABLE 1-continued
Exemplifying compounds of formula (I) according to the invention
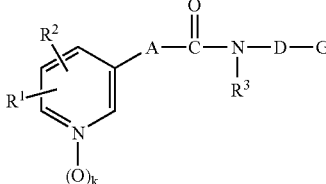
| Nr | R¹, R² | k | A | R³ | D—G |
|----|--------|---|---|-----|-----|
| 45 | H | 0 | CH=CH | H | 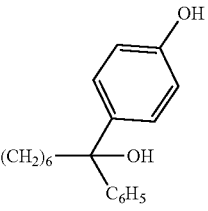 |
| 46 | H | 0 | CH=CH | H | 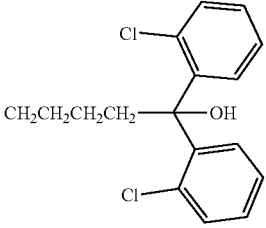 |
| 47 | H | 0 | $CH_2CH_2$ | H | 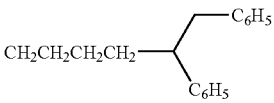 |
| 48 | H | 0 | CH=CH | H | 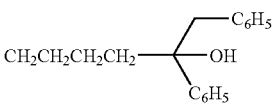 |
| 49 | H | 0 | $OCH_2$ | H | 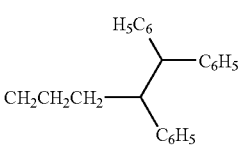 |
| 50 | H | 0 | $\underset{CH_3}{C}=CH$ | H | " |
| 51 | H | 0 | $CH_2CH_2$ | H |  |
| 52 | H | 0 | CH=CH—CH=CH | H | " |
| 53 | H | 0 | CH=CH | H | 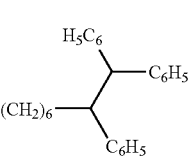 |

TABLE 1-continued
Exemplifying compounds of formula (I) according to the invention
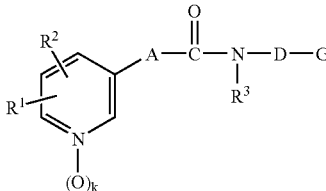
| Nr | R¹, R² | k | A | R³ | D—G |
|---|---|---|---|---|---|
| 54 | H | 0 | CH=CH | H | 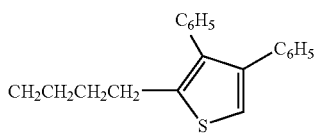 |
| 55 | H | 0 | SCH$_2$ | H | 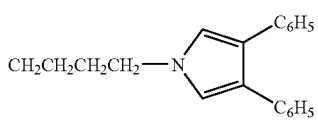 |
| 56 | 5-Cl | 0 | CH=CH | H | " |
| 57 | H | 0 | CH$_2$CH$_2$ | H | 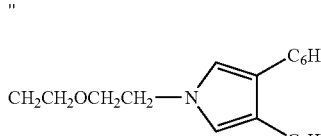 |
| 58 | H | 0 | CH=CH | H | 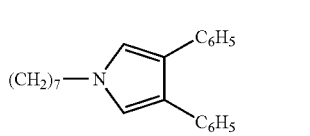 |
| 59 | H | 0 | CH=CH | H | 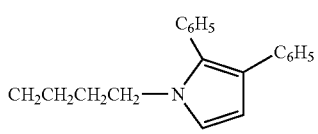 |
| 60 | H | 0 | CH$_2$CH$_2$CH$_2$CH$_2$ | H | 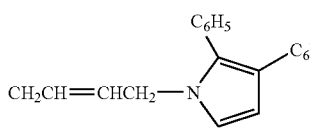 |
| 61 | H | 0 | CH$_2$ | H | 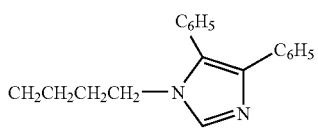 |
| 62 | H | 0 | OCH$_2$ | H | " |
| 63 | H | 0 | CH=CH | H | " |
| 64 | H | 1 | CH=CH | H | " |
| 65 | 2-CF$_3$ | 0 | CH=CH | H | " |
| 66 | H | 0 | CH=CH |  | " |
| 67 | H | 0 | C≡C | H | " |
| 68 | H | 0 | CH=CH | H | 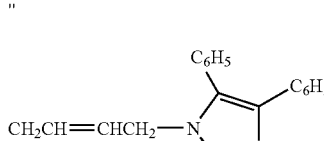 |

TABLE 1-continued

Exemplifying compounds of formula (I) according to the invention

| Nr | R¹, R² | k | A | R³ | D—G |
|---|---|---|---|---|---|
| 69 | H | 0 | CHCF$_2$ / OH | H | OCH$_2$CH$_2$CH$_2$—N(imidazole with C$_6$H$_5$, C$_6$H$_5$) |
| 70 | H | 0 | CH=CH | H | CH$_2$CH$_2$CHCH$_2$—N(imidazole with C$_6$H$_5$, C$_6$H$_5$) / OH |
| 71 | H | 0 | CH$_2$CH$_2$ | H | CH$_2$CH$_2$CH$_2$CH$_2$CH$_2$—N(imidazole with C$_6$H$_5$, C$_6$H$_5$) |
| 72 | H | 0 | OCH$_2$ | H | " |
| 73 | 2-Cl | 0 | CH=CH | H | (CH$_2$)$_6$—N(imidazole with C$_6$H$_5$, C$_6$H$_5$) |
| 74 | H | 0 | CHCH$_2$ / CH$_3$ | H | " |
| 75 | H | 0 | C≡C | H | " |
| 76 | H | 0 | CH$_2$CH$_2$ | H | CH$_2$CH$_2$C≡CCH$_2$CH$_2$—N(imidazole with C$_6$H$_5$, C$_6$H$_5$) |
| 77 | H | 0 | CH=CH | H | (CH$_2$)$_7$—N(imidazole with C$_6$H$_5$, C$_6$H$_5$) |
| 78 | H | 0 | CH=CH | H | CH$_2$CH$_2$NH—C(=O)—OCH$_2$CH$_2$—N(imidazole with C$_6$H$_5$, C$_6$H$_5$) |
| 79 | H | 0 | CH=CH | H | (CH$_2$)$_6$NH—C(=O)—CH$_2$CH$_2$—N(imidazole with C$_6$H$_5$, C$_6$H$_5$) |

TABLE 1-continued

Exemplifying compounds of formula (I) according to the invention

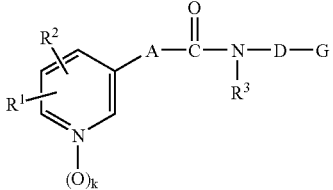

| Nr | R¹, R² | k | A | R³ | D—G |
|---|---|---|---|---|---|
| 80 | H | 0 | CH₂CH₂ | H | CH₂CH₂CH₂CH₂CH₂-(3-pyridyl) |
| 81 | H | 0 | CH=CH—CH=CH | H | CH₂CH₂CH₂-(3-indolyl) |
| 82 | H | 0 | CH₂CH₂ | H | CH₂CH₂CH₂CH₂-(1-benzimidazolyl) |
| 83 | H | 0 | CH=CH | H | " |
| 84 | 6-CH₃O | 0 | CH=CH | H | " |
| 85 | H | 0 | OCH₂ | H | (CH₂)₆-(1-benzimidazolyl) |
| 86 | H | 0 | CH=C(CH₃) | H | " |
| 87 | H | 0 | CH=CH | H | CH₂CH₂CH₂CH₂-(1-(2-oxo-benzimidazolyl)) |
| 88 | H | 0 | CH₂N(CH₃)CH₂ | H | " |
| 89 | H | 0 | OCH₂ | H | (CH₂)₈-(1-(2-oxo-benzimidazolyl)) |

TABLE 1-continued
Exemplifying compounds of formula (I) according to the invention
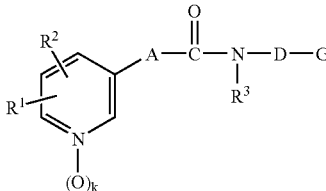
| Nr | R¹, R² | k | A | R³ | D—G |
|----|--------|---|---|-----|-----|
| 90 | H | 0 | CH=CH | H | 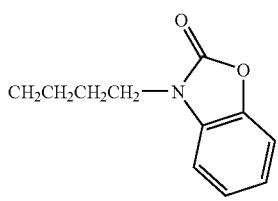 |
| 91 | 4-CF3 | 0 | CH=CH | H | 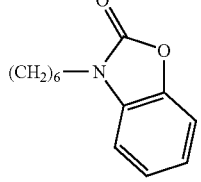 |
| 92 | H | 0 | SCH2 | H | 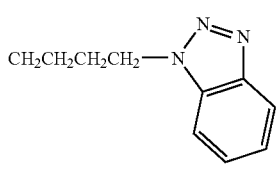 |
| 93 | H | 0 | CH=CH—CH=CH | H | " |
| 94 | H | 0 | CH₂CH₂ | H | 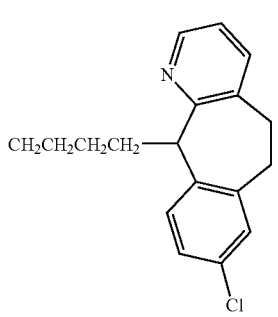 |
| 95 | H | 0 | C≡C | H | " |
| 96 | H | 0 | CH₂CH₂ | H | 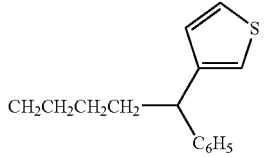 |
| 97 | H | 0 | OCH₂ | H | " |
| 98 | H | 0 | CH₂CH₂ | H | 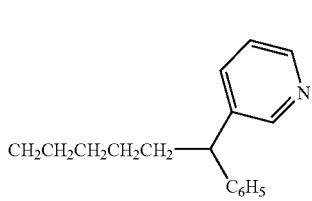 |

TABLE 1-continued

Exemplifying compounds of formula (I) according to the invention

| Nr | R¹, R² | k | A | R³ | D—G |
|---|---|---|---|---|---|
| 99 | H | 0 | CH=CH | H | " |
| 100 | H | 0 | CH=CH | H | (CH₂)₆—CH(2-thienyl)(2-thienyl) |
| 101 | H | 0 | CH₂CH(OH) | H | CH₂CH₂CH₂CH₂—C(OH)(2-thienyl)(2-thienyl) |
| 102 | H | 0 | CH=CH | H | " |
| 103 | H | 0 | OCH₂ | H | CH₂CH₂CH₂CH₂—C(OH)(C₆H₅)(3-furyl) |
| 104 | H | 0 | CH=CH | H | CH₂CH₂CH₂CH₂CH₂—C(OH)(C₆H₅)(4-pyridyl) |
| 105 | H | 0 | CH=CH—CH=CH | H | " |
| 106 | H | 0 | CH=CH | H | (CH₂)₆CH=CH—C₆H₅ |
| 107 | H | 0 | CH₂CH₂ | H | (CH₂)₅CH=(indenyl) |
| 108 | H | 0 | CH=CH | H | (CH₂)₄CH=(1-naphthyl) |

TABLE 1-continued

Exemplifying compounds of formula (I) according to the invention

| Nr | $R^1, R^2$ | k | A | $R^3$ | D—G |
|---|---|---|---|---|---|
| 109 | H | 0 | CH=C(C$_6$H$_5$) | H | (CH$_2$)$_4$CH=C(C$_6$H$_5$)(n-hexyl) |
| 110 | H | 0 | CH=CH | H | (CH$_2$)$_6$CH=C(C$_6$H$_5$)(cyclopropyl) |
| 111 | H | 0 | CH$_2$CH$_2$ | H | (CH$_2$)$_4$CH=C(C$_6$H$_5$)(cyclopentyl) |
| 112 | H | 0 | SCH$_2$ | H | " |
| 113 | H | 0 | CH=CH | H | CH$_2$CH$_2$CH=C(C$_6$H$_5$)$_2$ |
| 114 | 6-CH$_3$ | 0 | CH$_2$CH$_2$ | H | CH$_2$CH$_2$CH$_2$CH=C(C$_6$H$_5$)$_2$ |
| 115 | H | 0 | CH=CH | H | " |
| 116 | 5-Br | 0 | CH=CH | H | " |
| 117 | H | 0 | CH$_2$CH$_2$ | H | (CH$_2$)$_4$CH=C(C$_6$H$_5$)$_2$ |
| 118 | H | 0 | SCH$_2$ | H | " |
| 119 | H | 0 | CH$_2$C(=O) | H | " |
| 120 | H | 0 | CH=CH | H | " |
| 121 | 6-CF$_3$ | 0 | CH=CH | H | " |
| 122 | H | 0 | CH=CH | CH$_3$ | " |
| 123 | H | 0 | C≡C | H | " |
| 124 | H | 0 | cyclopropyl | H | " |
| 125 | H | 0 | (CH=CH)$_3$ | H | " |
| 126 | H | 0 | CH$_2$CHF | H | (CH$_2$)$_5$CH=C(C$_6$H$_5$)$_2$ |

TABLE 1-continued
Exemplifying compounds of formula (I) according to the invention
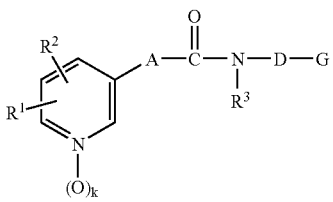
| Nr | R¹, R² | k | A | R³ | D—G |
|---|---|---|---|---|---|
| 127 | H | 0 | CH=CH | H | " |
| 128 | 2-Cl | 0 | CH=CH | H | " |
| 129 | H | 0 | CH=CH | CH₂–CH=CH₂ | " |
| 130 | H | 0 | CH₂CH₂CH₂CH₂ | H | " |
| 131 | H | 0 | CH=CH | H | (CH₂)₈CH=C(C₆H₅)₂ |
| 132 | H | 0 | CH=CH | H | CH₂CH₂CH₂CH=C(C₆H₅)(4-HOC₆H₄) |
| 133 | H | 0 | CH=CH | H | (CH₂)₄CH=C(C₆H₅)(4-BrC₆H₄) |
| 134 | H | 0 | CH₂CH₂ | H | (CH₂)₄CH=C(C₆H₅)(2-H₂NC₆H₄) |
| 135 | H | 0 | CH=CH | H | (CH₂)₄CH=C(C₆H₅)(4-HOOCC₆H₄) |

TABLE 1-continued
Exemplifying compounds of formula (I) according to the invention
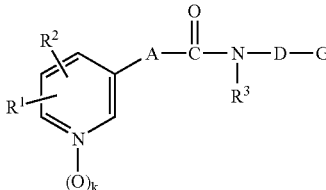
| Nr | R¹, R² | k | A | R³ | D—G |
|---|---|---|---|---|---|
| 136 | H | 0 | CH=CH | H | 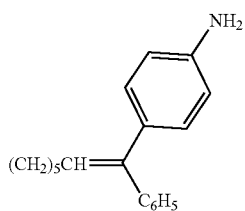 |
| 137 | H | 0 | CH$_2$CH$_2$ | H | 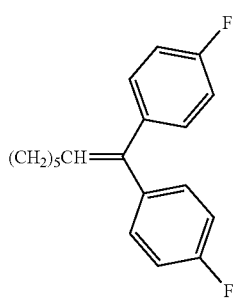 |
| 138 | H | 0 | CH=CH | H | 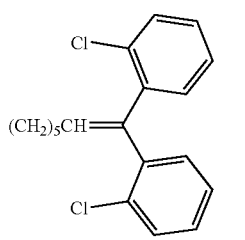 |
| 139 | H | 0 | CH$_2$CH$_2$ | H | 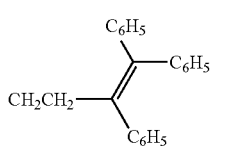 |
| 140 | H | 0 | CH$_2$CH<br>\|<br>CH$_3$ | H | 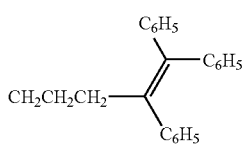 |
| 141 | H | 0 | CH=CH | H | " |
| 142 | H | 0 | OCH$_2$ | H | 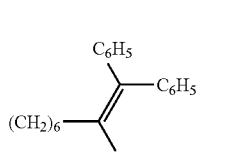 |
| 143 | H | 0 | CH=CH | H | " |

TABLE 1-continued
Exemplifying compounds of formula (I) according to the invention
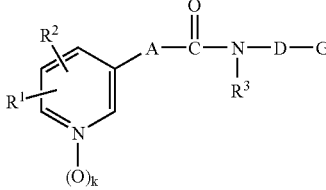
| Nr | R¹, R² | k | A | R³ | D—G |
|---|---|---|---|---|---|
| 144 | H | 0 | CH=CH | H | 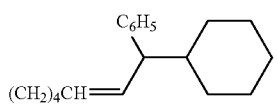 |
| 145 | H | 0 | CH$_2$CH$_2$ | H | 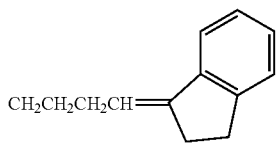 |
| 146 | H | 0 | CH=C<br>  \|<br>  C$_6$H$_5$ | H | " |
| 147 | H | 0 | CH=CH—CH=CH | H | " |
| 148 | H | 0 | CHCF$_2$<br>  \|<br>  OH | H | 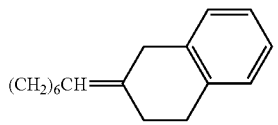 |
| 149 | H | 0 | CH=CH | H | " |
| 150 | H | 0 | CH=CH | H | 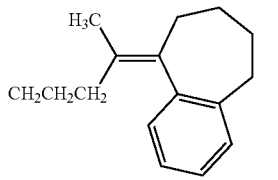 |
| 151 | 2-Cl | 0 | CH=CH | H | " |
| 152 | H | 0 | CH$_2$CH$_2$ | H | 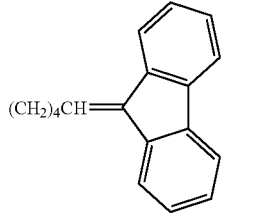 |
| 153 | H | 0 | CH$_2$CHF | H | " |
| 154 | H | 0 | CCH$_2$<br>  \|\|<br>  O | H | " |
| 155 | H | 0 | CH=CH | H | " |
| 156 | H | 0 | CH=CH | CH$_2$CH$_3$ | " |
| 157 | H | 0 | C≡C | H | " |
| 158 | H | 0 |  | H | " |

TABLE 1-continued

Exemplifying compounds of formula (I) according to the invention

| Nr | R¹, R² | k | A | R³ | D—G |
|---|---|---|---|---|---|
| 159 | H | 0 | SCH$_2$ | H | (CH$_2$)$_6$CH=fluorenylidene |
| 160 | H | 0 | CH=CH | H | " |
| 161 | H | 0 | OCH$_2$ | H | (CH$_2$)$_4$CH=dihydroanthracenylidene |
| 162 | H | 0 | CH=CH | H | " |
| 163 | H | 0 | CH$_2$CH$_2$ | H | (CH$_2$)$_5$CH=dibenzosuberylidene |
| 164 | H | 0 | CH=CH | H | " |
| 165 | H | 0 | CH=CH—CH=CH | H | " |
| 166 | H | 0 | CH$_2$CH$_2$CH$_2$CH$_2$ | H | (CH$_2$)$_4$CH=indolyl |
| 167 | H | 0 | CH$_2$CH$_2$ | H | CH$_2$CH$_2$CH=C(C$_6$H$_5$)(thienyl) |
| 168 | H | 0 | CH=CH | H | " |

TABLE 1-continued
Exemplifying compounds of formula (I) according to the invention
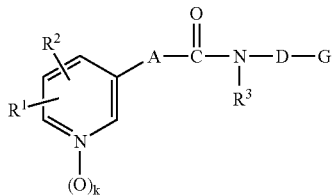
| Nr | R¹, R² | k | A | R³ | D—G |
|---|---|---|---|---|---|
| 169 | H | 0 | CH=CH | H | (CH₂)₄CH=C(C₆H₅)-thiazol-2-yl |
| 170 | H | 0 | SCH₂ | H | CH₂CH₂CH₂CH=C(C₆H₅)-pyridin-3-yl |
| 171 | H | 0 | CH₂CH₂ | H | (CH₂)₄CH=C(C₆H₅)-pyridin-2-yl |
| 172 | H | 0 | OCH₂CH₂ | H | " |
| 173 | H | 0 | CH=CH | H | (CH₂)₅CH=C(C₆H₅)-pyridin-2-yl |
| 174 | H | 0 | C≡C | H | " |
| 175 | H | 0 | CH=CH | H | (CH₂)₅CH=(1-methylindolin-3-ylidene) |
| 176 | H | 0 | CH₂CH₂ | H | (CH₂)₄CH=(2-oxoindolin-3-ylidene) |
| 177 | H | 0 | CH=CH—CH=CH | H | " |

TABLE 1-continued
Exemplifying compounds of formula (I) according to the invention
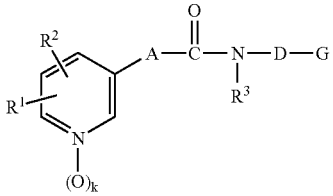
| Nr | R¹, R² | k | A | R³ | D—G |
|----|--------|---|---|-----|-----|
| 178 | H | 0 | OCH$_2$ | H | 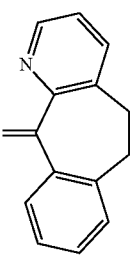 |
| 179 | H | 0 | CH=CH | H | " |
| 180 | H | 0 | CH=CH | H | 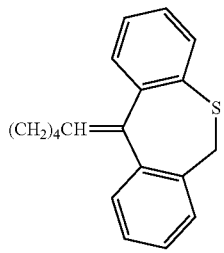 |
| 181 | H | 0 | CH$_2$CH$_2$CH$_2$CH$_2$ | H | " |
| 182 | H | 0 | SCH$_2$ | H | 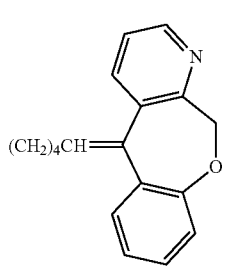 |
| 183 | H | 0 | CH=CH | H | " |
| 184 | H | 0 | CH=CH | H | 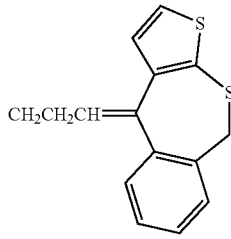 |

TABLE 1-continued

Exemplifying compounds of formula (I) according to the invention

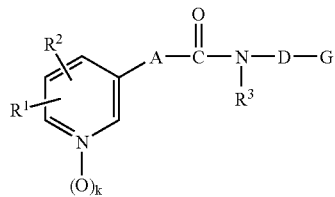

| Nr | R¹, R² | k | A | R³ | D—G |
|---|---|---|---|---|---|
| 185 | 5-CF₃ | 0 | CH=CH | H | |
| 186 | 6-C₂H₅S | 0 | CH=CH | H | " |
| 187 | H | 0 | CH=CH | H | CH₂CH₂CH₂CH₂—NH—CH(C₆H₅)(C₆H₅) |
| 188 | H | 0 | CH₂CH₂ | H | CH₂CH₂OCH₂CH₂—NH—CH(C₆H₅)(C₆H₅) |
| 189 | H | 0 | CH=CH—CH=CH | H | CH₂CH₂CH₂CH₂—NH—C(C₆H₅)₃ |
| 190 | H | 0 | CH=CH | H | CH₂CH(OH)CH₂—NH—C(C₆H₅)₃ |
| 191 | H | 0 | CH=CH | H | (CH₂)₈—NH—C(C₆H₅)₃ |
| 192 | H | 0 | CH₂CH₂CH₂CH₂ | H | CH₂C≡CCH₂—NH—CH(CH₃CH₂)(CH₂CH₂C₆H₅) |
| 193 | H | 0 | CH=CH | H | CH₂CH₂CH₂CH₂N(CH₃)CH₂CH₂—N(CH₃)—CH(C₆H₅)(C₆H₅) |
| 194 | H | 0 | OCH₂ | H | CH₂CH₂CH₂CH₂—N(CH₂C₆H₅)(C₆H₅) |

TABLE 1-continued
Exemplifying compounds of formula (I) according to the invention
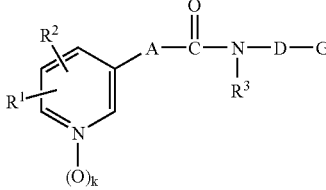
| Nr | R¹, R² | k | A | R³ | D—G |
|---|---|---|---|---|---|
| 195 | H | 0 | CH=CH | H |  |
| 196 | H | 0 | CH=CH | H | 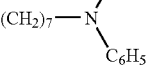 |
| 197 | H | 0 | CH=CH | H |  |
| 198 | H | 0 | CH$_2$CH$_2$ | H | 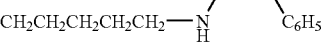 |
| 199 | H | 0 | CH=C(C$_6$H$_5$) | H | " |
| 200 | H | 0 | CH$_2$CH(OH) | H | 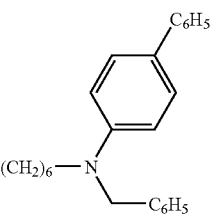 |
| 201 | H | 0 | CH=CH | H | " |
| 202 | H | 0 | CH=CH—CH=CH | H | " |
| 203 | H | 0 | CH$_2$CH$_2$ | H | 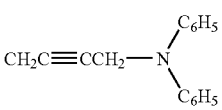 |
| 204 | H | 0 | CH=CH | H | " |
| 205 | H | 0 | CH$_2$CH$_2$ | H | 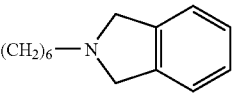 |

TABLE 1-continued
Exemplifying compounds of formula (I) according to the invention
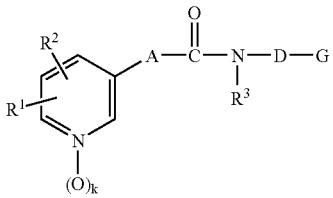
| Nr | R¹, R² | k | A | R³ | D—G |
|---|---|---|---|---|---|
| 206 | H | 0 | OCH$_2$ | H | " |
| 207 | H | 0 | CH=CH | H | " |
| 208 | 6-C$_6$H$_5$O | 0 | CH=CH | H | " |
| 209 | H | 0 | CH=CH | CH$_3$ | 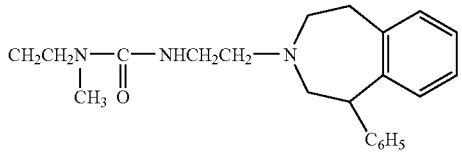 |
| 210 | H | 0 | CH$_2$CH$_2$ | H | 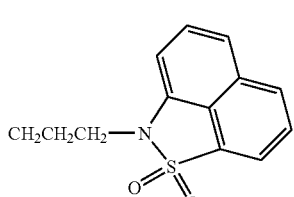 |
| 211 | H | 0 | CH=CH | H | " |
| 212 | H | 0 | CH$_2$ | H | 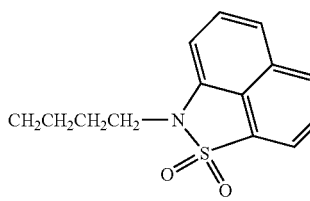 |
| 213 | H | 0 | CHCH$_2$<br>\|<br>CH$_3$ | H | " |
| 214 | H | 0 | CH=CH | H | " |
| 215 | H | 1 | CH=CH | H | " |
| 216 | 2-CH$_3$O | 0 | CH=CH | H | " |
| 217 | 5-F | 0 | CH=CH | H | " |
| 218 | 2,6-(CH$_3$)$_2$ | 0 | CH=CH | H | " |
| 219 | H | 0 | C≡C | H | " |
| 220 | H | 0 | CH$_2$CH$_2$ | H |  |
| 221 | H | 0 | CH=CH | H | " |

TABLE 1-continued

Exemplifying compounds of formula (I) according to the invention

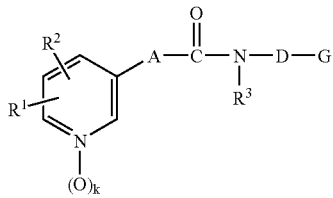

| Nr | R¹, R² | k | A | R³ | D—G |
|---|---|---|---|---|---|
| 222 | H | 0 | CH=CH | H | CH₂CH₂CH₂CH₂CH₂—N(phenanthridine) |
| 223 | H | 0 | CH=CH—CH=CH | H | " |
| 224 | H | 0 | CH₂CH₂ | H | CH₂CH₂CH₂CH₂—N(benz[de]isoquinoline) |
| 225 | H | 0 | CH=CH | H | " |
| 226 | 4-F | 0 | CH=CH | H | " |
| 227 | 6-C₂H₅S | 0 | CH=CH | H | " |
| 228 | H | 0 | CH₂CH₂ | H | (CH₂)₆—N(benz[de]isoquinoline) |
| 229 | H | 0 | CH=CH | H | " |
| 230 | H | 0 | C≡C | H | " |
| 231 | H | 0 | CH₂CH₂CH₂ | H | " |
| 232 | H | 0 | CH₂CH₂ | H | CH₂C≡CCH₂—N(dibenzazepine) |
| 233 | H | 0 | CH=CH | H | " |
| 234 | H | 0 | △ | H | " |
| 235 | H | 0 | CH=CH | H | CH₂CH₂CH₂CH₂CH₂—N(dihydrodibenzazepine) |

TABLE 1-continued

Exemplifying compounds of formula (I) according to the invention

| Nr | R¹, R² | k | A | R³ | D—G |
|---|---|---|---|---|---|
| 236 | 6-C$_6$H$_5$O | 0 | CH=CH | H | " |
| 237 | H | 0 | CH=CH | H | CH$_2$CH=CHCH$_2$-O-CH(C$_6$H$_5$)$_2$ |
| 238 | H | 0 | CH$_2$CH$_2$ | H | (CH$_2$)$_6$-O-CH(C$_6$H$_5$)$_2$ |
| 239 | H | 0 | CH=CH | H | " |
| 240 | H | 0 | CH=CH | H | CH$_2$CH$_2$CH$_2$CH$_2$-O-CH(2-thienyl)$_2$ |
| 241 | H | 0 | OCH$_2$ | H | (CH$_2$)$_6$-O-(2-naphthyl) |
| 242 | H | 0 | CH=CH | H | CH$_2$CH$_2$CH$_2$CH$_2$-O-(9-fluorenon-2-yl) |
| 243 | H | 0 | CH=CH | H | CH$_2$CH$_2$OCH$_2$CH$_2$-O-(phenanthren-9-yl) |
| 244 | H | 0 | CH$_2$CH$_2$ | H | CH$_2$CH$_2$CH$_2$CH$_2$-S-CH(C$_6$H$_5$)$_2$ |
| 245 | H | 0 | CH=CH | H | CH$_2$CH$_2$CH$_2$CH(OH)CH$_2$-S-CH(C$_6$H$_5$)$_2$ |

TABLE 1-continued

Exemplifying compounds of formula (I) according to the invention

| Nr | R¹, R² | k | A | R³ | D—G |
|---|---|---|---|---|---|
| 246 | H | 0 | CH$_2$CH$_2$ | H | CH$_2$CH=CHCH$_2$—S—(benzimidazol-2-yl) |
| 247 | H | 0 | CH=CH | H | CH$_2$CH$_2$CH$_2$CH$_2$—NH—C(O)—CH(C$_6$H$_5$)$_2$ |
| 248 | H | 0 | CH$_2$CH$_2$ | H | CH$_2$CH$_2$CH$_2$CH$_2$—N(C$_6$H$_5$)—C(O)—CH(C$_6$H$_5$)$_2$ |
| 249 | H | 0 | CH=CH | H | " |
| 250 | H | 0 | CH=CH | H | CH$_2$CH$_2$CH$_2$CH$_2$—NH—C(O)—(2-phenylcyclopropyl) |
| 251 | H | 0 | CH$_2$CH$_2$ | H | CH$_2$CH$_2$CH$_2$CH$_2$CH$_2$—NH—C(O)—CH=CH—C$_6$H$_5$ |
| 252 | H | 0 | CH=CH | H | (CH$_2$)$_6$—NH—C(O)—CH=C(C$_6$H$_5$)$_2$ |
| 253 | H | 0 | CH$_2$CH$_2$ | H | CH$_2$C≡CCH$_2$—NH—C(O)—CH=CH—(furan-2-yl) |
| 254 | H | 0 | OCH$_2$ | H | CH$_2$CH$_2$CH$_2$CH$_2$—NH—C(O)—CH=CH—(benzothiophen-3-yl) |
| 255 | H | 0 | CH=CH | H | CH$_2$CH$_2$CH$_2$CH$_2$—NH—C(O)—C$_6$H$_5$ |

TABLE 1-continued

Exemplifying compounds of formula (I) according to the invention

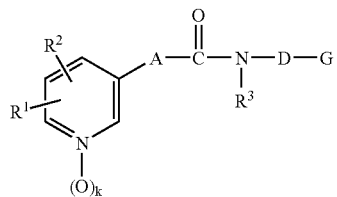

| Nr | R¹, R² | k | A | R³ | D—G |
|---|---|---|---|---|---|
| 256 | H | 0 | CH₂CH₂ | H | CH₂CH=CHCH₂—NH—C(O)—(2-naphthyl) |
| 257 | H | 0 | CH₂CH₂ | H | (CH₂)₆—NH—C(O)—(2-furyl) |
| 258 | H | 0 | CH=CH | H | " |
| 259 | H | 0 | CH=CH | H | CH₂CH₂CH₂CH₂—NH—C(O)—CH₂CH₂—N(3,4-dihydroquinolin-1-yl) |
| 260 | H | 0 | CH=CH | CH₃ | CH₂CH₂CH₂CH₂—N(CH₃)—C(O)—NH—(indan-1-yl) |
| 261 | H | 0 | CH=CH | H | CH₂CH₂CH₂CH₂—NH—C(O)—NH—CH(C₆H₅)(C₆H₅) |
| 262 | H | 0 | CH₂CH₂ | H | CH₂CH₂CH₂CH₂CH₂—NH—C(O)—NH—CH₂—(2,5-diphenylfuran-3-yl) |
| 263 | H | 0 | CH=CH | H | " |
| 264 | H | 0 | SCH₂ | H | (CH₂)₆—NH—C(S)—NH—CH₂—(2,5-diphenylfuran-3-yl) |

TABLE 1-continued
Exemplifying compounds of formula (I) according to the invention
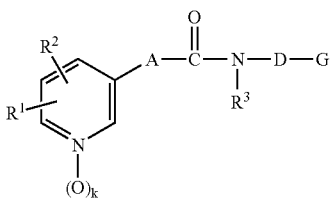
| Nr | R¹, R² | k | A | R³ | D—G |
|---|---|---|---|---|---|
| 265 | H | 0 | CH₂CH\|OH | H | 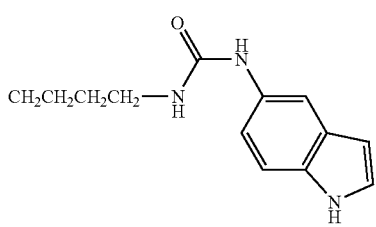 |
| 266 | H | 0 | CH=CH | H | 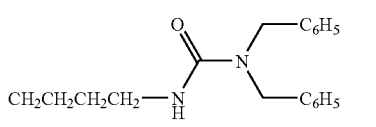 |
| 267 | H | 0 | CH₂CH₂ | H | 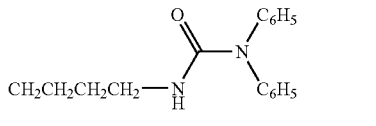 |
| 268 | H | 0 | CH=CH | H | " |
| 269 | H | 0 | CH₂CH₂CH₂CH₂ | H | " |
| 270 | H | 0 | CH=CH | H | 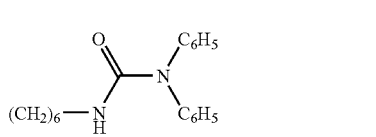 |
| 271 | H | 0 | CH₂CH\|OH | H | " |
| 272 | H | 0 | CH₂CH₂ | H | 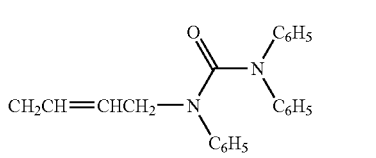 |
| 273 | H | 0 |  | H | " |
| 274 | H | 0 | CH=CH—CH=CH | H | 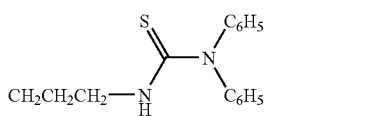 |
| 275 | H | 0 | OCH₂ | H | 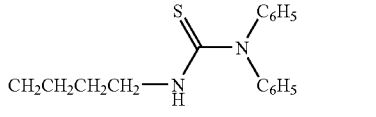 |
| 276 | 6-CH₃O | 0 | CH=CH | H | " |

TABLE 1-continued
Exemplifying compounds of formula (I) according to the invention
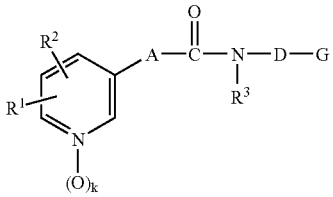
| Nr | R¹, R² | k | A | R³ | D—G |
|---|---|---|---|---|---|
| 277 | H | 0 | CH=CH | H | 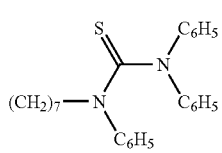 |
| 278 | H | 0 | CH₂CH₂ | H | 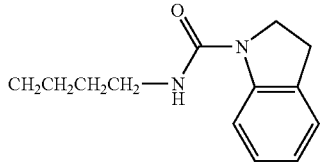 |
| 279 | H | 0 | CH=CH | H | " |
| 280 | H | 0 | CH=CH | H | 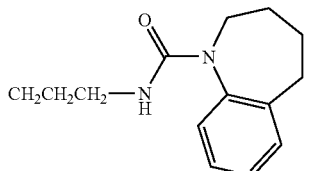 |
| 281 | H | 0 | CH₂CH₂CH₂CH₂ | H | " |
| 282 | H | 0 | SCH₂ | H | 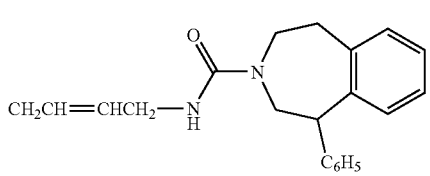 |
| 283 | H | 0 | CH=CH | H | " |
| 284 | 6-C₂H₅S | 0 | CH=CH | H | 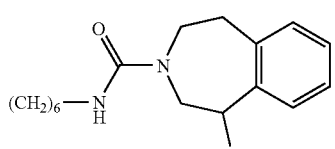 |
| 285 | H | 0 | C≡C | H | " |
| 286 | H | 0 | CH₂CH₂CH₂ | H | 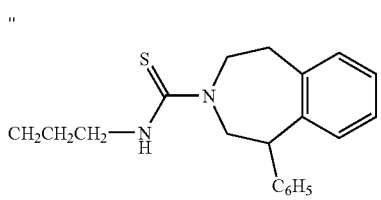 |

TABLE 1-continued
Exemplifying compounds of formula (I) according to the invention
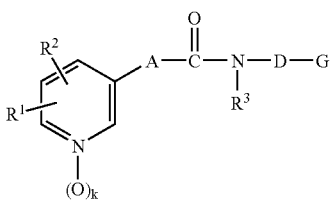
| Nr | R¹, R² | k | A | R³ | D—G |
|---|---|---|---|---|---|
| 287 | H | 0 | CH₂CH₂ | H | 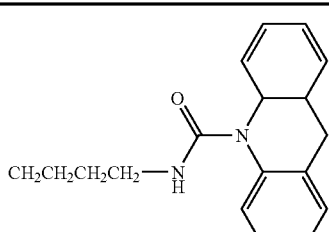 |
| 288 | H | 0 | CH₂C(=O) | H | " |
| 289 | H | 0 | CH=CH | H | 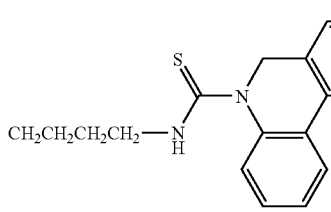 |
| 290 | H | 0 | CH₂CH₂ | H | 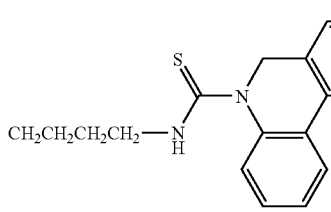 |
| 291 | H | 0 | CH=CH | H | " |
| 292 | H | 0 | CH=CH | H | 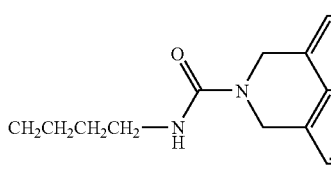 |
| 293 | H | 0 | C≡C | H | " |
| 294 | H | 0 | CH₂CH₂ | H | 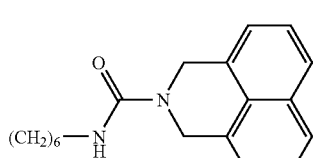 |
| 295 | H | 0 | CH=CH | H | " |

TABLE 1-continued
Exemplifying compounds of formula (I) according to the invention
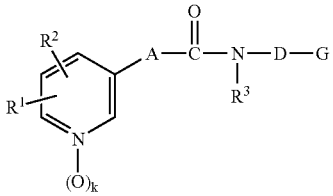
| Nr | R¹, R² | k | A | R³ | D—G |
|---|---|---|---|---|---|
| 296 | H | 0 | CH₂CH₂ | H | 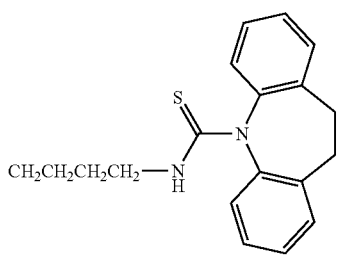 |
| 297 | H | 0 | CH=CH | H | " |
| 298 | H | 0 | OCH₂ | H | 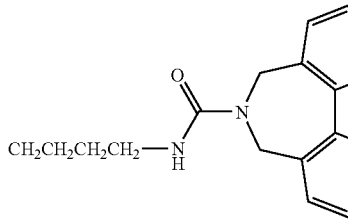 |
| 299 | 6-CH₃ | 0 | CH=CH | H | " |
| 300 | H | 0 | CH=CH | H | 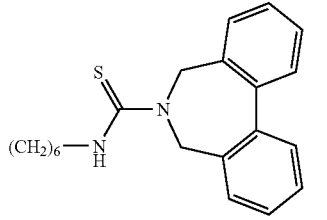 |
| 301 | H | 0 | CH₂SCH₂CH₂ | H | " |
| 302 | H | 0 | CH=CH | H | 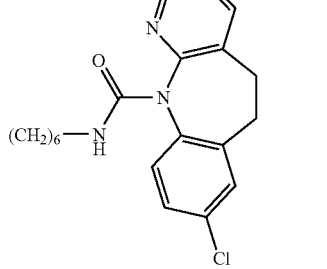 |
| 303 | H | 0 | CH₂CH₂CH₂CH₂ | H | " |

TABLE 1-continued

Exemplifying compounds of formula (I) according to the invention

| Nr | R¹, R² | k | A | R³ | D—G |
|---|---|---|---|---|---|
| 304 | H | 0 | OCH₂ | H | CH₂CH₂CH₂CH₂—NH—(dibenzazocine carbonyl) |
| 305 | H | 0 | CH=CH | H | " |
| 306 | H | 0 | CH₂CH₂ | H | CH₂CH₂CH₂CH₂—N(H)—SO₂—C₆H₅ |
| 307 | H | 0 | CH=CH | H | CH₂C≡CCH₂—N(H)—SO₂—C₆H₅ |
| 308 | H | 0 | SCH₂ | H | CH₂CH₂CH₂CH₂—N(H)—SO₂—C₆H₄—CH₃ |
| 309 | H | 0 | CH=CH | H | " |
| 310 | H | 0 | CH=CH | H | (CH₂)₆—N(H)—SO₂—C₆H₄—CH₃ |
| 311 | H | 0 | △ (cyclopropyl) | H | " |
| 312 | H | 0 | CH₂CH₂ | H | CH₂CH₂CH₂CH₂—N(H)—SO₂-(1-naphthyl) |
| 313 | H | 0 | CH=CH | H | CH₂CH₂CH₂CH₂—N(H)—SO₂-(2-naphthyl) |
| 314 | H | 0 | CH=CH—CH=CH | H | " |
| 315 | H | 0 | CH=CH | CH₃ | CH₂CH₂CH₂CH₂—N(CH₃)—SO₂-(2-naphthyl) |

TABLE 1-continued

Exemplifying compounds of formula (I) according to the invention

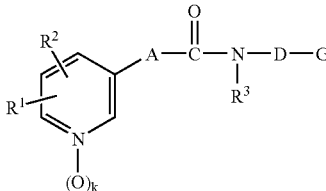

| Nr | R¹, R² | k | A | R³ | D—G |
|---|---|---|---|---|---|
| 316 | H | 0 | CH=CH | H | CH₂CH₂CH₂CH₂CH₂—NH—SO₂-(3-pyridyl) |
| 317 | H | 0 | CH=CH | H | CH₂CH₂CH₂CH₂—NH—SO₂-(5-chlorobenzothiophen-2-yl) |
| 318 | H | 0 | CH₂CH₂ | H | CH₂CH₂CH₂CH₂—NH—SO₂-(quinolin-8-yl) |
| 319 | H | 0 | CH=CH | H | " |
| 320 | H | 0 | OCH₂ | H | CH₂CH₂CH₂CH₂—NH—P(=O)(phenyl)₂ |
| 321 | H | 0 | CH=CH | H | CH₂CH₂OCH₂CH₂—NH—P(=O)(phenyl)₂ |
| 322 | H | 0 | CH₂CH₂ | H | (CH₂)₆—NH—P(=O)(phenyl)₂ |
| 323 | H | 0 | SCH₂ | H | " |
| 324 | H | 0 | CH=CH | H | " |
| 325 | H | 0 | CH=CH | H | (CH₂)₈—NH—P(=O)(phenyl)₂ |

TABLE 1-continued

Exemplifying compounds of formula (I) according to the invention

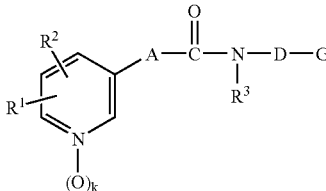

| Nr | R¹, R² | k | A | R³ | D—G |
|----|--------|---|------|-----|-----|
| 326 | H | 0 | OCH$_2$ | H | 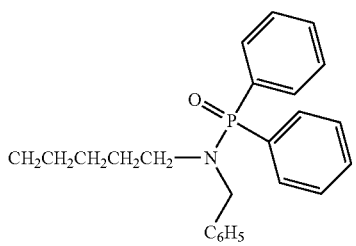 |
| 327 | H | 0 | CH=CH | H | " |
| 328 | H | 0 | CH=CH | H | 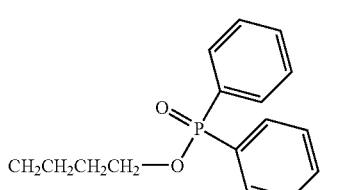 |
| 329 | H | 0 | CH$_2$CH$_2$ | H | 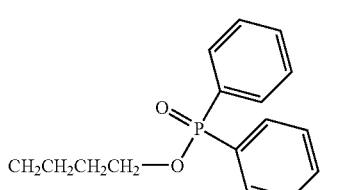 |
| 330 | H | 0 | CH=C<br>    |<br>    C$_6$H$_5$ | H | " |
| 331 | H | 0 | CH=CH | H | 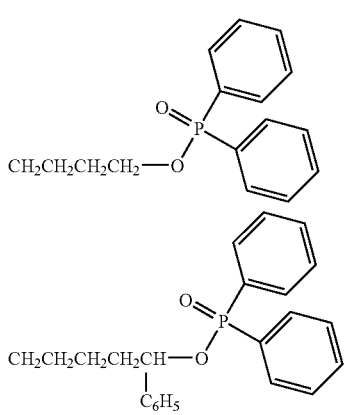 |

The active ingredients according to the invention can be processed to the desired medicaments in the form of their acid addition salts, hydrates or solvates individually or in combination with each other, optionally under addition of other active ingredients. In the case of the combination of active ingredients according to the invention with other medicinals, these can also optionally be separately present next to each other in the medicine packaging, for example as tablets next to vials, depending on the requirements.

Further subject-matter of the invent on is a method for the treatment of the human or animal body in which a compound or compound mixture according to formula (I), wherein the substituents have the above described meanings, is administered for treatment of tumors and/or as a cytostatic agent, cancerostatic agent for inhibition of abnormal cell growth, for anti-proliferative therapy or prevention or as an immunosuppressing agent, optionally in combination with further cytostatic or immunosuppressive active ingredients or other active ingredients suitable or the named indications.

Furthermore, the invention relates to a compound or compound mixture according to formula (I) for use in a therapeutic method in which the therapeutic use is carried out in connection with one or more medical indications with tumors or for immunosuppression, optimally in combination with further pharmaceuticals suitable for the named indications.

The use of one or more compounds according to formula (I) for the production of medicaments for the treatment of the human or animal body, especially in connection with one or more medical indications in the treatment of tumors or for immunosuppression, optimally in combination with further pharmaceuticals suitable in these indications or the use of compounds according to formula (I) in a corresponding diagnosis method also represent an embodiment according to the invention.

The respective suitable tumor indications are illustrated in the last section of the description in the discussion of the pharmacological test results.

A method for the production of medicaments with an amount of one or more compounds according to formula (I) which are suitable for the processing of these active ingredients together with respective suitable pharmaceutically acceptable carriers and adjuvants for finished medicinal forms equally belongs to the scope of protection according to the invention.

Depending on the medical indication being considered, the respective suitable medicinal form is selected for the suitable therapeutic application. In this connection, especially 0.001 to 1000, 2000, 3000, 4000 or 5000 mg, preferably 0.01 to 100 mg in a preferred manner 1 to 10 mg, especially also 1, 2, 5, 10, 20, 25, 30, 50, 100, 200, 300, 400, 500, 600 or 800 mg single doses are considered as applicable dose units.

The invention also relates to the use of the compounds according to formula (I) for treatment in the above indications, as well as a diagnostic agent.

In the following, the production methods for the respective suitable medicaments as well as a series of examples for medicinal forms and pharmacological activities are described for more easy understanding of the invention. These examples provided in the following as well as the above synthesis examples serve for illustration of the claims without limiting the scope of protection.

The skilled person can correspondingly modify the invention within the frame of his normal capability without deviating from the protective scope.

THERAPEUTIC ADMINISTRATION FORMS

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvants and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-syringes or single use syringes in addition to perforation bottles for multiple withdrawals.

Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micelles, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxyethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvants such as for example gelatine, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulphite and stabilizers, such as for example EDTA, are suitable as adjuvants and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvants, dispersion agents are also suitable. For production of lyophilisates, builders are also used, such as for example mannite, dextran, saccharose, human albumin, lactose, PVP or gelatine varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatine capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a regarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased A retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatine capsules.

Anti-stick and lubricant and separating agents, dispersion agents such as x-ray amorphic silicone dioxide, disintegrates, such as various starch types, PVC, cellulose esters as granulating or retarding agents, such as for example wax-like and/or polymeric compounds on the basis of Eudragit®, cellulose or Cremophor® are used as a further adjuvants for the production of compressives, such as for example tablets or hard and soft gelatine capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminium stearate, calcium stearate, talc, siliconized talc, stearic acid, acetyl alcohol or hydrated fats, etc. are also used.

In this connection, oral therapeutic systems constructed especially on osmotic principles, such as for example GIT (gastrointestinal therapeutic system) or OROS (oral osmotic system), are also to be mentioned.

Effervescent tablets or tabsolute both of which represent immediately drinkable instant medicinal forms which are quickly dissolved or suspended in water are among the perorally administrable compressives.

Among the perorally administrable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspissated juices which are formulated with water before ingestion. Ion exchange resins in combination with one or more active ingredients are also to be mentioned for the production of liquid injectable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatine or other carriers.

Hardened fat, such as for example Witepsol®, Massa Estarinum®, Novata®, coconut fat, glycerol-gelatine masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvants and carriers. Aside from suitable adjuvants and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration Instillation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthene gum, inorganic gel builders, such as for example aluminium hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvants and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and Vaseline.

Anionic, cationic or neutral tensides can be employed as emulsifiers, for example alkalized soaps, methyl soaps, amine soaps, sulfonated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, tries-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvants, such as for example isopropyl myristate, polyoxyethylene sorbitan fatty acid ester, sorbitan trioleate, lecithins or soya lecithin.

For regional application in situ, solutions for Instillation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneimformenlehre, Wissenschaftliche verlagsgesellschaft mbH, Stuttgart, (1985), 4th edition;

H. Sucker, P. Fuchs, P. Speiser, Pharmazeutische Technologie, Gecrg Thieme Verlag, Stuttgart-New York, (1991), 2nd edition;

A. T. Florence, D. Attwood, Physicochemical Principles of Pharmacy, The Maximillan Press Ltd., Hong Kong, (1981)

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York-Basel, (1987);

K. E. Avis, L. Lachmann, H. A. Liebermann, Pharmaceutical Dosage Forms Parenteral Medications, volume 2, Marcel Dekker Inc., New York-Basel, (1986);

B. W. Müller, Controlled Drug Delivery, Paperback APV, volume 17, Wissenschaftliche Verlagsgesellschaft mbH, Stuttgart, (1987);

H. Asch, D. acetic, P. C. Schmidt, Technologie von Salben, Suspensionen and Emulsionen, Wissenschaftliche Verlagsgesellschaft mbH, Stuttgart, (1984);

H. A. Liebermann, L. Lachman, J. B. Schwartz, Pharmaceutical Desage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam-London-New York-Tokyo, (1994);

J. T. Carstensen, Pharmaceutical Principles of Solid Dosage Forms, Technomic Publishing Co., Inc., Lancaster-Basel, (1993).

PRODUCTIONS EXAMPLES

1. Injection Therapeutics

| a) Parenteral Solution | |
|---|---|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

| b) Parenteral Solution | |
|---|---|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

| c) Parenteral Dispersion | |
|---|---|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

| d) Biodegradable Parenteral Depot Medicinal Form | |
|---|---|
| active ingredient used according to the invention | 10.000 g |
| polylactic acid/polygylcolic acid polymer | 70.000 g |
| polyvinylpyrrolidone | 0.200 g |
| gelatine | 2.000 g |
| soya lecithin | 2.000 g |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvant solution, which is also produced in a sterile manner, is filled. The biodegradable microparticles are mixed with the dispersion agent shortly before application and dispersed. A ready-made syringe contains 200 mg of the active compound according to the invention.

| e) Parenteral Dispersion for Subcutaneous Instillation | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1,000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called Perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvants, possibly in combination with further medicinal agents suitable for the mentioned indications.

2. Solid, Peroral Administrable Medicaments

| a) Tablets | |
|---|---|
| active ingredient used according to the invention | 10.000 g |
| lactose | 5.200 g |
| starch, soluble | 1.800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

| b) Coated Tablet Core | |
|---|---|
| active ingredient used according to the invention | 10.000 g |
| flame dispersed silicon dioxide | 500 g |
| corn starch | 2.250 g |
| stearic acid | 350 g |
| ethanol | 3.0 l |
| gelatine | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

| c) Vials for Drinking | |
|---|---|
| active ingredient used according to the invention | 0.050 g |
| glycerine | 0.500 g |
| sorbitol, 70% solution | 0.500 g |
| sodium saccharinate | 0.010 g |
| methyl-p-hydroxybenzoate | 0.040 g |
| aromatic agent | q.s. |
| sterile water | q.s. to 5 ml |

The above-mentioned components are mixed in a customary manner to a suspension and filled in a suitable drink vial having 5 ml content.

| d) Poorly Soluble Sublingual Tablets | |
|---|---|
| active ingredient used according to the invention | 0.030 g |
| lactose | 0.100 g |
| stearic acid | 0.004 g |
| talcum purum | 0.015 g |
| sweetener | q.s. |
| aromatic agent | q.s. |
| rice starch | q.s. t0 0.500 g |

The active ingredient is compacted together with the adjuvants under high pressure to sublingual tablets, favourably in oblong form.

| e) Soft Gel Capsule | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvants suitable for the encapsulation and filled into elastic soft gelatine capsules which are sealed.

| f) Hard Gelatine Capsules | |
|---|---|
| active ingredient used according to the invention | 0.150 g |
| microcrystalline cellulose | 0.100 g |
| hydroxypropylmethylcellulose | 0.030 g |
| mannite | 0.100 g |
| ethylcellulose | 0.050 g |
| triethyl citrate | 0.010 g |

The active ingredient is mixed together with the adjuvants, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatine capsule contains 150 mg of active ingredient.

3. Topically Administrable Medicinal Forms

| a) Hydrophilic Ointment | |
|---|---|
| active ingredient used according to the invention | 0.500 g |
| Eucerinum ® anhydricum | 60.000 g |
| microcrystalline wax | 15.000 g |
| Vaseline oil | q.s. to 100.000 g |

The above-mentioned adjuvants are melted and further processed together with the active ingredient to an ointment in a customary manner.

| b) Lipophilic Ointment | |
|---|---|
| active ingredient used according to the invention | 10.000 g |
| propylene glycol | 50.000 g |
| paraffin, liquid | 100.000 g |
| paraffin wax | 100.000 g |
| Vaseline | to 1000.000 ml |

The active ingredient(s) used according to the invention is dissolved in propylene glycol at ca. 60° C. At the same time, the lipophilic components are melted at 60-70° C. and subsequently combined with the active ingredient solution. The ointment is emulsified at first at 60-70° C. and subsequently cooled to 35-40° C. under constant emulsification and then filled in 10 g tubes. A tube contains 100 mg of the compound according to the invention.

4. Inhalation Therapeutic Agent

Further subject-matter is a Pharmaceutical formulation which is characterized in that it contains an active ingredient(s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-tosylate, methane sulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvants, such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

a) Controlled Dosage Aerosol

| | Intended dose per stroke | per aerosol % by weight |
|---|---|---|
| active ingredient used according to the invention | 0.500 mg | 0.66 |
| stabilizer | 0.075 mg | 0.10 |
| HFC 134a | 75.500 mg | 99.24 | b) Controlled Dosage Aerosol

| | Intended dose per stroke | per aerosol % by weight |
|---|---|---|
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings.

Alternatively, the suspension can also be produced in a suitable cooled stabilizer solution in HFC 134a/227.

The examples c) to d) describe the composition and production of dosage dry powder formulations.

c) Dosage-Dry Powder Formulation

| | mg/dose |
|---|---|
| active ingredient used according to the invention | 0.500 mg | d) Dosage-Dry Powder Formulation

| | mg/dose |
|---|---|
| active ingredient used according to the invention | 0.500 mg |
| lactose Ph. Eur. | to 2.5 mg or to 5.0 mg | e) Dosage-Dry Powder Formulation

| | mg/dose |
|---|---|
| active ingredient used according to the invention | 0.250 mg |
| lactose Ph. Eur. | to 2.5 mg or to 5.0 mg |

In example c) the active ingredient is formulated after micronization under addition of steam as pellets with an MMAD between 0, 1 and 0, 3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhalator.

In all of the examples set forth above, the active ingredient or the medicinal agent in the form of the respective suitable pharmaceutical acceptable salt and/or acid addition salts can be present, insofar as the base is not preferred in each case.

PHARMACEUTICAL EXPERIMENTAL SECTION

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM to 10 µM.

Example 1

HepG2 cells derived from a human liver carcinoma plated at a density of 20,006 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107-1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 23 | 0.05 |
| 27 | 0.04 |
| 31 | 0.008 |
| 63 | 0.008 |
| 187 | 0.2 |
| 255 | 0.5 |
| 310 | 0.08 |

Example 2

A549 cells derived from a human lung carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107-1112, 1990). The $IC_{50}$-values (defined as that concentration in which the cell growth was inhibited by 50%) was taken from the dose-response curves and given as a comparative measurement for the activity of the test compounds.

The following results were obtained according to example 2:

| Test substance No. | $IC_{50}$-value [µM] |
|---|---|
| 3 | 8 |
| 17 | 0.03 |
| 41 | 0.05 |
| 187 | 0.4 |
| 193 | 1 |
| 214 | 0.05 |
| 247 | 2 |
| 270 | 0.2 |
| 295 | 0.3 |

Example 3

HT-29 cells derived from a human colon carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107-1112, 1990). The $IC_{50}$-values (defined as that concentration in which the cell growth was inhibited by 50%) was taken from the dose-response curves and given as a comparative measurement for the activity of the test compounds as follows.

The following results were obtained according to example 3:

| Test substance No. | $IC_{50}$-value [µM] |
|---|---|
| 17 | 0.2 |
| 41 | 0.05 |
| 23 | 0.2 |
| 207 | 0.08 |
| 270 | 0.2 |

Example 4

THP-1 cells derived from a human monocytic leukemia plated at a density of 200,000 cells/ml in 96-well plastic dishes. Cultivation occurred in RPMI 1640 nutrient medium with 10% foetal calf serum (FCS) in a tissue culture incubator with a gas mixture of 5% $CO_2$ and 95% air at a temperature of 37° C. For the individual concentrations and the controls without test substances as well as for the background with nutrient medium but without cells, threefold batches were done for each. After four days of substance incubation 20 µl WST-1 reagent (Boehringer Mannheim) was respectfully pipetted in each individual well. After 30 to 60 minute incubation in the tissue culture incubator at 37° C. and 5% $CO_2$, the light extinction was measured in an ELISA reader at 450 nm wave length. The backgrounds were each subtracted from the typical measured valves. The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 120 | 0.0002 |
| 225 | 0.02 |
| 268 | 0.008 |

2. Indications

The compounds of formula (I) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynaecological tumors, ovarian carcinomas, testicle tumors, prostate carcinomas, skin cancer, kidney cancer, bladder tumors, oesophagus carcinomas, stomach cancer, rectal carcinomas, pancreas carcinomas, thyroid cancer, adrenal tumors, leukemia and lymphomas, Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic-leukemias. Benign papillomatosis tumors can also be limited in their growth with the named substances. The broad effectiveness of the new compounds were tested for example in very different human tumor cells in vitro according to the methods described in point 1. Thereby, the following $IC_{50}$ valves were obtained for the compound Nr. 120 for example:

| Cell line | Source | $IC_{50}$-values [mM] |
|---|---|---|
| A549 | lung carcinoma | 0.002 |
| HepG2 | hepatocelluar carcinoma | 0.0005 |
| THP-1 | monocytic leukemia | 0.0002 |

The novelty of the compounds can be expected to have an independent activity profile in the effectiveness against the various tumor types. Thus, tumors which are resistant to customary cytostatic agents, for example, can respond entirely to these substances. In addition, based on the independent characteristics, combinations of the new compounds with known pharmaceuticals used in chemotherapy are promising as long as their properties are complimented in a suitable manner. The integration of the new structures in a therapy scheme could be successful with one or more substances from the following classes for example: antimetabolites (for example cytarabine, 5-fluorouracil, 6-mercaptopurine, methotrexate), alkylating agents (for example busulfane, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecane, irinotecane), spindle poisons (for example vincristine, navelbine, taxol, taxoter), hormonally active agents (for example tamoxifene, flutamide, formestane, gosereline) or other cytostatic agents with complex modes of action (for example L-asparaginase, bleomycin, hydroxyurea). Resistant tumor cells can be made sensitive again for example by interaction of the new compounds with a mechanism of resistance for common cytostatic agents (for example P-glycoprotein, MRP, glutathione-S-transferase, metallothionein).

3. Immunosuppressing Activity

Many anti-tumor agents have not only a cytotoxic effect on tumor cells, but also on the blood cell system. This leads to a weakening of the immune defense, which can, in turn, be specifically employed to suppress the rejection reaction after an organ transplantation for example. Also use of the main compounds, optionally in combination with other immunological diseases (for example, psoriasis or autoimmune diseases) seems likely. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell 148 suspension over a ficoll gradient and taken up in IMEM-ZO culture medium with 0.1% dextran 70,000 and 2% foetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 µl of the fluorescent dye solutions propidium iodide (8 mg/ml) and 3,3'-dihexyloxacarbocyanin iodide (40 µg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ value [µM] |
|---|---|
| 17 | 0.005 |
| 63 | 0.0003 |
| 120 | 0.0005 |
| 207 | 0.003 |
| 214 | 0.002 |
| 225 | 0.02 |
| 247 | 0.08 |
| 268 | 0.006 |

The independent structural class of the compounds can also be expected to be successful for an efficient combination with known immunosuppressive agents such as for example cyclosporin A, tacrolimus, rapamycin, azathioprine and glucocorticoids.

The invention claimed is:
1. A pyridylalkane, pyridylalkene or pyridylalkine acid amide compound of formula (I)

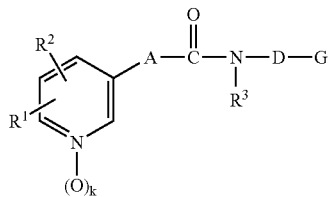

wherein
$R^1$ is selected from the group consisting of hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridylthio, and $NR^4R^5$, wherein
$R^4$ and $R^5$ are selected independently of each other from the group consisting of hydrogen, $C_1$-$C_6$-alkyl, $C_3$-$C_6$-alkenyl, $C_3$-$C_6$-alkinyl, benzyl and phenyl;
$R^2$ is selected from the group consisting of hydrogen, halogen, cyano, $C_1$-$C_6$-alkyl, trifluoromethyl, hydroxy, $C_1$-$C_6$-alkoxy and benzyloxy;
$R^3$ is selected from the group consisting of hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;
k is 0 or 1;
A is —CH=CH—;
D is selected from the group consisting of
$C_3$-$C_{12}$-alkylene,
a substituted $C_3$-$C_{12}$-alkylene which is substituted once or twice by $C_1$-$C_6$-alkyl, hydroxy, $C_1$-$C_6$-alkoxy or phenyl,
$C_3$-$C_{12}$-alkenylene,
a substituted $C_3$-$C_{12}$-alkenylene which is substituted once or twice by $C_1$-$C_6$-alkyl, hydroxy, $C_1$-$C_6$-alkoxy or phenyl,
$C_5$-$C_{12}$-alkadienylene,
a substituted $C_5$-$C_{12}$-alkadienylene which is substituted once or twice by $C_1$-$C_6$-alkyl, hydroxy, $C_1$-$C_6$-alkoxy or phenyl,
$C_3$-$C_{12}$-alkinylene,
a substituted $C_3$-$C_{12}$-alkinylene which is substituted once or twice by $C_1$-$C_6$-alkyl, hydroxy, $C_1$-$C_6$-alkoxy or phenyl,
$C_5$-$C_{12}$-alkeninylene,
a substituted $C_5$-$C_{12}$-alkeninylene which is substituted once or twice by $C_1$-$C_6$-alkyl, hydroxy, $C_1$-$C_6$-alkoxy or phenyl,
$C_3$-$C_{12}$-alkenylene or $C_3$-$C_{12}$-alkinylene, wherein, with the exception of the (G)-terminal methylene group in the $C_3$-$C_{12}$-alkenylene or $C_3$-$C_{12}$-alkinylene, one to three methylene units in the $C_3$-$C_{12}$-alkenylene or $C_3$-$C_{12}$-alkinylene are isosterically replaced by O, S, $NR^7$, CO, SO or $SO_2$, and
$C_3$-$C_{12}$-alkylene, wherein, with the exception of the G-terminal methylene group in the $C_3$-$C_{12}$ alkylene, one to three methylene units in the $C_3$-$C_{12}$ alkylene are isosterically replaced by O, S, CO, SO, or $SO_2$;

$R^7$ is hydrogen, $C_1$-$C_6$-alkyl, $C_3$-$C_6$-alkenyl, $C_1$-$C_6$-acyl, or $C_1$-$C_6$-alkanesulfonyl;
G is $G^1$ or $G^2$ wherein G must contain at least one aromatic ring, wherein
$G^1$ is —$(CR^9R^{10})_m$—$R^8$;
and
m is 0 or 1;
$R^8$ is selected from the group consisting of benzyl, diphenylmethyl, phenyl,
anellated bi- and tricyclic aromatic or partially hydrogenated carbocyclic ring systems with 8 to 18 ring atoms, and at least one aromatic ring, wherein the linkage can occur over an aromatic or a hydrogenated ring and either directly or over a methylene group;
$R^9$ is selected from the group consisting of hydrogen, $C_1$-$C_6$-alkyl, $C_3$-$C_6$-alkenyl, $C_2$-$C_6$-alkinyl, benzyl, phenyl,
anellated bi- and tricyclic aromatic ring systems with 8 to 18 ring atoms, and at least one aromatic ring, wherein the linkage can occur over an aromatic ring and either directly or over a methylene group;
$R^{10}$ is the same as $R^9$, but is selected independently thereof, or is hydroxy;
$G^2$ is =$CR^8R^9$
which is bound to D by means of a double bond, wherein $R^8$ and $R^9$ have the above meaning;
and wherein aromatic ring systems in the substitutents $R^1$, $R^2$, $R^3$, $R^4$, $R^5$, $R^8$, $R^9$, $R^{10}$, and ring system =$CR^8R^9$ may be substituted independently from each other by one to three of the same or different groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and
wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;
the cis- and trans-isomers, E- and Z-isomers including the corresponding enantiomers, diastereomers and other isomers, the tautomers and their acid addition salts including their hydrates.
2. The compound according to claim 1 wherein
$R^1$ is selected from the group consisting of hydrogen, halogen, cyano, $C_1$-$C_6$-alkyl, trifluoromethyl, ethinyl, hydroxy, $C_1$-$C_4$-alkoxy, benzyloxy, $C_1$-$C_4$-alkylthio, $C_2$-$C_5$-alkoxycarbonyl, aminocarbonyl, $C_3$-$C_9$-dialkylaminocarbonyl, carboxy, phenoxy, phenylthio, and pyridyloxy;
$R^2$ is selected from the group consisting of hydrogen, fluorine, chlorine, bromine, $C_1$-$C_4$-alkyl, trifluoromethyl, hydroxy, and $C_1$-$C_4$-alkoxy;
$R^3$ is selected from the group consisting of hydrogen, $C_1$-$C_3$-alkyl, allyl, hydroxy, $C_1$-$C_3$-alkoxy and benzyloxy;
k is 0 or 1;
D is selected from the group consisting of
$C_3$-$C_{12}$-alkylene, a substituted $C_3$-$C_{12}$-alkylene which is substituted once or twice by $C_1$-$C_3$-alkyl, hydroxy or phenyl, $C_3$-$C_{12}$-alkenylene, a substituted $C_3$-$C_{12}$-alkenylene which is substituted once or twice by $C_1$-$C_3$-alkyl, hydroxy or phenyl, $C_3$-$C_{12}$-alkinylene, a substituted $C_3$-$C_{12}$-alkinylene which is substituted once or twice by $C_1$-$C_3$-alkyl, hydroxy or phenyl, $C_3$-$C_{12}$-alkenylene or $C_3$-$C_{12}$-alkinylene, wherein, one to three methylene units in the $C_3$-$C_{12}$-alkenylene or $C_3$-$C_{12}$-alkinylene are isosterically replaced by O, S, NH, $N(CH_3)$, $N(COCH_3)$, $N(SO_2CH_3)$, CO or $SO_2$, and $C_3$-$C_{12}$-alkylene wherein one to three methylene units in $C_3$-$C_{12}$ alkylene are isosterically replaced by O, S, CO or $SO_2$;

G is selected from the group consisting of $G^1$ and $G^2$, wherein G must contain at least one aromatic ring, wherein $G^1$ is —$(CR^9R^{10})_m$—$R^8$;

and m is 0 or 1;

$R^8$ is selected from the group consisting of benzyl, diphenylmethyl, phenyl, benzocyclobutyl, indanyl, indenyl, oxoindanyl, naphthyl, dihydronaphthyl, tetrahydronaphthyl, biphenylenyl, fluorenyl, oxofluorenyl, anthryl, dihydroanthryl, oxodihydroanthryl, dioxodihydroanthryl, phenanthryl, dibenzocycloheptenyl, dihydrodibenzocycloheptenyl, oxodihydrodibenzocyclooctenyl, and tetrahydrodibenzocyclooctenyl;

$R^9$ is selected from the group consisting of hydrogen, $C_1$-$C_6$-alkyl, $C_3$-$C_6$-alkenyl, $C_2$-$C_6$-alkinyl, benzyl, phenyl, indanyl, indenyl, oxoindanyl, naphthyl, dihydronaphthyl, tetrahydronaphthyl, biphenylenyl, anthryl, dihydroanthryl, oxodihydroanthryl, phenanthryl, dibenzocycloheptenyl, dihydrodibenzocycloheptenyl, and oxodihydrodibenzocycloheptenyl;

$R^{10}$ is the same as $R^9$, but is selected independently thereof, or is hydroxyl;

$G^2$ is =$CR^8R^9$ which is bound to D over a double bond, wherein $R^8$ and $R^9$ have the above meaning;

and wherein aromatic ring systems in the substituents $R^1$, $R^3$, $R^8$, $R^9$, $R^{10}$ and =$CR^8R^9$ may be substituted independently from each other by one to three of the same or different groups selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy;

wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino.

3. The compound according to claim 2 wherein $R^1$ is selected from the group consisting of hydrogen, fluorine, chlorine, bromine, methyl, ethyl, trifluoromethyl, hydroxy, $C_1$-$C_4$-alkoxy, phenoxy, methylthio, ethylthio, methoxycarbonyl, aminocarbonyl and carboxy;

$R^2$ is selected from the group consisting of hydrogen, chlorine, methyl, hydroxy, and methoxy;

$R^3$ is hydrogen;

k is 0;

D is selected from the group consisting of $C_3$-$C_{10}$-alkylene, a substituted $C_3$-$C_{10}$-alkylene which is substituted by methyl, hydroxy or phenyl;

$C_3$-$C_{10}$-alkenylene, a substituted $C_3$-$C_{10}$-alkenylene which is substituted by methyl, hydroxy or phenyl, $C_3$-$C_{10}$-alkinylene, a substituted $C_3$-$C_{10}$-alkinylene which is substituted by hydroxy or phenyl, $C_3$-$C_{10}$-alkenylene or $C_3$-$C_{10}$-alkinylene, wherein a methylene unit is isosterically replaced by O, NH, $N(CH_3)$, or CO, and $C_3$-$C_{10}$-alkylene wherein a methylene unit is isosterically replaced by O or CO;

G is selected from the group consisting of $G^1$ and $G^2$ wherein G must contain at least one aromatic ring, wherein $G^1$ is —$(CR^9R^{10})_m$—$R^8$;

and m is 0 or 1;

$R^8$ is selected from the group consisting of benzyl, diphenylmethyl, phenyl, indanyl, indenyl, oxoindanyl, naphthyl, tetrahydronaphthyl, fluorenyl, oxofluorenyl, anthryl, dihydroanthryl, oxodihydroanthryl, phenanthryl, dibenzocycloheptenyl, dihydrodibenzocycloheptenyl, and oxodihydrodibenzocyclooctenyl;

$R^9$ is selected from the group consisting of hydrogen and $C_1$-$C_3$-alkyl, benzyl, phenyl, indanyl, indenyl, naphthyl and anthryl;

$R^{10}$ is the same as $R^9$, but is selected independently thereof, or is hydroxy;

$G^2$ is =$CR^8R^9$ which is bound to D over a double bond, wherein $R^8$ and $R^9$ have the above meaning;

and wherein aromatic ring systems in the substituents $R^1$, $R^3$, $R^8$, $R^9$, $R^{10}$, and =$CR^8R^9$ may be substituted independently from each other by one to three of the same or different groups selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy.

4. The compound according to claim 3 wherein $R^1$ is selected from the group consisting of hydrogen, fluorine, methyl, trifluoromethyl and ethylthio;

$R^2$ is hydrogen;

$R^3$ is hydrogen;

k is 0;

D is selected from the group consisting of $C_3$-$C_8$-alkylene, a substituted $C_3$-$C_8$-alkylene which is substituted by hydroxy or phenyl, $C_3$-$C_8$-alkenylene, a substituted $C_3$-$C_8$-alkenylene which is substituted by phenyl, $C_3$-$C_8$-alkinylene, $C_3$-$C_8$-alkenylene or $C_3$-$C_8$-alkinylene, wherein a methylene unit in the alkenylene or alkinylene is isosterically replaced by O, NH or CO; and G is selected from the group consisting of diphenylmethyl, diphenylhydroxymethyl, diphenylmethylene, diphenylethylene, triphenylmethyl, naphthylmethylene, naphthyl, tetrahydronaphthyl, hydroxytetrahydronaphthyl, dihydrodibenzocycloheptenyl, and hydroxydihydrodibenzocycloheptenyl, and wherein aromatic ring systems in G can be substituted independently from each other by one to three groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino.

5. A compound selected from the group consisting of

N-[8,8-bis-(4-fluorophenyl)-octyl]-3-pyridin-3-yl-acrylamide hydrochloride, N-(8,8-diphenyl-octyl)-3-pyridin-3-yl-acrylamide, N-(8-hydroxy-8,8-diphenyl-octyl)-3-pyridin-3-yl-acrylamide, N-(6-hydroxy-6,6-diphenyl-hexyl)-3-pyridin-3-yl-acrylamide, N-(6,6-diphenyl-hex-5-enyl)-3-pyridin-3-yl-acrylamide, N-(5-hydroxy-5,5-diphenyl-pentyl)-3-pyridin-3-yl-acrylamide, and N-(7-phenyl-heptyl)-3-pyridin-3-yl-acrylamide, or pharmaceutically acceptable salts thereof.

6. A pharmaceutical composition comprising one or more of the compounds according to formula (I) or pharmaceutically acceptable salts of formula (I)

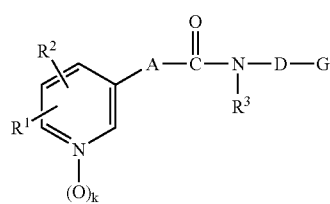

(I)

wherein $R^1$ is selected from the group consisting of hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridylthio, and $NR^4R^5$, wherein $R^4$ and $R^5$ are selected independently of each other from the group consisting of hydrogen, $C_1$-$C_6$-alkyl, $C_3$-$C_6$-alkenyl, $C_3$-$C_6$-alkinyl, benzyl and phenyl;

$R^2$ is selected from the group consisting of hydrogen, halogen, cyano, $C_1$-$C_6$-alkyl, trifluoromethyl, hydroxy, $C_1$-$C_6$-alkoxy and benzyloxy;

$R^3$ is selected from the group consisting of hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;

k is 0 or 1;

A is —CH=CH—;

D is selected from the group consisting of $C_3$-$C_{12}$-alkylene, a substituted $C_3$-$C_{12}$-alkylene which is substituted once or twice by $C_1$-$C_6$-alkyl, hydroxy, $C_1$-$C_6$-alkoxy or phenyl, $C_3$-$C_{12}$-alkenylene, a substituted $C_3$-$C_{12}$-alkenylene which is substituted once or twice by $C_1$-$C_6$-alkyl, hydroxy, $C_1$-$C_6$-alkoxy or phenyl;

$C_5$-$C_{12}$-alkadienylene, a substituted $C_5$-$C_{12}$-alkadienylene which is substituted once or twice by $C_1$-$C_6$-alkyl, hydroxy, $C_1$-$C_6$-alkoxy or phenyl, $C_3$-$C_{12}$-alkinylene, a substituted $C_3$-$C_{12}$-alkinylene which is substituted once or twice by $C_1$-$C_6$-alkyl, hydroxy, $C_1$-$C_6$-alkoxy or phenyl, $C_5$-$C_{12}$-alkeninylene, a substituted $C_5$-$C_{12}$-alkeninylene which is substituted once or twice by $C_1$-$C_6$-alkyl, hydroxy, $C_1$-$C_6$-alkoxy or phenyl, $C_3$-$C_{12}$-alkenylene or $C_3$-$C_{12}$-alkinylene, wherein, with the exception of the (G)-terminal methylene group in the $C_3$-$C_{12}$-alkenylene or $C_3$-$C_{12}$-alkinylene, one to three methylene units in the $C_3$-$C_{12}$-alkenylene or $C_3$-$C_{12}$-alkinylene are isosterically replaced by O, S, $NR^7$, CO, SO or $SO_2$ and $C_3$-$C_{12}$ alkylene, wherein, with the exception of the (G)-terminal methylene group in the $C_3$-$C_{12}$ alkylene, one to three methylene units in the $C_3$-$C_{12}$ alkylene are isosterically replaced by O, S, CO, SO or $SO_2$;

$R^7$ is hydrogen, $C_1$-$C_6$ alkyl, $C_3$-$C_6$-alkenyl, $C_1$-$C_6$-acyl or $C_1$-$C_6$ alkenesulfonyl;

G is selected from the group consisting of $G^1$ and $G^2$ wherein G must contain at least one aromatic ring, wherein $G^1$ is —$(CR^9R^{10})_m$—$R^8$;

and m is 0 or 1;

$R^8$ is selected from the group consisting of benzyl, diphenylmethyl, phenyl, anellated bi- and tricyclic aromatic or partially hydrogenated carbocyclic ring systems with 8 to 18 ring atoms, and at least one aromatic ring, wherein the linkage can occur over an aromatic or a hydrogenated ring and either directly or over a methylene group;

$R^9$ is selected from the group consisting of hydrogen, $C_1$-$C_6$-alkyl, $C_3$-$C_6$-alkenyl, $C_2$-$C_6$-alkinyl, benzyl, phenyl, anellated bi- and tricyclic aromatic ring systems with 8 to 18 ring atoms, and at least one aromatic ring, wherein the linkage can occur over an aromatic ring and either directly or over a methylene group;

$R^{10}$ is the same as $R^9$, but is selected independently thereof, or is hydroxy;

$G^2$ is =$CR^8R^9$ which is bound to D by means of a double bond, wherein $R^8$ and $R^9$ have the above meaning;

and wherein aromatic ring systems in the substitutents $R^1$, $R^2$, $R^3$, $R^4$, $R^5$, $R^8$, $R^9$, $R^{10}$, and in ring $=CR^8R^9$ may be substituted independently from each other by one to three of the same or different groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;

the cis- and trans-isomers, E- and Z-isomers including the corresponding enantiomers, diastereomers and other isomers, the tautomers and their acid addition salts including their hydrates.

7. The pharmaceutical composition of claim 6 wherein the composition is provided in a form selected from the group consisting of solid, peroral administrable form as a tablet, capsule, coated tablet, liquid, gastric fluid-resistant preparation, suspension, effervescent tablet, tab or sachet, sustained action form, parenteral depot medicinal form, implant, inhalant, concentrate, powder, rectal administrable emulsion, genital administrable emulsion, transurethral administrable emulsion, liposomal administrable emulsion, lyophilisate, spray, transdermal, salve, emulsion, balm, plaster and mixtures thereof.

8. The pharmaceutical composition of claim 6 wherein a dosage unit for administration includes 0.001 to 5000 mg active ingredient.

9. The pharmaceutical composition of claim 8 wherein a dosage unit for administration includes 0.001 to 4000 mg active ingredient.

10. The pharmaceutical composition of claim 9 wherein a dosage unit for administration includes 0.001 to 3000 mg active ingredient.

11. The pharmaceutical composition of claim 10 wherein a dosage unit for administration includes 0.001 to 2000 mg active ingredient.

12. The pharmaceutical composition of claim 11 wherein a dosage unit for administration includes 0.001 to 1000 mg active ingredient.

13. The pharmaceutical composition of claim 12 wherein a dosage unit for administration includes 0.01 to 100 mg active ingredient.

14. The pharmaceutical composition of claim 13 wherein a dosage unit for administration includes 1 to 10 mg active ingredient.

15. The pharmaceutical composition of claim 12 wherein a dosage unit for administration includes 1, 2, 5, 10, 20, 25, 30, 50, 100, 200, 300, 400, 500, 600 or 800 mg active ingredient.

16. A method of inhibiting tumor cell growth in a human or animal body comprising administering to the human or animal body in need thereof an amount of a pharmaceutical composition effective for inhibiting tumor cell growth, wherein the method is effective for inhibiting tumors selected from the group consisting of gynecological tumors, ovarian carcinomas, testicle tumors, esophagus carcinomas, stomach cancer, rectal carcinomas, pancreas carcinomas, thyroid cancer, adrenal tumors, leukemia, lymphomas, Hodgkin's disease, CNS tumors, soft-tissue sarcomas, bone sarcomas, benign and malignant mestheliomas, intestine tumors, liver tumors, breast tumors, bronchial and lung carcinomas, melanomas, and benign papillomatosis tumors, wherein the pharmaceutical composition includes compounds of formula (I) or pharmaceutically acceptable salts of formula (I)

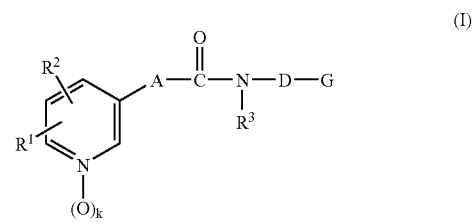

wherein $R^1$ is selected from the group consisting of hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridylthio, and $NR^4R^5$, wherein $R^4$ and $R^5$ are selected independently of each other from the group consisting of hydrogen, $C_1$-$C_6$-alkyl, $C_3$-$C_6$-alkenyl, $C_3$-$C_6$-alkinyl, benzyl and phenyl;

$R^2$ is selected from the group consisting of hydrogen, halogen, cyano, $C_1$-$C_6$-alkyl, trifluoromethyl, hydroxy, $C_1$-$C_6$-alkoxy and benzyloxy;

$R^3$ is selected from the group consisting of hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;

k is 0 or 1;

A is $-CH=CH-$;

D is selected from the group consisting of $C_3$-$C_{12}$-alkylene, a substituted $C_3$-$C_{12}$-alkylene which is substituted once or twice by $C_1$-$C_6$-alkyl, hydroxy, $C_1$-$C_6$-alkoxy or phenyl, $C_3$-$C_{12}$-alkenylene, a substituted $C_3$-$C_{12}$-alkenylene which is substituted once or twice by $C_1$-$C_6$-alkyl, hydroxy, $C_1$-$C_6$-alkoxy or phenyl, $C_5$-$C_{12}$-alkadienylene, a substituted $C_5$-$C_{12}$-alkadienylene which is substituted once or twice by $C_1$-$C_6$-alkyl, hydroxy, $C_1$-$C_6$-alkoxy or phenyl, $C_3$-$C_{12}$-alkinylene, a substituted $C_3$-$C_{12}$-alkinylene which is substituted once or twice by $C_1$-$C_6$-alkyl, hydroxy, $C_1$-$C_6$-alkoxy or phenyl, $C_5$-$C_{12}$-alkeninylene, a substituted $C_5$-$C_{12}$-alkeninylene which is substituted once or twice by $C_1$-$C_6$-alkyl, hydroxy, $C_1$-$C_6$-alkoxy or phenyl, and $C_3$-$C_{12}$-alkylene, $C_3$-$C_{12}$-alkenylene or $C_3$-$C_{12}$-alkinylene, wherein, with the exception of the (G)-terminal methylene group in the $C_3$-$C_{12}$-alkylene, $C_3$-$C_{12}$-alkenylene or $C_3$-$C_{12}$-alkinylene, one to three methylene units in the $C_3$-$C_{12}$-alkylene, $C_3$-$C_{12}$-alkenylene or $C_3$-$C_{12}$-alkinylene are isosterically replaced by O, S, $NR^7$, CO, SO or $SO_2$; wherein $R^7$ is hydrogen, $C_1$-$C_6$ alkyl, $C_3$-$C_6$ alkenyl, $C_1$-$C_6$ acyl, or $C_1$-$C_6$ alkane sulfonyl;

G is selected from the group consisting of $G^1$ and $G^2$, wherein G must contain at least one aromatic ring, wherein $G^1$ is —$(CR^9R^{10})_m$—$R^8$;

and m is 0 or 1;

$R^8$ is selected from the group consisting of benzyl, diphenylmethyl, phenyl, anellated bi- and tricyclic aromatic or partially hydrogenated carbocyclic ring systems with 8 to 18 ring atoms, and at least one aromatic ring, wherein the linkage can occur over an aromatic or a hydrogenated ring and either directly or over a methylene group;

$R^9$ is selected from the group consisting of hydrogen, $C_1$-$C_6$-alkyl, $C_3$-$C_6$-alkenyl, $C_2$-$C_6$-alkinyl, benzyl, phenyl, anellated bi- and tricyclic aromatic ring systems with 8 to 18 ring atoms, and at least one aromatic ring, wherein the linkage can occur over an aromatic ring and either directly or over a methylene group;

$R^{10}$ is the same as $R^9$, but is selected independently thereof, or is hydroxy;

$G^2$ is =$CR^8R^9$ which is bound to D by means of a double bond, wherein $R^8$ and $R^9$ have the above meaning;

and wherein aromatic ring systems in the substitutents $R^1$, $R^2$, $R^3$, $R^4$, $R^5$, $R^8$, $R^9$, $R^{10}$, and =$CR^8R^9$ may be substituted independently from each other by one to three of the same or different groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;

the cis- and trans-isomers, E- and Z-isomers including the corresponding enantiomers, diastereomers and other isomers, the tautomers and their acid addition salts including their hydrates.

17. A method of suppressing autoimmune disease in a human or animal body comprising administering to the human or animal body in need thereof an amount of a pharmaceutical composition effective for suppressing autoimmune disease, wherein the pharmaceutical composition includes compounds of formula (I) or pharmaceutically acceptable salts of formula (I)

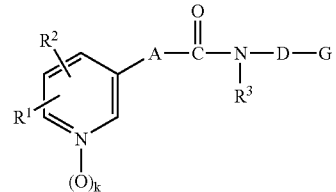

wherein $R^1$ is selected from the group consisting of hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridylthio, and $NR^4R^5$, wherein $R^4$ and $R^5$ are selected independently of each other from the group consisting of hydrogen, $C_1$-$C_6$-alkyl, $C_3$-$C_6$-alkenyl, $C_3$-$C_6$-alkinyl, benzyl and phenyl;

$R^2$ is selected from the group consisting of hydrogen, halogen, cyano, $C_1$-$C_6$-alkyl, trifluoromethyl, hydroxy, $C_1$-$C_6$-alkoxy and benzyloxy;

$R^3$ is selected from the group consisting of hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;

k is 0 or 1;

A is CH=CH—;

D is selected from the group consisting of $C_3$-$C_{12}$-alkylene, a substituted $C_3$-$C_{12}$-alkylene which is substituted once or twice by $C_1$-$C_6$-alkyl, hydroxy, $C_1$-$C_6$-alkoxy or phenyl, $C_3$-$C_{12}$-alkenylene, a substituted $C_3$-$C_{12}$-alkenylene which is substituted once or twice by $C_1$-$C_6$-alkyl, hydroxy, $C_1$-$C_6$-alkoxy or phenyl, $C_5$-$C_{12}$-alkadienylene, a substituted $C_5$-$C_{12}$-alkadienylene which is substituted once or twice by $C_1$-$C_6$-alkyl, hydroxy, $C_1$-$C_6$-alkoxy or phenyl, $C_3$-$C_{12}$-alkinylene, a substituted $C_3$-$C_{12}$-alkinylene which is substituted once or twice by $C_1$-$C_6$-alkyl, hydroxy, $C_1$-$C_6$-alkoxy or phenyl, $C_5$-$C_{12}$-alkeninylene, a substituted $C_5$-$C_{12}$-alkeninylene which is substituted once or twice by $C_1$-$C_6$-alkyl, hydroxy, $C_1$-$C_6$-alkoxy or phenyl, and $C_3$-$C_{12}$-alkylene, $C_3$-$C_{12}$-alkenylene or $C_3$-$C_{12}$-alkinylene, wherein, with the exception of the (G)-terminal methylene group in the $C_3$-$C_{12}$-alkylene, $C_3$-$C_{12}$-alkenylene or $C_3$-$C_{12}$-alkinylene, one to three methylene units in the $C_3$-$C_{12}$-alkylene, $C_3$-$C_{12}$-alkenylene or $C_3$-$C_{12}$-alkinylene are isosterically replaced by O, S, $NR^7$, CO, SO or $SO_2$, wherein $R^7$ is hydrogen, $C_1$-$C_6$ alkyl, $C_3$-$C_6$ alkenyl, $C_1$-$C_6$ acyl, or $C_1$-$C_6$ alkanesulfonyl;

G is selected from the group consisting of $G^1$ and $G^2$,
wherein G must contain at least one aromatic ring,
wherein $G^1$ is $-(CR^9R^{10})_m-R^8$;
and m is 0 or 1;

$R^8$ is selected from the group consisting of benzyl, diphenylmethyl, phenyl, anellated bi- and tricyclic aromatic or partially hydrogenated carbocyclic ring systems with 8 to 18 ring atoms, and at least one aromatic ring, wherein the linkage can occur over an aromatic or a hydrogenated ring and either directly or over a methylene group;

$R^9$ is selected from the group consisting of hydrogen, $C_1$-$C_6$-alkyl, $C_3$-$C_6$-alkenyl, $C_2$-$C_6$-alkinyl, benzyl, phenyl, anellated bi- and tricyclic aromatic ring systems with 8 to 18 ring atoms, and at least one aromatic ring, wherein the linkage can occur over an aromatic ring and either directly or over a methylene group;

$R^{10}$ is the same as $R^9$, but is selected independently thereof, or is hydroxy;

$G^2$ is $=CR^8R^9$ which is bound to D by means of a double bond, wherein $R^8$ and $R^9$ have the above meaning;

and wherein aromatic ring systems in the substitutents $R^1$, $R^2$, $R^3$, $R^4$, $R^5$, $R^8$, $R^9$, $R^{10}$, and $=CR^8R^9$ may be substituted independently from each other by one to three of the same or different groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;

the cis- and trans-isomers, E- and Z-isomers including the corresponding enantiomers, diastereomers and other isomers, the tautomers and their acid addition salts including their hydrates.

18. A method for the production of a compound of formula (I)

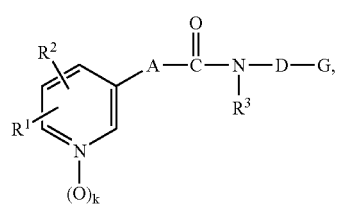

(I)

the method comprising reacting a compound of formula (II)

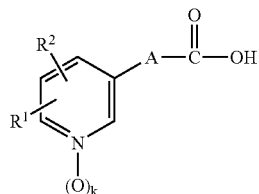

(II)

with compounds of formula (III)

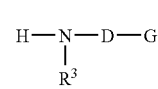

(III)

in an inert solvent or polar aprotic solvent or solvent mixture or in the presence of auxiliary base in the form of a carbonate or organic amine at a reaction temperature between −40° C. and 180° C., wherein $R^1$ is selected from the group consisting of hydrogen, halogen, cyano, $C_1$-$C_6$-alkyl, $C_3$-$C_6$-alkenyl, $C_2$-$C_6$-alkinyl, trifluoromethyl, $C_3$-$C_8$-cycloalkyl, $C_1$-$C_6$-hydroxyalkyl, hydroxy, $C_1$-$C_6$-alkoxy, $C_3$-$C_8$-cycloalkyloxy, benzyloxy, $C_1$-$C_7$-alkanoyloxy, $C_1$-$C_6$-alkylthio, $C_2$-$C_7$-alkoxycarbonyl, aminocarbonyl, $C_2$-$C_7$-alkylaminocarbonyl, $C_3$-$C_{13}$-dialkylaminocarbonyl, carboxy, phenyl, phenoxy, phenylthio, pyridyloxy, pyridylthio, and $NR^4R^5$, wherein $R^4$ and $R^5$ are selected independently of each other from the group consisting of hydrogen, $C_1$-$C_6$-alkyl, $C_3$-$C_6$-alkenyl, $C_3$-$C_6$-alkinyl, benzyl and phenyl;

$R^2$ is selected from the group consisting of hydrogen, halogen, cyano, $C_1$-$C_6$-alkyl, trifluoromethyl, hydroxy, $C_1$-$C_6$-alkoxy and benzyloxy;

$R^3$ is selected from the group consisting of hydrogen, $C_1$-$C_6$-alkyl, $C_3$-$C_6$-alkenyl, $C_3$-$C_6$-alkinyl, hydroxy, $C_1$-$C_6$-alkoxy and benzyloxy;

k is 0 or 1;

A is $-CH=CH-$;

D is selected from the group consisting of $C_3$-$C_{12}$-alkylene, a substituted $C_3$-$C_{12}$-alkylene which is substituted once or twice by $C_1$-$C_6$-alkyl, hydroxy, $C_1$-$C_6$-alkoxy or phenyl, $C_3$-$C_{12}$-alkenylene, a substituted $C_3$-$C_{12}$-alkenylene which is substituted once or twice by $C_1$-$C_6$-alkyl, hydroxy, $C_1$-$C_6$-alkoxy or phenyl, $C_5$-$C_{12}$-alkadienylene, a substituted $C_5$-$C_{12}$-alkadienylene which is substituted once or twice by $C_1$-$C_6$-alkyl, hydroxy, $C_1$-$C_6$-alkoxy or phenyl, $C_3$-$C_{12}$-alkinylene, a substituted $C_3$-$C_{12}$-alkinylene which is substituted once or twice by $C_1$-$C_6$-alkyl, hydroxy, $C_1$-$C_6$-alkoxy or phenyl, $C_5$-$C_{12}$-alkeninylene, a substituted $C_5$-$C_{12}$-alkeninylene which is substituted once or twice by $C_1$-$C_6$-alkyl, hydroxy, $C_1$-$C_6$-alkoxy or phenyl, $C_3$-$C_{12}$-alkenylene or $C_3$-$C_{12}$-alkinylene, wherein, with the exception of the (G)-terminal methylene group in the $C_3$-$C_{12}$-alkenylene or $C_3$-$C_{12}$-alkinylene, one to three methylene units in the $C_3$-$C_{12}$-alkenylene or $C_3$-$C_{12}$-alkinylene are isosterically replaced by O, S, $NR^7$, CO, SO or $SO_2$ and $C_3$-$C_{12}$ alkylene, wherein with the exception of the G-terminal methylene group in the $C_3$-$C_{12}$ alkylene, one to three methylene group in the $C_3$-$C_{12}$ alkylene are isosterically replaced by O, S, CO, SO or $SO_2$;

$R_7$ is hydrogen, $C_1$-$C_6$ alkyl, $C_3$-$C_6$ alkenyl, $C_1$-$C_6$ acyl or $C_1$-$C_6$ alkanesulfonyl;

G is selected from the group consisting of $G^1$ and $G^2$ wherein G must contain at least one aromatic ring, wherein $G^1$ is —$(CR^9R^{10})_m$—$R^8$;

and m is 0 or 1;

$R^8$ is selected from the group consisting of benzyl, diphenylmethyl, phenyl, anellated bi- and tricyclic aromatic or partially hydrogenated carbocyclic ring systems with 8 to 18 ring atoms, and at least one aromatic ring, wherein the linkage can occur over an aromatic or a hydrogenated ring and either directly or over a methylene group;

$R^9$ is selected from the group consisting of hydrogen, $C_1$-$C_6$-alkyl, $C_3$-$C_6$-alkenyl, $C_2$-$C_6$-alkinyl, benzyl, phenyl, anellated bi- and tricyclic aromatic ring systems with 8 to 18 ring atoms, and at least one aromatic ring, wherein the linkage can occur over an aromatic ring and either directly or over a methylene group;

$R^{10}$ is the same as $R^9$, but is selected independently thereof, or is hydroxy;

$G^2$ is =$CR^8R^9$ which is bound to D by means of a double bond, wherein $R^8$ and $R^9$ have the above meaning;

and wherein aromatic ring systems in the substitutents $R^1$, $R^2$, $R^3$, $R^4$, $R^5$, $R^8$, $R^9$, $R^{10}$, and =$CR^8R^9$ may be substituted independently from each other by one to three of the same or different groups independently selected from the group consisting of halogen, cyano, $C_1$-$C_6$-alkyl, trifluoromethyl, $C_3$-$C_8$-cycloalkyl, benzyl, phenyl, hydroxy, $C_1$-$C_6$-hydroxyalkyl, $C_1$-$C_6$-alkoxy, $C_1$-$C_6$-alkoxy entirely or partially substituted by fluorine, benzyloxy, phenoxy, mercapto, $C_1$-$C_6$-alkylthio, phenylthio, sulfo, carboxy, $C_2$-$C_7$-carboxyalkyl, $C_3$-$C_7$-carboxyalkenyl, $C_2$-$C_7$-alkoxycarbonyl, benzyloxycarbonyl, nitro, amino, $C_1$-$C_6$-aminoalkyl, mono-$C_1$-$C_6$-alkylamino, di-($C_1$-$C_6$-alkyl)amino and, for two adjacent residues on the aromatic ring, methylenedioxy; and wherein alkyl residues in the group G can be substituted by one or two of the same or different groups selected from the group consisting of hydroxy, carboxy, $C_2$-$C_7$-alkoxycarbonyl, benzyloxycarbonyl, amino, mono-$C_1$-$C_6$-alkylamino and di-($C_1$-$C_6$-alkyl)amino;

the cis- and trans-isomers, E- and Z-isomers including the corresponding enantiomers, diastereomers and other isomers, the tautomers and their acid addition salts including their hydrates.

\* \* \* \* \*